US007985572B2

(12) United States Patent
Zelinski et al.

(10) Patent No.: US 7,985,572 B2
(45) Date of Patent: Jul. 26, 2011

(54) MODIFIED NITRILASES AND THEIR USE IN METHODS FOR THE PRODUCTION OF CARBOXYLIC ACIDS

(75) Inventors: Thomas Zelinski, Neuleiningen (DE); Maria Keβeler, Mannheim (DE); Bernhard Hauer, Fußgönheim (DE); Thomas Friedrich, Darmstadt (DE)

(73) Assignee: BASF SE, Ludwigshafen (DE)

( * ) Notice: Subject to any disclaimer, the term of this patent is extended or adjusted under 35 U.S.C. 154(b) by 1053 days.

(21) Appl. No.: 10/546,611

(22) PCT Filed: Feb. 24, 2004

(86) PCT No.: PCT/EP2004/001804
§ 371 (c)(1),
(2), (4) Date: Aug. 23, 2005

(87) PCT Pub. No.: WO2004/076655
PCT Pub. Date: Sep. 10, 2004

(65) Prior Publication Data
US 2006/0259999 A1    Nov. 16, 2006

Related U.S. Application Data

(60) Provisional application No. 60/450,470, filed on Feb. 27, 2003.

(51) Int. Cl.
*C12N 9/00* (2006.01)
*C12N 9/78* (2006.01)
*C12N 1/20* (2006.01)
*C12N 15/00* (2006.01)

(52) U.S. Cl. ............... 435/227; 435/183; 435/252.3; 435/320.1; 536/23.2

(58) Field of Classification Search ............... None
See application file for complete search history.

(56) References Cited

U.S. PATENT DOCUMENTS

| 5,283,193 | A | 2/1994 | Yamamoto et al. |
| 5,296,373 | A | 3/1994 | Endo et al. |
| 5,814,497 | A | 9/1998 | Favre-Bulle et al. |
| 2003/0157672 | A1 | 8/2003 | Ress-Loschke et al. |

FOREIGN PATENT DOCUMENTS

| CA | 2 347 521 | 4/2000 |
| DE | 198 48 129 | 4/2000 |
| DE | 100 10 149 | 9/2001 |
| EP | 0 229 042 | 7/1987 |
| EP | 0 332 379 | 9/1989 |
| EP | 0 348 901 | 1/1990 |
| EP | 0 449 648 | 10/1991 |
| EP | 0 473 328 | 3/1992 |
| EP | 0 527 553 | 2/1993 |
| EP | 0 610 048 | 8/1994 |
| EP | 0 610 049 | 8/1994 |
| EP | 0 666 320 | 8/1995 |
| EP | 0 780 471 | 6/1997 |
| EP | 0 974 669 | 1/2000 |
| EP | 1 142 997 | 10/2001 |
| WO | WO-92/05275 | 4/1992 |
| WO | WO-97/32030 | 9/1997 |
| WO | WO-99/64607 | 12/1999 |
| WO | WO-01/34786 | 5/2001 |
| WO | WO-01/48175 | 7/2001 |
| WO | WO-02/29079 | 4/2002 |
| WO | WO-02/099051 | 12/2002 |
| WO | WO-03/000840 | 1/2003 |
| WO | WO-03/106415 | 12/2003 |

OTHER PUBLICATIONS

Bensoussan et al. Accession ABB98538. Dec. 13, 2002.*
Chica et al. Curr Opin Biotechnol. Aug. 2005;16(4):378-84.*
Sen et al. Appl Biochem Biotechnol. Dec. 2007;143(3):212-23.*
Kobayashi, M. et al., "Nitrilase In Biosynthesis Of The Plant Hormone Indole-3-Acetic Acid From Indole-3-Acetonitrile: Cloning Of The Alcaligenes Gene and Site-Directed Mutagensis Of Cysteine Residues", Proc. Natl. Acad. Sci. USA 90 (1993), pp. 247-251.
Kobayashi, M. et al., "Versatile Nitrilases: Nitrile-Hydrolysing Enzymes", FEMS Microbiology Letters 120 (1994), pp. 217-224.
Lévy-Schil, S. et al., "Aliphatic Nitrilase From A Soil-Isolated *Comamonas testosteroni* sp.: Gene Cloning And Overexpression, Purification And Primary Structure", Gene 161 (1995), pp. 15-20.
Layh, N. et al., "Characterization And Partial Purification Of An Enantioselective Arylacetonitrilase From *Pseudomonas fluorescens* DSM 7155", Journal of Molecular Catalysis B: Enzymatic 5 (1998), pp. 467-474.
Yamamoto, K. et al., "Production of R-(-)-Mandelic Acid From Mandelonitrile By *Alcaligenes faecalis* ATCC 8570", Applied And Environmental Microbiology (1991), pp. 3028-3032.
Faber K., Biotransformations In Organic Chemistry, 2nd Edition, Springer-Verlag, Berlin (1995), pp. 122-144.
Cowan, D. et al., "Biochemistry And Biotechnology Of Mesophilic And Thermophilic Nitrile Metabolizing Enzymes", Extremophiles 2 (1998), pp. 207-216.
Pace, H. C. et al., "The Nitrilase Superfamily: Classification, Structure and Function", Genome Biology 2(1)(2001), pp. 1-8.
Kobayashi, M., et al., "Primary Structure of an Aliphatic Nitrile-Degrading Enzyme, Aliphatic Nitrilase, from *Rhodococcus rhodochrous* K22 and Expression of Its Gene and Identification of Its Active Site Residue", Biochemistry, 1992, vol. 31, pp. 9000-9007.
Watanabe, A., et al., "Investigation of the Potential Active Site of a Cyanide Dihydratase Using Site-Directed Mutagenesis", Biochimica et Biophysica Acta, 1998, vol. 1382, pp. 1-4.
"*Pseudomonas stutzeri* Gene for Cyanide Degrading Enzyme, Complete cds.", NCBI GenBank Accession No. D82961, Feb. 6, 1999.
English Translation of Notice of Reasons for Rejection Dated Jan. 5, 2010 Issued in Japanese Application No. 2006-501937.

* cited by examiner

*Primary Examiner* — Christian L Fronda
(74) *Attorney, Agent, or Firm* — Connolly Bove Lodge & Hutz, LLP

(57) ABSTRACT

The present Invention relates to new nitrilases with modified Substrate acceptance, the method to obtain them and the use of the aforesaid nitrilases. Said nitrilases are encoded by a polypeptide sequence, which at a Position corresponding to Position 296 in wild-type *Alcaligenes faecalis* comprises an amino acid which is not tyrosine. The Invention further relates to nucleic acid sequences and amino acid sequences encoding Said nitrilases, expression constructs comprising Said nucleic acid sequences, vectors comprising the nucleic acid sequences or the exPression constructs, to organisms, preferably microorganisms, comprising the nucleic acid sequences, expression constructs or vectors. The Invention additionally relates to a method for preparing carboxylic acids, preferably substituted chiral carboxylic acids from racemic nitriles.

19 Claims, 14 Drawing Sheets

| | | 1 | | | | | | | 80 |
|---|---|---|---|---|---|---|---|---|---|

```
Nit285_COMTE    (1) ------------------------------MKNYPTVKVAAVQAAPVFMNLEATVDKTCKLIAEAASMGAKVIGFPEAFIPGYPYW
NitoxB1_BACSU   (1) ------------------------------SNYPKYRVAAVQASPVLLDLDATIDKTCRLVDEAAANGAKVIAFPEAFIPGYPMW
Nit_PSEST       (1) ------------------------------MAHYPKFKAAAVQAAPVYLNLDATVEKSVKLIEEAASNGAKLIEEAAASNGAKLIAFPEAFIPGYPWF
CYHY_LEPMA      (1) ------------------------------MPLTKYKAAAAVTSEPAWFNLEAGVQKTIDFINEAGQAGCKLIAFPPEVWIPGYPYW
Nit_NECHA       (1) ------------------------------MPITKYKAAAAVTSEPGWFDLEAGVVKTIDFINEAGQAECKLVAFPEVWIPGYPYW
CYHY_GLOSO      (1) ------------------------------MPINKYKAAVVTSEPVWENLEGGVVKTIEFINEAGKAGCKLIAFPEVWIPGYPYW
CYHY_GIBBA      (1) ------------------------------MAITKYKAAAAVTSEPGWFDLEGGVRKTIDFINEAGEAGCKFVAFPEVWIPGYPYW
Nit_KLEPN       (1) ------------------------------MDTTFKAAAVQAEPVWMDAAATADKTVTLVAKAAAAGAQLVAFPELWIPGYPGF
NitPA34_RHORH   (1) ------------------------------MVEYTNTFKVAAVQAQPVWFDAAKTVDKTVSIIAEAARNGCELVAFPEVFIPGYPYH
NitAAO20933     (1) ------------------------------MVEYTNTFKVAAVQAQPVWFDAAKTVDKTVSIIAEAARNGCELVAFPEVFIPGYPYH
NitSD826_RHOSP  (1) ------------------------------MVEYTNTFKVAAVQAQPVWFDAAKTVDKTVSIIAEAARNGCELVAFPEVFIPGYPYH
Nit11216_RHORH  (1) ------------------------------MVEYTNTFKVAAVQAQPVWFDAAKTVDKTVSIIAEAARNGCELVAFPEVFIPGYPYH
NitAAO20934     (1) ------------------------------MVEYTNTFKVAAVQAQPVWFDAAKTVDKTVSIIAEAARNGCELVAFPEVFIPGYPYH
NitJ1_RHORH     (1) ------------------------------VEYTNTFKVAAVQAQPVWFDAAKTVDKTVSIIAEAARNGCELVAFPEVFIPGYPYH
NitK22_RHORH    (1) -------------------------MSSNPELKYTGKVKVATVQAEPVILDADATIDKAIGFIEEAAKNGAEFLAFPEVMIPGYPYW
NitMA-1_GORTE   (1) ------------------------------MTTDYSGTFKAAVTQAEPVWFDLSATVDKTIALVEEASRAGADLIAFPETWLPGYPWF
NitJM3_ALCFA    (1) ------------------------------MQTRKIVRAAAVQAASPNYDLATGVDKTIELARQARDEGCDLIVFGETWLPGYPWF
Nit8750_ALCFA   (1) ------------------------------MQTRKIVRAAAVQAASPNYDLATGVDKTIELARQARDEGCDLIVFGETWLPGYPFH
Nit1650_ALCFA   (1) ------------------------------MQTRKIVRAAAVQAASPNYDLATGVDKTIELARQARDEGCDLIVFGETWLPGYPFH
NitAAE05488     (1) ------------------------------MSEPMTKYRGAAVQAAPVFLDLDRTVEKAIGLIEQAAKQDVRLIAFPETWIPGYPFW
Nit338_PSESP    (1) ------------------------------MTVHKKQYKVAAVQAAPAFLDLEAGVAKAIGLIAQAAAEGASLVAFPEAMLPGYPWW
Nit_BRAJA       (1) ------------------------------MQDTKFPKVAVVQAAPVFMDAPASVAKAIGFIAEAGAGAKLLAFPEVMIPGYPMW
NitAAE05489     (1) ------------------------------MKEAIKVACVQAAPIYMDLEATVDKTIELMEEAARNNARLIAFPETWIPGYPWF
Nit4_ORYSA      (1) MAMVPSGSGGGPPVIAEVEMNGGATSGAATVRATVVQASTVFYDTPATLDKAERLIEEAAGYGSQLVVFPEAFVGGYPRG
Nit4_TOBAC      (1) MALVPTPAVNEGPLFAEVDMG--DNSSTPTVRATVVQASTIFYDTPATLVKAERLLAEAASYGAQLVVFPEAFIGGYPRG
NRL4_ARATH      (1) ----------------------------------------------------------------------GYPRG
Nit2_BRANA      (1) ------------MSGTEEMSKALKASTPGFCDMPSTIVRASIVQASTVYNDTPKTIEKAGEFIAQAASDGAQLIVFPEAYIGGYPRG
Nit1_ARATH      (1) ----------MSSTKDMSTVQNATPFNGVAPSTTVRVTIVQSSTVVNDTPATIDKAEKYIVEAASKGAELVLFPEGFIGGYPRG
Nit2_ARATH      (1) ----------------MSTSENTPFNGVASSTIVRATIVQASTVYNDTPATLEKANKFIVEAASKGSELVVFPEAFIGGYPRG
Nit3_ARATH      (1) -----------MSSTEEMSSVKNTTQVIGVDPSSTVRVTIVQSSTVVNDTPATLDKAEKFIVEAASKGAKLVLFPEAFIGGYPRG Consensus       (1)                              V      FKAAAVQAAPVWFD    ATVDKTI LI EAA   GA  LVAFPE  FIPGYPY
```

```
                              161                                                                                            240
Nit285_COMTE   (127) HRKFKPTSSERAVWGDGDGS-MAPVFKTEYGNLGGLQCWEHALPLNIAAMGSLNEQVHVASWPAFVPKGAVSSRVSSSVC
NitOxB1_BACSU  (125) HRKLKATNABKTIWGDGDGS-MMPVFETEBFGNLGGLQCWEHFLPLNVAAMASMNEQVHVASWPIGMPQEGHLFGPEQCVT
Nit_PSEST      (127) HRKMRVSVAERLCWGDGNGS-MMPVFETEIGNLGGLMCWEHNVPLDIAAMNSQNEQVHVAAMPGFFDETASS--------
CYHY_LEPMA     (126) RRKLKPTHVEKLVYGDGAGDTFTSVVPTELGRLGQLNCWENMNPFLKALNVSAGEQIHIAAWPVYPGKETLKYPDPATNV
Nit_NECHA      (126) RRKLKPTHVEKLVYGDGPGDTFMSVSETDIGRVGQLNCWENMNPFLKALNVSCGEQVHIAAWPVYPGRERQVAPDPATNY
CYHY_GLOSO     (126) RRKLKPTHVEKLVYGDGSGDSFEPVTQTEIGRLGQLNCWENMNPFLKSLAVARGEQIHVAAMPVYPDLSKQVHPDPATNY
CYHY_GIBBA     (127) PQDQAPLMLRSSFTVMDPVTPSCLSVRLRLAASGQLNCWENMNPFLKSLNVSAGEQVHVAAMPVYPGRSARFTPTLLPTM
Nit_KLEPN      (125) RRKLKPTRFERELFGEGDGS-DLQVAQTSVGRVGALNCAENLQSLNKFALAAEGEQIHISAWP---------FTLGSPVL
NitPA34_RHORH  (129) RRKLKPTHVERSVYGEGNGS-DISVYDMPFARLGALNCWEHFQTLTKYAMYSMHEQVHVASWPGM------SLYQPEVPAF
NitAAO20933    (129) RRKLKPTHVERSVYGEGNGS-DISVYDMPFARLGALNCWEHFQTLTKYAMYSMHEQVHVASWPGM------SLYQPEVPAF
NitSD826_RHOSP (129) RRKLKPTHVERSVYGEGNGS-DISVYDMPFARLGALNCWEHFQTLTKYAMYSMHEQVHVASWPGM------SLYQPEVPAF
Nit11216_RHORH (129) RRKLKPTHVERSVYGEGNGS-DISVYDMPFARLGALNCWEHFQTLTKYAMYSMHEQVHVASWPGM------SLYQPEVPAF
NitAAO20934    (129) RRKLKPTHVERSVYGEGNGS-DISVYDMPFARLGALNCWEHFQTLTKYAMYSMHEQVHVASWPGM------SLYQPEVPAF
NitJ1_RHORH    (128) RRKLKPTHVERTIYGEGNGT-DFLTHDFGFGRVGGLNCWEHFQPLSKYMMYSLNEQIHVASWPAM------FALTPDVHQL
NitK22_RHORH   (134) RRKLKPTHVERTLFGEGDGS-DLVVDQTSLGRVGSLCCWEHLQPLTKYAMYSQHEQIHIAAWPSF------SIFPGAVYAL
NitMA-1_GORTE  (129) RRKLKPTHVERTVFGEGYAR-DLIVSDTELGRVGALCCWEHLSPLSKYALYSQHEAIHIAAWPSF------SLYSEQAHAL
NitJM3_ALCFA   (127) RRKLKPTHVERTVFGEGYAR-DLIVSDTELGRVGALCCWEHLSPLSKYALYSQHEAIHIAAWPSF------SLYSEQAHAL
Nit8750_ALCFA  (127) RRKLKPTHVERTVFGEGYAR-DLIVSDTELGRVGALCCWEHLSPLSKYALYSQHEAIHIAAWPSF------SLYSEQAHAL
Nit1650_ALCFA  (127) RRKLKPTHVERTVFGEGYAR-DLIVSDTELGRVGALCCWEHLSPLSKYALYSQHEAIHIAAWPSF------SLYSEQAHAL
NitAAE05488    (128) RRKLKPTHAERTVFGEGDGS-HLAVHDTTLGRLGALCCWEHIQPLSKYAMYAADEQVHVASWPSF------SLYRGMAYAL
Nit338_PSESP   (128) RRKLKPTHVERSVYGEGDGS-DLAVHDTTLGRLGALCCAEHIQPLSKYAMYAQHEQVHIAAWPSF------SVYRGAAFQL
Nit_BRAJA      (126) RRKLKPTHVERTLYGEGDGS-DFRVESSVGRLGALCCWEHIQPLSKYAMYSMNEQVHVASWPSF------TLYRDKAYAL
NitAAE05489    (125) RRKLKPTFVERTLFGEGDGS-SLAVFETSVGRLGGLCCWEHLQPLTKYALYAQNEEIHCAAWPSF------SLYPNAAKAL
Nit4_ORYSA     (160) HRKLMPTALERIIWGFGDGS-TIPYVDTPLGKIGALICWENKMPLLRTALYGKGIELYCAPTADS-------------
Nit4_TOBAC     (154) HRKIMPTALERIIWGFGDGS-TIPVYDTPLGKIGAAICWENRMPLLRTAMYAKGIEIYCAPTADS-------------
NRL4_ARATH     (81)  HRKLMPTALERCIWGFGDGS-TIPVFDTPIGKIGAAICWENRMPSLRTAMYAKGIEIYCAPTADS-------------
Nit2_BRANA     (151) HRKLMPTSLERCIWGYGDGS-TIPVVDTPIGKLGAAICWENRMPLYRTSLYGKGIELYCAPTADG-------------
Nit1_ARATH     (150) HRKLMPTSLERCIWGQGDGS-TIPVVDTPIGKLGAAICWENRMPLYRTALYAKGIELYCAPTADG-------------
Nit2_ARATH     (143) HRKLMPTSLERCIWGQGDGS-TIPVVDTPIGKLGAAICWENRMPLYRTALYAKGIELYCAPTADG-------------
Nit3_ARATH     (150) HRKVMPTSLERCIWGQGDGS-TIPVVDTPIGKIGAAICWENRMPLYRTALYAKGIEIYCAPTADY-------------
Consensus      (161) RRKLKPTHVERTVYGEGDGS  I VYDT LGRLGAL CWEH QPLTKYAMYS  EQVHVAAWP F       LY
```

Fig. 4c

```
                    241                                                                                                         320
Nit285_COMTE  (206) ASTNAMHQIISQFYAISNQVYVIMSTNLVGQDMIDMIGKDEFS-KNFLPLG------SGNTAIIS-NTGEILASIPQDAEG
NitOxB1_BACSU (204) A-TK----------YYAISNQVFCLLSSQIWTEEQRDKICETEEQ-RNFMKVG------HGFSKIIAPNGMEIGNKLAHDEEG
Nit_PSEST     (199) ----------------HYAICNQAFVLMTSSIYSEEMKDMLCETQEERDYFNTFK-----SGHTRIYGPDGEPISDLVPAETEG
CYHY_LEPMA    (206) A---DPASDLVTPAYAIETGTWTLAPFQRLSAEGLKWNTPEGVEPETDPTTYN-----GHARIYRPDGSLVVKPDK-DFDG
Nit_NECHA     (206) A---DPASDLVTPEYAIETGAWTLAPFQRLSVEGLKKNTPEGVEPETDPSVYN-----GHARIYRPDGSLVVKPDK-DFDG
CYHY_GLOSO    (206) A---DPASDLVTPAYAIETGTWVLAPFQRISVEGLKRHTPPGVEPETDATPYN-----GHARIFRPDGSLYAKPAV-DFDG
CYHY_GIBBA    (207) P---IQPLTWLLLSMLSRLARGLLLPSSVSRLEGLKINTPEGVEPETDPSVYN-----GHARIYRPDGSLVVKPEK-DFDG
Nit_KLEPN     (195) V---GDSIGAINQVYAAETGTFVLMSTQVVGPTGIAAFEIEDRYN-PNQYLG-----GGYARIYGPDMQLKSKSLSPTEEG
NitPA34_RHORH (203) G---VDAQLTATRMYALEGQTFVVCTTQVVTPEAHEFFCENEEQR-KLIGRG-----GGFARIIGPDGRDLATPLAEDEEG
NitAAO20933   (203) G---VDAQLTATRMYALEGQTFVVCTTQVVTPEAHEFFCENEEQR-KLIGRG-----GGFARIIGPDGRDLATPLAEDEEG
NitSD826_RHOSP(203) G---VDAQLTATRMYALEGQTFVVCTTQVVTPEAHEFFCENEEQR-MLIGRG-----GGFARIIGPDGRDLATPLAEDEEG
Nit11216_RHORH(203) G---VDAQLTATRMYALEGQTFVVCTTQVVTPEAHEFFCENEEQR-KLIGRG-----GGFARIIGPDGRDLATPLAEDEEG
NitAAO20934   (203) G---VDAQLTATRMYALEGQTFVVCTTQVVTPEAHEFFCENEEQR-KLIGRG-----GGFARIIGPDGRDLATPLAEDEEG
NitJ1_RHORH   (202) G---VDAQLTATRMYALEGQTFVVCTTQVVTPEAHEFFCDNDEQR-KLIGRG-----GGFARIIGPDGRDLATPLAEDEEG
NitK22_RHORH  (208) S---VEAANDTVTRSYAIEGQTFVLASTHVIGKATQDLFAGDDDAKRALLPLG----QGWARIYGPDGKSLAEPLPEDAEG
NitMA-1_GORTE (203) G---PEVNTAASQQYAVEGQTYVLAPCAVIGDAGWEAFADTEEKR-QLIHKG-----GGYARIYGPDGRSLAEPLAPNDEG
NitJM3_ALCFA  (201) S---AKVNMAASQIYSVEGQCFTIAASSVTQETLDMLEVGEHNA-SLLKVG------GGSSMIFAPDGRTLAPYLPHDAEG
Nit8750_ALCFA (201) S---AKVNMAASQIYSVEGQCFTIAASSVTQETLDMLEVGEHNA-SLLKVG------GGSSMIFAPDGRTLAPYLPHDAEG
Nit1650_ALCFA (201) S---AKVNMAASQIYSVEGQCYVLASCATVSPEMIKVLVDTPDKE-MFLKAG-----GGFAMIFGPDGRALAEPLPETEEG
NitAAE05488   (202) G---PEVNTAASQIYAVEGGCYVALEGQCFVLASCATVSKEMLDELIDSPAKA-ELLLEG----GGFAMIYGPDGAPLCTPLAETEEG
Nit338_PSESP  (202) S---AQANNAASQVYALEGGCFVLHASAITGQDMFDMLCDTPEKA-DLLNAEGAKPGGGYSMIFGPDGQPMCEHLPQDKEG
Nit_BRAJA     (200) G---HEVNLAASQIYALEGGCFVLASCALVSQSMIDMLCTDDEKH-ALLLAG------GGHSRIIGPDGGDLVAPLAENEEG
NitAAE05489   (199) G---PDVNVAASRIYAVEGQCFVLASCALVSQSMIDMLCTDDEKH-ALLLAG------GGHSRIIGPDGGDLVAPLAENEEG
Nit4_ORYSA    (224) R---QVWQASMTHIALEGGCFVLSANQFCRRKDYPPPPEYVFTGLGEEPSPDTVVCPGGSVIISPSGEVLAGPNYEG-EA
Nit4_TOBAC    (218) R---DVWQASMTHIALEGGCFVLSANQFCRRKDYPPPPEYVFSGTEEDLTPDSIVCAGGSVIISPSGAVLAGPNYVG-EA
NRL4_ARATH    (145) R---ETWLASMTHIALEGGCFVLSANQFCRRKDYSPSPPEYMFSGSEESLTPDSVVCAGGSSIISPLGIVLGIVLAGPNYRG-EA
Nit2_BRANA    (215) S---TEWQSSMMHIALEGGCFVMSACQFCKRKDFPEHADYLFTDWYDDQHQEATVSQGGSVIISPLGKILAGPNFES-EG
Nit1_ARATH    (214) S---KEWQSSMLIHIAIEGGCFVLSACQFCQRKHFPDHPDYLFTDWYDDKEHDSIVSQGGSVISPLGQVLAGPNFES-EG
Nit2_ARATH    (207) S---KEWQSSMLHIAIEGGCFVLSACQFCLRKDFPDHPDYLFTDWYDDKEPDSIVSQGGSVISPLGQVLAGPNFES-EG
Nit3_ARATH    (214) S---LEWQASMIHIAVEGGCFVLSAHQFCKRREFPEHPDYLFNDIVDTKEHDPTVSGGGSVIISPLGKVLAGPNYES-EG
Consensus     (241) G       N AAT  YALEGQ FVLAATQVVT  E D   EE    L  G     GG ARIIGPDG  LA PL ED EG
```

```
                          401                       426
Nit285_COMTE    (355) ------------------------- 
NitOxB1_BACSU   (339) ------------------------- 
Nit_PSEST       (335) ------------------------- 
CYHY_LEPMA      (356) L------------------------ 
Nit_NECHA       (356) RDSEAEEL----------------- 
CYHY_GLOSO      (358) ETEKASSNGHA-------------- 
CYHY_GIBBA      (357) E------------------------ 
Nit_KLEPN       (347) GHS---------------------- 
NitPA34_RHORH   (355) HSDETDRATAPSDSGAPVAPPKRHGV
NitAAO20933     (355) HSDETDRATAPSDSGAPVAPPKRHGV
NitSD826_RHOSP  (355) HSDETDRATATL-------------
Nit11216_RHORH  (355) HSDETDRATATL-------------
NitAAO20934     (355) HSDETDRATASI-------------
NitJ1_RHORH     (354) HSDETDRATASI-------------
NitK22_RHORH    (358) AATLPLDAPAPAPEQKSGRAKAEA-
NitMA-1_GORTE   (345) -------------------------
NitJM3_ALCFA    (353) QEPS---------------------
Nit8750_ALCFA   (353) QEPS---------------------
Nit1650_ALCFA   (353) QEPS---------------------
NitAAE05488     (347) -------------------------
Nit338_PSESP    (351) GS-----------------------
Nit_BRAJA       (335) -------------------------
NitAAE05489     (338) -------------------------
Nit4_ORYSA      (363) -------------------------
Nit4_TOBAC      (350) -------------------------
NRL4_ARATH      (276) -------------------------
Nit2_BRANA      (351) -------------------------
Nit1_ARATH      (347) -------------------------
Nit2_ARATH      (340) -------------------------
Nit3_ARATH      (347) -------------------------
Consensus       (401)
```

```
                            321                                                                        365
WO2003000840.56     (315)   YKRVEQFSPPAEAVEPTDIAAAAS---------------------------------------
WO2003000840.168    (315)   YKRVEQFSPPSEAVEPTDIAAAAS---------------------------------------
WO2003000840.198    (315)   YKRVEHFALPGDTVAPADVDAAAS---------------------------------------
WO2003000840.218    (314)   SKRVQNMVLPLETVTEPEGPVQP----------------------------------------
WO2003000840.386    (309)   KLPVVEIEGDLRPYALGKASETGAQLEEI----------------------------------
WO2003000840.48     (301)   ---------------------------------------------------------------
WO2003000840.292    (310)   NKTVIKRHSPPELIAEQAPEEEEE---------------------------------------
WO2003000840.140    (309)   NKTVIKRHSPPELIAEQTAEEEEE---------------------------------------
WO2003000840.332    (315)   RRPVIGFGEATRKVADALPKGAEPAEALEAAE-------------------------------
NitJM3_ALCFA        (314)   MTRVHSKSVIQEEAPEPHVQSTAAPVAVSQTQDSDTLLVQEPS--------------------
Nit8750_ALCFA       (314)   MTRVHSKSVIQEEAPEPHVQSTAAPVAVSQTQDSDTLLVQEPS--------------------
Nit1650_ALCFA       (314)   MTRVHSKSVTREEAPEQGVQSKIASVAISHPQDSDTLLVQEPS--------------------
WO2003000840.384    (312)   AQRVVTLDAAFEPQNEDKGDAPALRVVAESAAAAQ----------------------------
WO2003000840.34     (312)   AARVEALGPRFEVVQSEQAEPPTQPAEAAD---------------------------------
WO2003000840.16     (311)   ANRVEYINPASGPTESLKDMGKMQMEAEQQKAALREMI-------------------------
Nit338_PSESP        (312)   MTRVHYVQPQSLPETSVLAFGAGAGGKPAPKSPSVAAFTLTQAAAE-----------------
WO2003000840.102    (314)   GNRVETLALPVDQEAEAGAGGKPAPKSPSVAAFTLTQAAAE----------------------
WO2003000840.170    (314)   ANRVETLVLPVDQVRDIDARVEAAAPQARPATGNEDPAAKPMAAE------------------
WO2003000840.280    (314)   AAQVEHFALPVDAIDSEPQATTAH---------------------------------------
WO2003000840.304    (314)   AKRVEEFSLPIDLAETTPPILGT----------------------------------------
WO2003000840.188    (315)   AKRVETMLLPVDAAEVVEPADGALNASEGRQRQFKLPA-------------------------
WO2003000840.6      (315)   ARRVEYFSLPVDAVETPPQP-------------------------------------------
WO2003000840.86     (315)   ANRVEHFSLPIDAEVMSEIRLQA----------------------------------------
WO2003000840.262    (315)   ANRVEHFSLPVDAEVMSEIRLQA----------------------------------------
WO2003000840.14     (315)   SKRVEHFSLPVDNVEPEIDAAAS----------------------------------------
WO2003000840.98     (315)   NKRVEQFALPVDTVEPVDVAAAAS---------------------------------------
WO2003000840.186    (315)   YQRVEQFALPVDTVEPADIGAAAS---------------------------------------
WO2003000840.284    (315)   YKRVEQFSPPAEALEPTDIAAAAS---------------------------------------
Consensus           (321)   RVE    SLP  D   V                      A
```

MODIFIED NITRILASES AND THEIR USE IN METHODS FOR THE PRODUCTION OF CARBOXYLIC ACIDS

RELATED APPLICATIONS

This application is a national stage application (under 35 U.S.C. 371) of PCT/EP2004/001804 filed Feb. 24, 2004 which claims benefit to U.S. provisional application 60/450,470 filed Feb. 27, 2003.

FIELD OF THE INVENTION

The present invention relates to new nitrilases with modified substrate acceptance, the method to obtain them and the use of the aforesaid nitrilases. Said nitrilases are encoded by a polypeptide sequence, which at a position corresponding to position 296 in wild-type *Alcaligenes faecalis* comprises an amino acid which is not tyrosine. The invention further relates to nucleic acid sequences and amino acid sequences encoding said nitrilases, expression constructs comprising said nucleic acid sequences, vectors comprising the nucleic acid sequences or the expression constructs, to organisms, preferably microorganisms, comprising the nucleic acid sequences, expression constructs or vectors. The invention additionally relates to a method for preparing carboxylic acids, preferably substituted chiral carboxylic acids from racemic nitriles.

BACKGROUND OF THE INVENTION

Chiral and optically active carboxylic acids are in demand for organic chemical synthesis as starting materials for a large number of pharmaceutical and crop protection active ingredients. Chiral carboxylic acids can be used for classical racemate resolution via diastereomeric salts. Of special interest are substituted and unsubstituted R-(−)- or S-(+)-mandelic acid. Enzymatic synthesis of said compounds is based on nitrilases.

Nitrilases are enzymes catalyzing the hydrolysis of nitriles into the corresponding carboxylic acids and ammonium ions (Faber, Biotransformations in Organic Chemistry, Springer Verlag, Berlin/Heidelberg, 1992, ISBN 3-540-55762-8). Nitrilases were initially discovered in plants (Thimann and Mahadevan (1964) Arch Biochem Biophys 105:133-141) and subsequently isolated from many microorganisms (Kobayashi and Shimizu (1994) FEMS Microbiology Letters 120:217-224) like those of the genera *Pseudomonas, Nocardia, Arthrobacter, Fusarium, Rhodoccocus, Klebsiella, Aureobacterium, Alcaligenes, Rhodopseudomonas, Corynebacterium* sp. strain KO-2-4, *Acinetobacter, Bacillus, Variovorax, Brevibacterium, Caseobacter, Mycobacterium*, and *Candida*. The nitrilases have varied substrate specificities but can be roughly clustered into three groups according to their specificity: nitrilases specific for aliphatic nitriles, nitrilases specific for aromatic nitriles, and nitrilases specific for arylacetonitriles (Kobayashi et al. (1993) Proc Natl Acad Sci USA 90:247-251; Kobayashi and Shimizu (1994) above mentioned; Lévy-Schil et al. (1995) Gene 161:15-20; Layh et al. (1998) J Mol Catal B: Enzymatic 5:467-474).

The enzymatic synthesis of chiral and achiral carboxylic acids and α-hydroxycarboxylic acids utilizing nitrilases is described in the art (e.g., Yamamoto et al. (1991) Appl Environ Microb 57:3028-3032; Faber, Biotransformations in Organic Chemistry, 2nd edn, Springer-Verlag, Berlin, 1995; Lévy-Schil et al. (1995) Gene 161:15-20; Cowan et al. (1998) Extremophiles 2: 207-216; WO 03/000840; WO 96/09403; WO 92/05275, EP-B 0 348 901; U.S. Pat. No. 5,283,193; EP-A-0 449 648, EP-B-0 473 328, EP-B-0 527 553, EP-B-0 332 379, U.S. Pat. No. 5,296,373, EP-A-0 610 048, EP-A-0 610 049, EP-A 0 666 320, WO97/32030). The disadvantages of these processes is that they often lead to products with only low optical purity and/or that they proceed with only low space-time yields. WO 01/34786 describes a modified nitrilase having an amino acid change of the cysteine residue at position 162. The nitrilase is used to hydrolyze 2-hydroxy-4-(methyl thio) butyronitrile. "Selectivity" within WO 01/34786 is defined as the ratio of the resulting products 2-hydroxy-4-(methyl thio) butyramide and 2-hydroxy-4-(methyl thio)butanoic acid. Nothing is said concerning selectivity of the nitrilase concerning different substrates.

Most nitrilases have a very narrow range of substrate acceptance, which made them only suitable for conversion of one or a few nitriles with acceptable efficiency. This is an obstacle for the development of a biocatalytic process for new products and leads to economically unattractive processes. Therefore, it is an objective to provide nitrilases with modified, preferably broader substrate acceptance.

SUMMARY OF THE INVENTION

Accordingly, a first embodiment of the invention relates to an isolated polypeptide encoding a nitrilase, wherein said polypeptide comprise at least one sequence selected from the group of sequences comprising a)  (K/R/H)XXXDXXGX(X*),  (SEQ ID NO: 24)

b) a sequence having a homology of at least 50% with respect to a nitrilase consensus sequence sequence selected from the group of sequences comprising i)  KAINDPVGH(X*),  (SEQ ID NO: 9)

ii)  GH(X*)SRPDV,  (SEQ ID NO: 10)

and c) a sequence having a homology of at least 35% with respect to a nitrilase consensus sequence sequence selected from the group of sequences comprising i)  DP(A/V)GH(X*)SRPDV(L/T)(S/R)L,  (SEQ ID NO: 11)
and ii)  DPAGH(X*)SRPDVLSLLV,  (SEQ ID NO: 12)

provided that in said sequence comprised in said isolated polypeptide X* represents an amino acid residue which is not tyrosine, and wherein X* is localized at a position corresponding to position 296 in wild-type *Alcaligenes faecalis* nitrilase as described by SEQ ID NO: 2. Preferably, the homology to said nitrilase consensus sequence is at least 40%, more preferably at least 60% or 80%, most preferably at least 90% or 95%.

More preferably, the nitrilase consensus sequence is DP(A/V)GH(X*)SRPDV(L/T)(S/R)L (SEQ ID NO: 11), most preferably the nitrilase consensus sequence is DPAGH(X*)SRPDVLSLLV (SEQ ID NO: 12).

Especially preferably, a nitrilase of the invention comprises a sequence selected from the group consisting of a)  (K/R)XXXDXXG(H/Y/S)(X*),  (SEQ ID NO: 13)

b)  KXXXDXXGX(X*),  (SEQ ID NO: 25)

-continued c) KAINDPVGH(X*), (SEQ ID NO: 9)

d) GH(X*)SRPDV, (SEQ ID NO: 10)

e) DP(A/V)GH(X*)SRPDV(L/T)(S/R)L, and (SEQ ID NO: 11)

f) DPAGH(X*)SRPDVLSLLV, (SEQ ID NO: 12)

wherein X stands for any amino acid and provided that in said sequence comprised in said nitrilase of the invention X* represents an amino acid residue which is not tyrosine, and wherein X* is localized at a position corresponding to position 296 in wild-type *Alcaligenes faecalis* nitrilase as described by SEQ ID NO: 2. Preferably, a nitrilase of the invention comprises a sequence selected from the group consisting of a) KAINDPVGH(X*), (SEQ ID NO: 9)

b) DP(A/V)GH(X*)SRPDV(L/T)(S/R)L, or, most preferably, (SEQ ID NO: 11)

DPAGH(X*)SRPDVLSLLV, (SEQ ID NO: 12)

Preferably, the amino acid residue X* at the position corresponding to position 296 in wild-type *Alcaligenes faecalis* nitrilase as described by SEQ ID NO: 2 is selected from the group consisting of cysteine, alanine, asparagine, glycine, serine, phenylalanine, and threonine. More preferred, the amino acid residue X* is selected from the group consisting of alanine, cysteine, asparagine, and serine. Most preferred, the amino acid residue X* is selected from the group consisting of alanine, and cysteine.

Preferably, the nitrilase of the invention exhibits a modulated—more preferably broader—substrate acceptance in comparison to a nitrilase which is identical to said nitrilase of the invention but for the amino acid residue at the position corresponding to position 296 in wild-type *Alcaligenes faecalis* nitrilase as described by SEQ ID NO: 2.

Another embodiment of the invention relates to a nucleic acid sequences encoding a nitrilase of the invention.

Yet another embodiment of the invention relates to recombinant expression constructs comprising at least one nucleic acid encoding a nitrilase of the invention.

Yet another embodiment of the invention relates to recombinant expression vectors comprising at least one recombinant expression construct of the invention and/or at least one nucleic acid encoding a nitrilase of the invention.

Another embodiment of the invention relates to a method for producing a nitrilase, preferably with modulated substrate acceptance, wherein said method comprises at least the step of substituting in a given nitrilase at least a tyrosine at a position corresponding to position 296 in wild-type *Alcaligenes faecalis* nitrilase as described by SEQ ID NO: 2 by another amino acid. Preferably said substitution is realized by a mutation of the nucleic acid encoding said nitrilase.

Another embodiment of the invention relates to a method for modulating the substrate acceptance of a nitrilase, by substituting in said nitrilase at least a tyrosine at a position corresponding to position 296 in wild-type *Alcaligenes faecalis* nitrilase as described by SEQ ID NO: 2 by another amino acid. Preferably said substitution is realized by a mutation of the nucleic acid encoding said nitrilase.

Another embodiment of the invention relates to a method for the production of carbonic acids, wherein a nitrile if transformed into the corresponding carbonic acid by action of one of one or more nitrilases of the invention.

BRIEF DESCRIPTION OF THE DRAWINGS

FIG. 4*a-f*: Alignment of full-length nitrilase amino acid sequences

Figure 1:
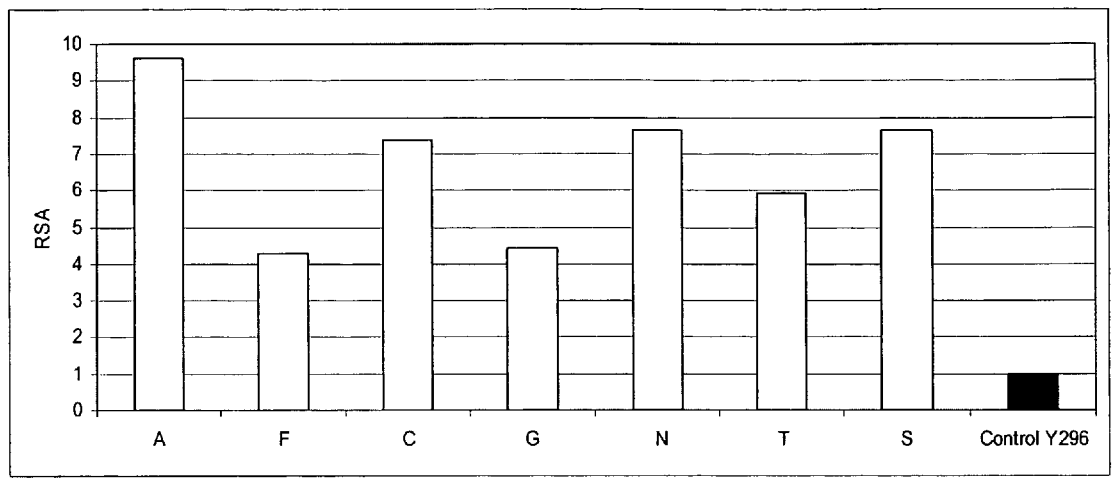
FIG. 1: Comparison of relative specific activity [RSA] with regard to conversion of racemic 2-chloromandelonitrile of various Y296 mutations with the Y296 wild-type as control/standard (see Example 2). y-axis is presenting the relative specific [RSA] activity. Specific activities were measured as described below. Relative specific activity was calculated by setting the activity of the wild-type (Y296) enzyme to 1.0. X-axis is presenting the various mutations: A (Y296A), F (Y296F), C (Y296C), G (Y296G), N (Y296N), T (Y296T), S (Y296S). Each of the tested mutants exhibits an higher activity than the wild-type Y296 nitrilase.

Presented is an alignment of the following sequences:

TABLE 1

Figure 4B:
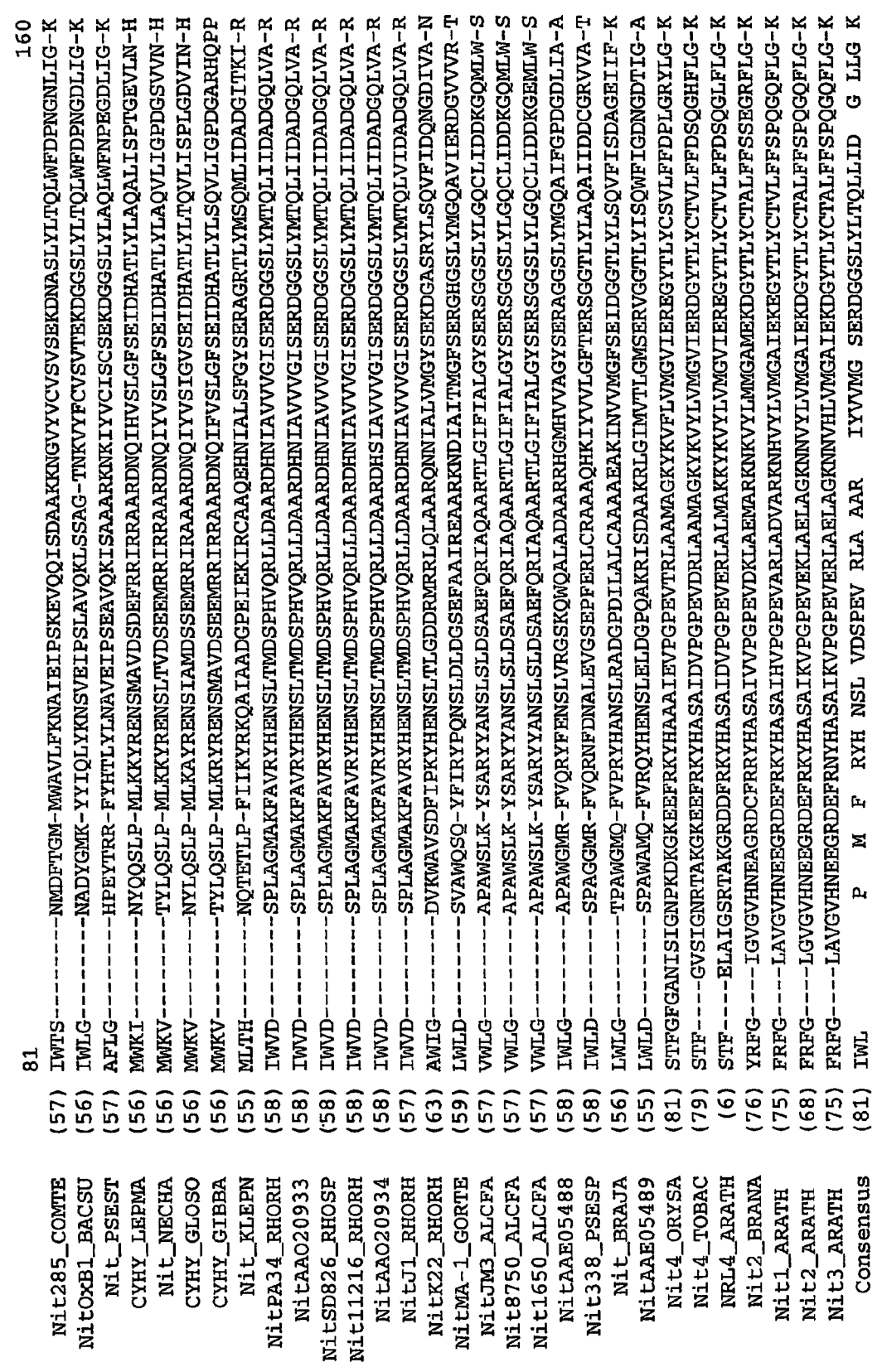

Origin and reference for sequences aligned in FIG. 4

| Name in Alignment | Reference* | Genus | Specie |
|---|---|---|---|
| Nit1650_ALCFA | DE19848129-A1 | *Alcaligenes* | *faecalis* |
| NitJM3_ALCFA | EP0527553; P20960 | *Alcaligenes* | *faecalis* |

TABLE 1-continued

Origin and reference for sequences aligned in FIG. 4

| Name in Alignment | Reference* | Genus | Specie |
|---|---|---|---|
| Nit8750_ALCFA | WO9964607-A1 | Alcaligenes | faecalis |
| Nit338_PSESP | — | Pseudomonas | spec. |
| Nit_BRAJA | BAC51667 | Bradyrhizobium | japonicum |
| NitAAE05488 | WO01/48175 | — | |
| NitAAE05489 | WO01/48175 | — | |
| NitMA-1_GORTE | EP780471; E12616 | Gordona | terrae |
| NitJ1_RHORH | Q03217 | Rhodococcus | rhodochrous |
| NitAAO20934 | WO02/29079 | — | |
| NitAAO20933 | WO02/29079 | — | |
| Nit11216_RHORH | DE10010149-A1 | Rhodococcus | rhodochrous |
| NitPA34_RHORH | E09026 | Rhodococcus | rhodochrous |
| NitSD826_RHOSP | EP1142997 | Rhodococcus | sp. |
| NitK22_RHORH | Q02068 | Rhodococcus | rhodochrous |
| NitOxB1_BACSU | P82605 | Bacillus | sp. |
| Nit285_COMTE | Q59329 | Comamonas | testosteroni |
| CYHY_LEPMA | Q9P8V3 | Leptosphaeria | maculans |
| Nit_KLEPO | P10045 | Klebsiella | pneumoniae ozaenae |
| Nit_PSEST | Q52445 | Pseudomonas | stutzeri (former Pseudomonas perfectomarina) |
| Nit_NECHA | Q96UG7 | Nectria | haematococca |
| CYHY_GLOSO | P32964 | Gloeocercospora | sorghi |
| Nit4_ORYSA | Q9SXX6 | Oryza | sativa |
| Nit3_ARATH | P46010 | Arabidopsis | thaliana |
| Nit4_TOBAC | Q42965 | Nicotiana | tabacum |
| Nit2_BRANA | Q94JL5 | Brassica | napus |
| Nit2_ARATH | P32962 | Arabidopsis | thaliana |
| Nit4_ARATH | P46011 | Arabidopsis | thaliana |
| CYHY_GIBBA | P32963 | Gibberella | baccata (former Fusarium lateritium) |
| Nit1_ARATH | P32961 | Arabidopsis | thaliana |

*Given are either GenBank or SwissProt Acc.No. or patent/patent application number.

Figure 4E:
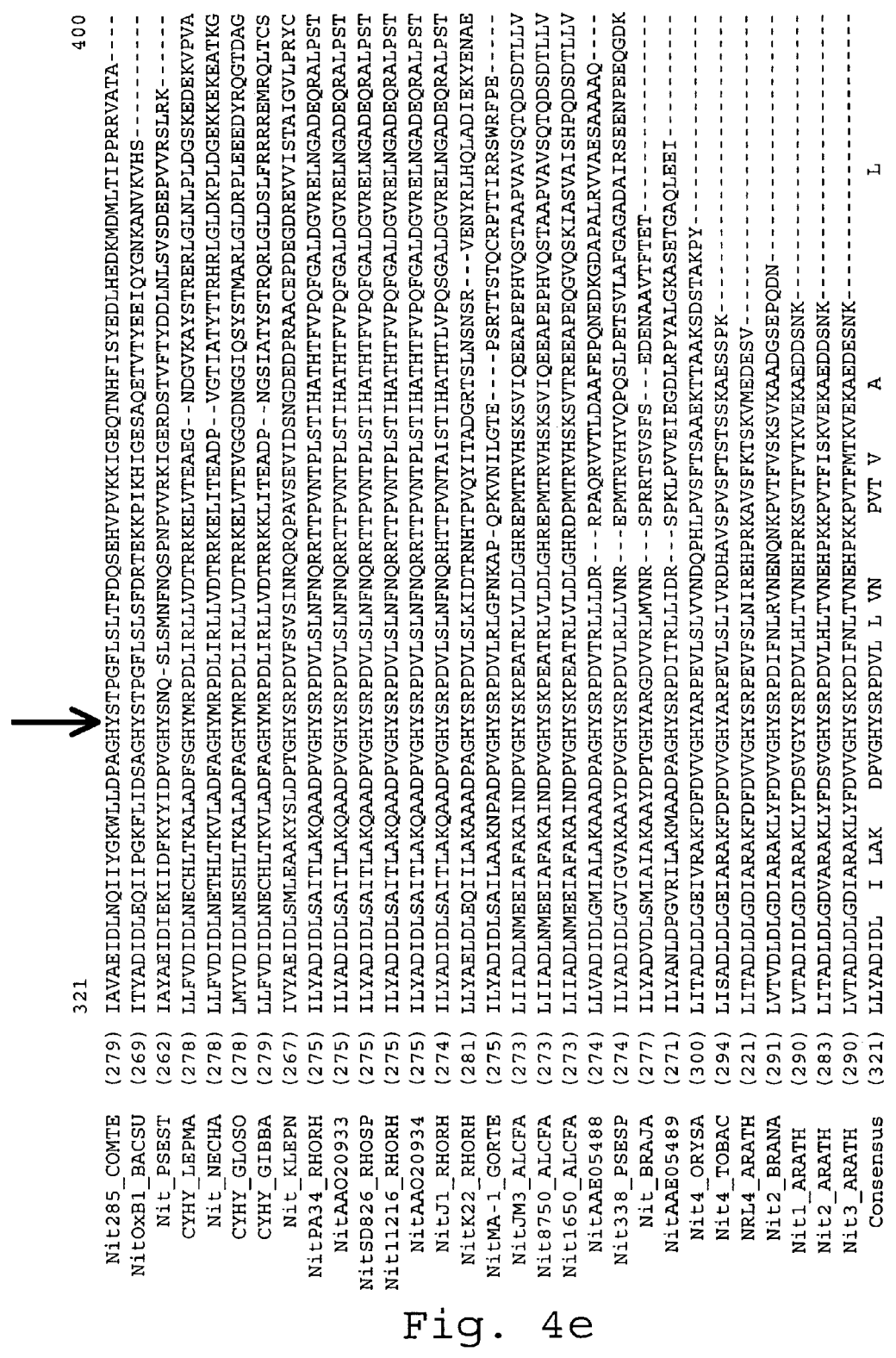

The conserved Tyrosine residue which corresponds to position 296 in wild-type *Alcaligenes faecalis* nitrilase as described by SEQ ID NO: 2 is indicated by an arrow in FIG. 4e.

Figure 5A:
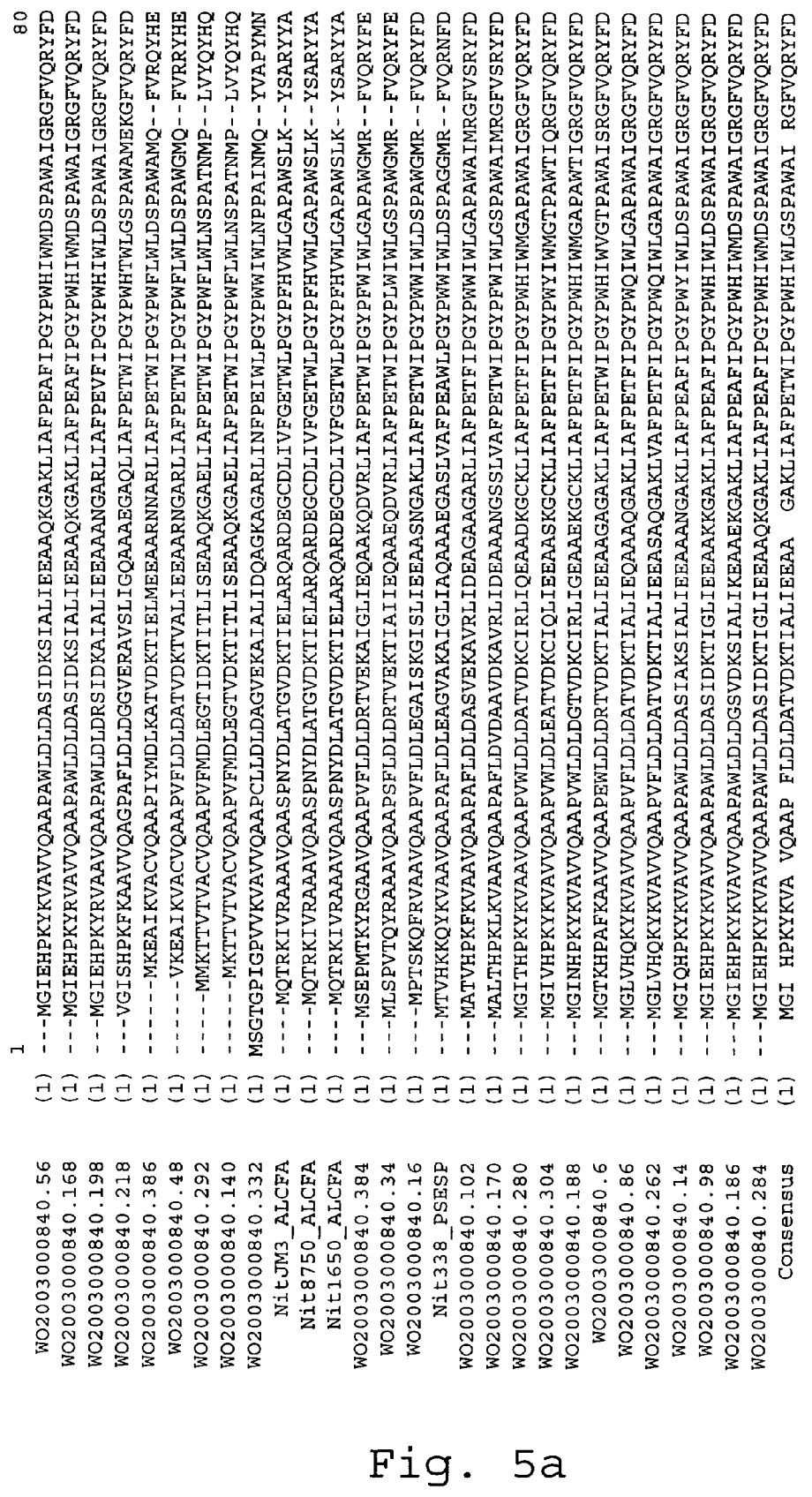
Figure 5B:
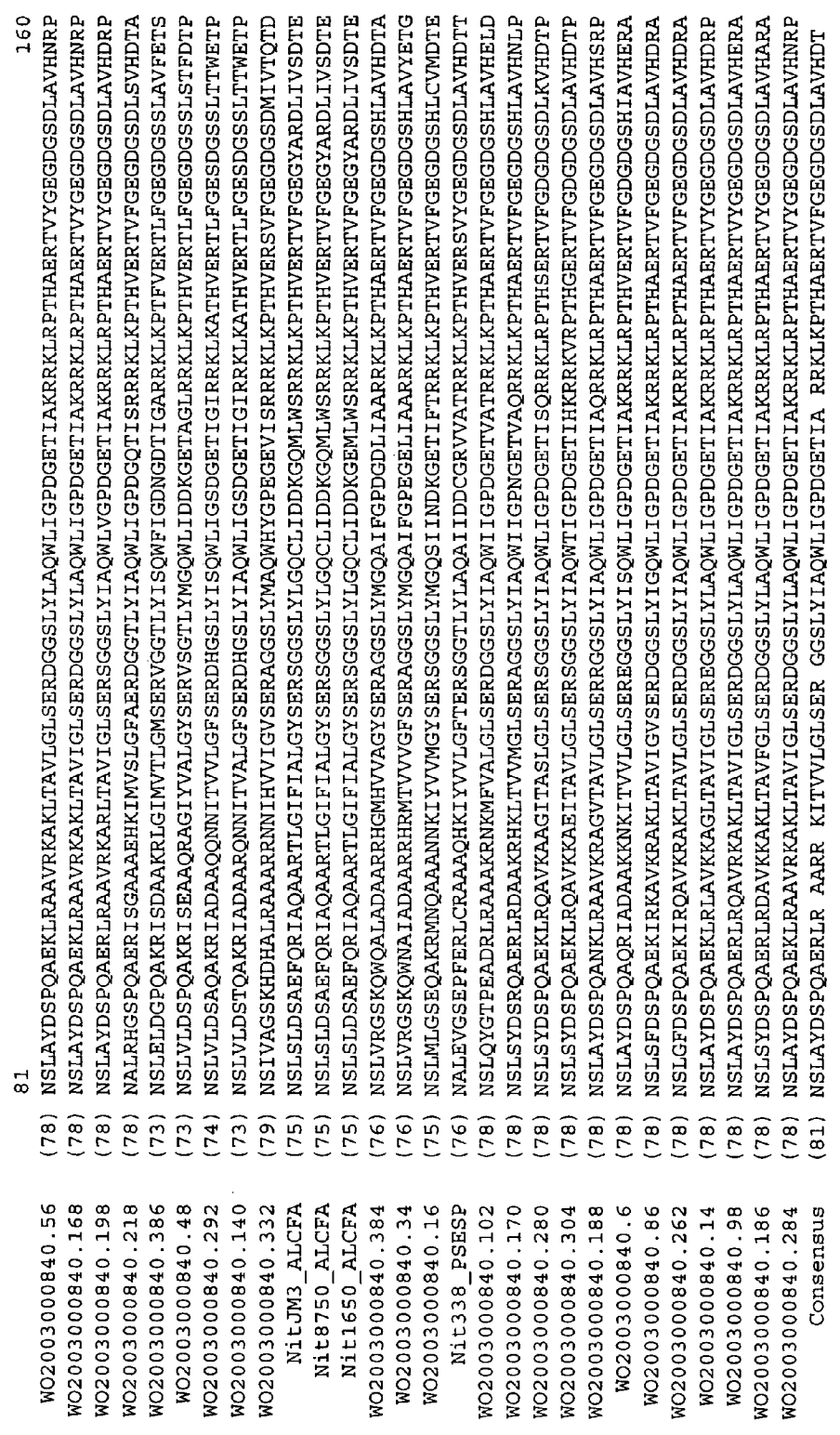
Figure 5C:
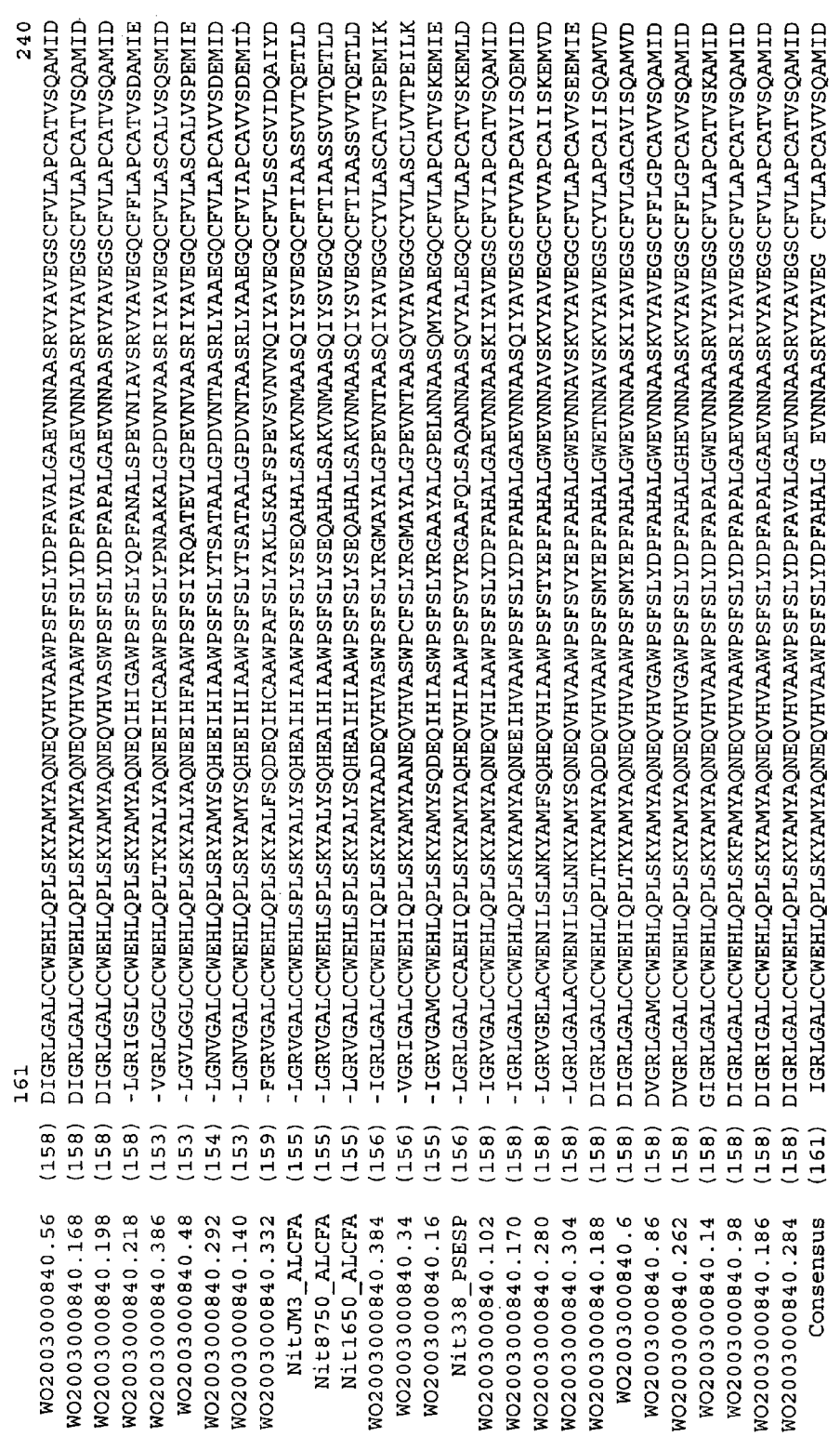
Figure 5D:
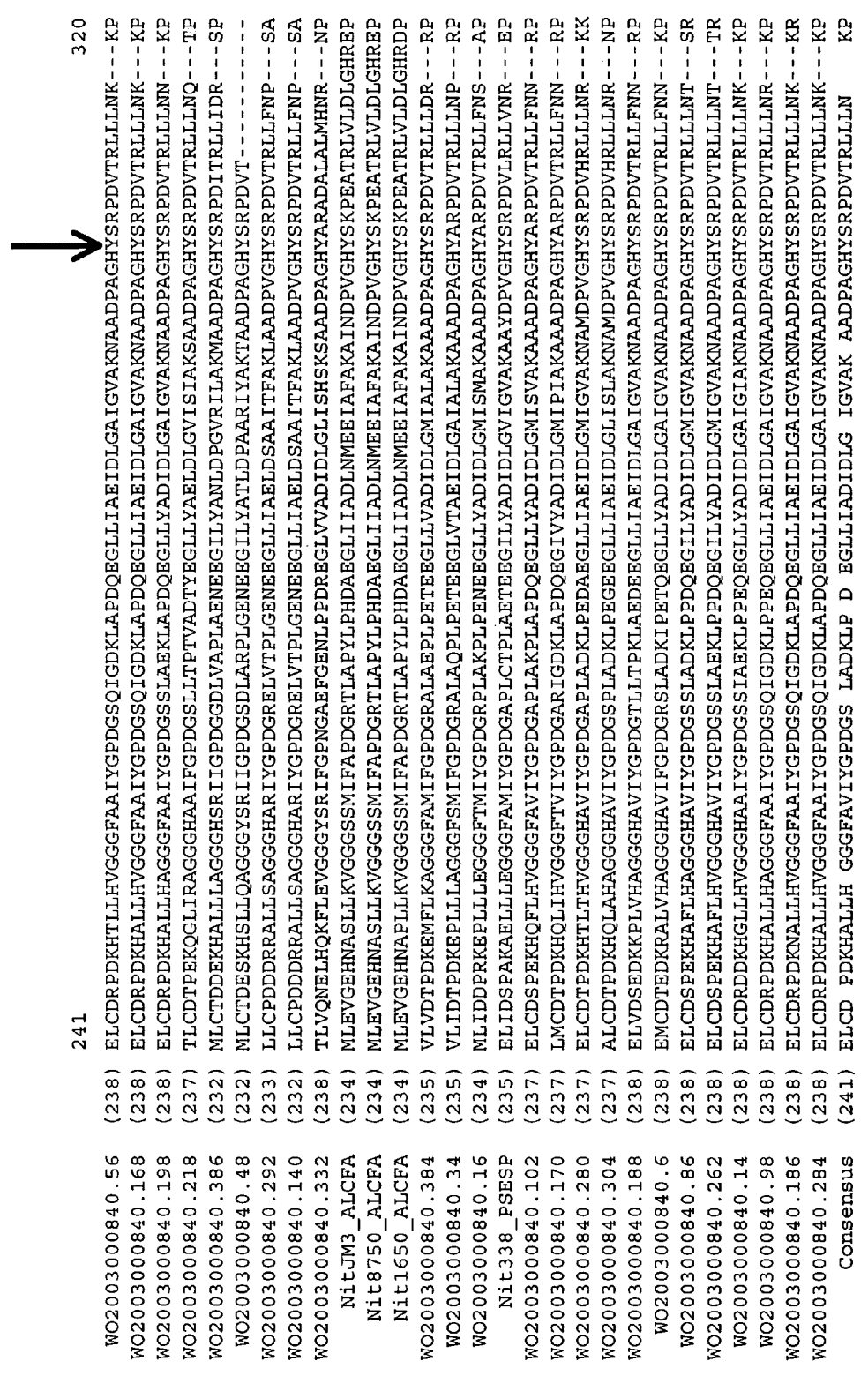

FIG. 5a-e: Alignment of full-length nitrilase amino acid sequences

Sequences disclosed in WO 03/000840 and described to exhibit R-2-chloromandelonitrile conversion activity were aligned with nitrilase from *Alcaligenes faecalis* Nit1650_ (DE19848129-A1), nitrilase from *Alcaligenes faecalis* NitJM3_(P20960; EP0527553), nitrilase from *Alcaligenes faecalis* Nit8750 (WO9964607), and nitrilase from *Pseudomonas* spec. Sequences derived from WO 03/000840 are indicated by their sequence number given after the patent application number (e.g., WO2003000840.332 present sequence no. 332 from WO 03/000840). The conserved Tyrosine residue which corresponds to position 296 in wild-type *Alcaligenes faecalis* nitrilase as described by SEQ ID NO: 2 is indicated by an arrow in FIG. 5d.

DETAILED DESCRIPTION OF THE INVENTION

The substitution of the tyrosine residue corresponding to position 296 in wild-type *Alcaligenes faecalis* leads to a modification of the substrate acceptance of the nitrilase. It was observed that the resulting nitrilases can convert nitrile substrates, which could not or only poorly be converted by the unmodified nitrilase. This allows conversion of a broad range of nitrites with economically satisfying efficacy, which can not be achieved by the nitrilases known in the art. This effect is accompanied by an increase in the catalytic activity of the enzyme on said nitrile substrates.

Accordingly, a first embodiment of the invention relates to an isolated polypeptide sequence encoding a protein with nitrilase activity, which at a position corresponding to position 296 in wild-type *Alcaligenes faecalis* nitrilase as described by SEQ ID NO: 2 comprises an amino acid which is not tyrosine.

In nearly all nitrilases described in the art the tyrosine residue corresponding to position 296 in wild-type *Alcaligenes faecalis* as described by SEQ ID NO: 2 is conserved. A small minority of polypeptides annotated as nitrilases (e.g., described in WO 03/000840) comprise a different amino acid sequence (electronically derived from the corresponding DNA) in this part of the enzyme. However, since some of these enzymes does not comprise the catalytic triad which is characteristic for all known nitrilases (see below; Pace & Brenner (2001) Genome Biology 2(1):1-9) there is a high probability that these differences are either consequence of a sequencing error (e.g., resulting in a frame shift) or that these sequences do not fall in the nitrilase super family type of enzymes. Nevertheless these enzymes have only very little or no significant homology to the region surrounding position 296 in wild-type *Alcaligenes faecalis* as described by SEQ ID NO: 2 and do not comprise the above mentioned sequences tags.

The term "corresponding to position 296 in wild-type *Alcaligenes faecalis* as described by SEQ ID NO: 2" as used herein is preferably intended to mean the position in a polypeptide sequence encoding a nitrilase which fits or aligns to the residue at position 296 in wild-type *Alcaligenes faecalis* as described by SEQ ID NO: 2 after performing a alignment of said polypeptide sequence against the sequence as described by SEQ ID NO: 2. Such an alignment can be made by using a computer software tool as for example FASTA (e.g., version 3.3t09 May 18, 2001; scoring matrix: blosum62; Henikoff & Henikoff (1992) Proc Natl Acad Sci USA 89:10915-10919; Pearson W R & Lipman D J (1988) Proc Natl Acad Sci USA 85:2444-2448), GAP, or GAP-END-Weight ("-Endweight" penalizes end gaps like other gaps; scoring matrix: blosum62 Henikoff & Henikoff (1992) Proc Natl Acad Sci USA 89:10915-10919; Needleman & Wunsch (1970) J Mol Biol 48:443-453). Positions in other nitrilase enzymes corresponding to position 296 in wild-type *Alcaligenes faecalis* as described by SEQ ID NO: 2 can also be identified by multiple alignments (as e.g., presented in FIGS. 4 and 5). The following table (Tab. 2) represents an alignment of regions comprising the residue corresponding to position 296 in wild-type *Alcaligenes faecalis* as described by SEQ ID NO: 2. Sequences were derived from GenBank/SwissProt and other sources (e.g., patent application WO 03/000840). Alignments e.g., as presented in FIGS. 4 and 5, were performed using the ClustalW algorithm (Version 1.7 as included in the AlignX feature of the Vector NTI Suite 7 Software package; Informax; Weight Matrix: Blosum for proteins); Thompson J D et al. (1994) Nucl Acids Res 22:4673-4680; Higgins D G et al. (1996) Methods Enzymol 266:383-402) using the following parameter settings: Gap opening penalty: 10; Gap extension penalty: 0.05; Gap separation penalty range: 8; % identity for alignment delay: 40.

Table 2: partial sequences from nitrilases presenting the region comprising the position 296 in wild-type *Alcaligenes faecalis* as described by SEQ ID NO: 2 (indicated by an arrow). "Nitrilase" (Column 2) presents source of the aligned sequence. Definitions are corresponding to the definitions given for the Figures (FIGS. 4 and 5). "Start (1)" is indicating the position of the first amino acid residue of the sequence tag presented in column 4 within the sequence of the corresponding nitrilase. This position can be easily used to calculate the exact position corresponding to position 296 in wild-type *Alcaligenes faecalis* as described by SEQ ID NO: 2. Similarity and identity were calculated by the GAP-ENDweight algorithm using scoring matrix: blosum62 and the parameters as defined below.

| 1 | Nitrilase | Start (1) | DPAGHYSRPDVLSLLV ↓ | % Similarity | % Identity |
|---|---|---|---|---|---|
| 2 | WO2003000840.350 | (293) | DPAGHYSRPDVLRLLF | 87.500 | 87.500 |
| 3 | WO2003000840.146 | (295) | DPAGHYSRPDVLRLLF | | |
| 4 | WO2003000840.310 | (288) | DPAGHYARPDVLQITV | | |
| 5 | WO2003000840.58 | (289) | DPAGHYSRPDVTRLLI | | |
| 6 | WO2003000840.48 | (289) | DPAGHYSRPDVTRLLI | 87.500 | 81.250 |
| 7 | NIT338_PSESP | (292) | DPVGHYSRPDVLRLLV | 87.500 | 87.500 |
| 8 | WO2003000840.12 | (294) | DPSGHYSRPDVLQLKI | | |
| 9 | WO2003000840.62 | (294) | DPSGHYSRPDVLQLKI | | |
| 10 | NitAAE05488 | (292) | DPAGHYSRPDVTRLLL | | |
| 11 | WO2003000840.386 | (289) | DPAGHYSRPDITRLLI | 87.500 | 75.000 |
| 12 | WO2003000840.150 | (286) | DPVGHYSRPDVFRLVV | | |
| 13 | WO2003000840.218 | (294) | DPAGHYSRPDVTRLLL | 81.250 | 81.250 |
| 14 | WO2003000840.262 | (295) | DPAGHYSRPDVTRLLL | 81.250 | 81.250 |
| 15 | WO2003000840.14 | (295) | DPAGHYSRPDVTRLLL | 81.250 | 81.250 |
| 16 | WO2003000840.86 | (295) | DPAGHYSRPDVTRLLL | 81.250 | 81.250 |
| 17 | WO2003000840.328 | (297) | DPVGHYSRPDVTQLIV | | |
| 18 | WO2003000840.334 | (292) | DPAGHYSRPDVTQLLL | | |
| 19 | WO2003000840.284 | (295) | DPAGHYSRPDVTRLLL | 81.250 | 81.250 |
| 20 | WO2003000840.250 | (295) | DPAGHYSRPDVTRLLL | | |
| 21 | WO2003000840.186 | (295) | DPAGHYSRPDVTRLLL | 81.250 | 81.250 |
| 22 | WO2003000840.56 | (295) | DPAGHYSRPDVTRLLL | 81.250 | 81.250 |
| 23 | WO2003000840.30 | (295) | DPAGHYSRPDVTRLLL | | |
| 24 | WO2003000840.198 | (295) | DPAGHYSRPDVTRLLL | 81.250 | 81.250 |
| 25 | WO2003000840.98 | (295) | DPAGHYSRPDVTRLLL | 81.250 | 81.250 |
| 26 | WO2003000840.168 | (295) | DPAGHYSRPDVTRLLL | 81.250 | 81.250 |

-continued

| 1 | Nitrilase | Start (1) | DPAGHYSRPDVLSLLV ↓ | % Similarity | % Identity |
|---|---|---|---|---|---|
| 27 | NitK22_RHORH | (299) | DPAGHYSRPDVLSLKI | 93.750 | 87.500 |
| 28 | WO2003000840.290 | (275) | DPVGHYSRPDVFTLHV | | |
| 29 | WO2003000840.6 | (295) | DPAGHYSRPDVTRLLF | 81.250 | 81.250 |
| 30 | WO2003000840.166 | (293) | DPAGHYSRPDVTRLLF | | |
| 31 | NitAAE0548_1 | (289) | DPAGHYSRPDITRLLI | | |
| 32 | WO2003000840.384 | (292) | DPAGHYSRPDVTRLLL | 81.250 | 81.250 |
| 33 | WO2003000840.156 | (295) | DPAGHYSRPDVTRLLL | | |
| 34 | WO2003000840.378 | (293) | DPAGHYSRPDVTQLLF | | |
| 35 | WO2003000840.178 | (288) | DPSGHYSRPDVTQLRV | | |
| 36 | WO2003000840.120 | (288) | DPTGHYSRPDVTRLVV | | |
| 37 | NitJ1_RHORH | (292) | DPVGHYSRPDVLSLNF | 81.250 | 81.250 |
| 38 | NitSD826_RHOSP | (293) | DPVGHYSRPDVLSLNF | 81.250 | 81.250 |
| 39 | NitAAO20933 | (293) | DPVGHYSRPDVLSLNF | 81.250 | 81.250 |
| 40 | Nit11216_RHORH | (293) | DPVGHYSRPDVLSLNF | 81.250 | 81.250 |
| 41 | WO2003000840.188 | (295) | DPAGHYSRPDVTRLLF | 81.250 | 81.250 |
| 42 | WO2003000840.34 | (292) | DPAGHYARPDVTRLLL | 75.000 | 75.000 |
| 43 | WO2003000840.342 | (285) | DPAGHYARPDVTRLLL | | |
| 44 | WO2003000840.348 | (277) | DPAGHYARPDVSNWKS | | |
| 45 | WO2003000840.140 | (289) | DPVGHYSRPDVTRLLF | 75.000 | 75.000 |
| 46 | WO2003000840.292 | (290) | DPVGHYSRPDVTRLLF | 75.000 | 75.000 |
| 47 | NitPA34_RHORH | (293) | DPVGHYSRPDVLSLNF | | |
| 48 | NitAAO2093_1 | (293) | DPVGHYSRPDVLSLNF | | |
| 49 | WO2003000840.268 | (291) | DPTGHYSRPDVVRLML | | |
| 50 | NitMA-1_GORTE | (293) | DPVGHYSRPDVLRLGF | 75.000 | 75.000 |
| 51 | WO2003000840.368 | (283) | RPLGHYSRPELLSLVV | | |
| 52 | WO2003000840.94 | (282) | DSVGHYSRPELLSLLI | | |
| 53 | WO2003000840.260 | (282) | DSVGHYSRPELLSLLI | | |
| 54 | WO2003000840.108 | (282) | DSVGHYSRPELLSLLI | | |
| 55 | WO2003000840.306 | (292) | DPAGHYARPDVTRLLL | | |
| 56 | WO2003000840.16 | (291) | DPAGHYARPDVTRLLF | 75.000 | 75.000 |
| 57 | WO2003000840.20 | (290) | DPVGHYSRPDVFRLLF | | |
| 58 | WO2003000840.304 | (294) | DPVGHYSRPDVHRLLL | 75.000 | 75.000 |
| 59 | WO2003000840.116 | (283) | DSVGHYSRPELLSLLI | | |
| 60 | WO2003000840.264 | (284) | DSAGHYNRPELLSLLI | | |
| 61 | WO2003000840.280 | (294) | DPVGHYSRPDVHRLLL | 75.000 | 75.000 |
| 62 | WO2003000840.54 | (290) | DVAGHYARPDVFELIV | | |
| 63 | WO2003000840.118 | (284) | DSVGHYARPELLSLLV | | |
| 64 | WO2003000840.212 | (294) | DPAGHYARPDVTRLLF | | |

-continued

| | 1 Nitrilase | Start (1) | DPAGHYSRPDVLSLLV ↓ | % Similarity | % Identity |
|---|---|---|---|---|---|
| 65 | WO2003000840.232 | (294) | DPAGHYARPDVTRLLF | | |
| 66 | WO2003000840.358 | (270) | DVAGHYSRPDIFQLHV | | |
| 67 | WO2003000840.102 | (294) | DPAGHYARPDVTRLLF | 75.000 | 75.000 |
| 68 | WO2003000840.72 | (292) | DVAGHYARPDVFELIV | | |
| 69 | Nit_KLEPN | (285) | DPTGHYSRPDVFSVSI | 75.000 | 68.750 |
| 70 | WO2003000840.162 | (282) | DSVGHYSRPELLSLLI | | |
| 71 | WO2003000840.170 | (294) | DPAGHYARPDVTRLLF | 75.000 | 75.000 |
| 72 | WO2003000840.214 | (284) | DSRGHYSRPELLSLLI | | |
| 73 | WO2003000840.210 | (284) | DSAGHYNRPELLSLMI | | |
| 74 | WO2003000840.236 | (285) | DSRGHYSRPELLSLLI | | |
| 75 | WO2003000840.18 | (284) | DSRGHYSRPELLSLLI | | |
| 76 | WO2003000840.152 | (284) | DTRGHYSRPELLSLLI | | |
| 77 | WO2003000840.44 | (284) | DTRGHYSRPELLSLLI | | |
| 78 | WO2003000840.196 | (284) | DSAGHYNRPELLSLMI | | |
| 79 | WO2003000840.238 | (284) | DSAGHYNRPELLSLMI | | |
| 80 | WO2003000840.322 | (284) | DSRGHYSRPELLSLLI | | |
| 81 | WO2003000840.82 | (284) | DSAGHYNRPELLSLMI | | |
| 82 | WO2003000840.220 | (284) | DSRGHYSRPELLSLLI | | |
| 83 | WO2003000840.224 | (285) | DSRGHYSRPELLSLLI | | |
| 84 | WO2003000840.254 | (292) | DVAGHYARPDVFQLTV | | |
| 85 | WO2003000840.192 | (285) | DVAGHYSRPDIFTLNV | | |
| 86 | WO2003000840.60 | (288) | DVAGHYSRPDVFQLCV | | |
| 87 | WO2003000840.216 | (294) | DPVGHYSRPDVYRVLF | | |
| 88 | WO2003000840.206 | (284) | DSVGHYNRPELLSLLI | | |
| 89 | WO2003000840.154 | (306) | DPIGHYSRPDVYSLQL | | |
| 90 | WO2003000840.248 | (290) | DVAGHYARPDVFELIV | | |
| 91 | WO2003000840.158 | (284) | DSRGHYSRPELLSLLI | | |
| 92 | WO2003000840.222 | (292) | DTVGHYARPDVLSLLV | | |
| 93 | WO2003000840.380 | (285) | DVAGHYSRPDIFELHV | | |
| 94 | WO2003000840.50 | (284) | DSVGHYSRPELLSLLI | | |
| 95 | WO2003000840.164 | (284) | DSVGHYNRPELLSLLI | | |
| 96 | WO2003000840.252 | (284) | DSVGHYNRPELLSLLI | | |
| 97 | WO2003000840.8 | (291) | DVAGHYARPDVFELIV | | |
| 98 | WO2003000840.4 | (287) | DVAGHYARPDIFELIV | | |
| 99 | WO2003000840.66 | (290) | DVAGHYARPDVFELIV | | |
| 100 | WO2003000840.32 | (285) | DVAGHYARPDVFELRV | | |
| 101 | WO2003000840.46 | (289) | DIAGHYARPDVFELIV | | |
| 102 | Nit2_ARATH | (301) | DSVGHYSRPDVLHLTV | 75.000 | 75.000 |

-continued

| 1 | Nitrilase | Start (1) | DPAGHYSRPDVLSLLV ↓ | % Similarity | % Identity |
|---|---|---|---|---|---|
| 103 | WO2003000840.316 | (290) | DVAGHYARPDVFELTV | | |
| 104 | WO2003000840.22 | (293) | DPVGHYARPDVLRLWF | | |
| 105 | WO2003000840.96 | (292) | DVAGHYARPDVFQLTV | | |
| 106 | WO2003000840.272 | (292) | DVAGHYARPDVFQLTV | | |
| 107 | WO2003000840.208 | (292) | DVAGHYARPDVFQLTV | | |
| 108 | WO2003000840.194 | (292) | DVAGHYARPDVFQLTV | | |
| 109 | WO2003000840.42 | (292) | DVAGHYARPDVFQLTV | | |
| 110 | WO2003000840.240 | (292) | DVAGHYARPDVFQLTV | | |
| 111 | WO2003000840.242 | (293) | DVAGHYARPDVFELTV | | |
| 112 | WO2003000840.318 | (284) | DSRGHYARPELLSLLI | | |
| 113 | WO2003000840.174 | (284) | DSRGHYNRPELLSLLI | | |
| 114 | WO2003000840.308 | (289) | DVAGHYGRPDVFHLTV | | |
| 115 | WO2003000840.234 | (285) | DSRGHYNRPELLSLLI | | |
| 116 | WO2003000840.330 | (282) | DSVGHYSRPELLSVLI | | |
| 117 | WO2003000840.352 | (275) | DVAGHYARPDIFELEI | | |
| 118 | WO2003000840.110 | (282) | DSVGHYSRPELLSLLI | | |
| 119 | WO2003000840.300 | (282) | DASGHYSRPELLSLQI | | |
| 120 | Nit4_TOBAC | (312) | DVVGHYARPEVLSLIV | 81.250 | 68.750 |
| 121 | WO2003000840.126 | (285) | DSVGHYARPELLSLLV | | |
| 122 | WO2003000840.202 | (287) | DVSGHYSRPDVFSFGV | | |
| 123 | WO2003000840.200 | (289) | DVAGHYARPDVFELTV | | |
| 124 | WO2003000840.288 | (285) | DVAGHYSRPDLFELEI | | |
| 125 | WO2003000840.286 | (287) | DVTGHYSRPDVFSYEI | | |
| 126 | WO2003000840.64 | (290) | DVTGHYSRPDVLRLHF | | |
| 127 | WO2003000840.246 | (288) | DVAGHYARPDVFQLTV | | |
| 128 | WO2003000840.258 | (285) | DVAGHYARPDIFELHV | | |
| 129 | WO2003000840.256 | (290) | DVAGHYARPDVFELTV | | |
| 130 | WO2003000840.160 | (289) | DVTGHYARPDVFDLTV | | |
| 131 | WO2003000840.124 | (287) | DVAGHYARPDVFRLTV | | |
| 132 | WO2003000840.172 | (290) | DVAGHYARPDVFQLTV | | |
| 133 | WO2003000840.312 | (284) | DSVGHYSRPELLSLAI | | |
| 134 | WO2003000840.136 | (284) | DSVGHYSRPELLSLAI | | |
| 135 | WO2003000840.180 | (283) | DVSGHYSRPDVFTFEV | | |
| 136 | WO2003000840.78 | (290) | DVAGHYARPDIFELIV | | |
| 137 | WO2003000840.28 | (290) | DVAGHYARPDIFELIV | | |
| 138 | WO2003000840.278 | (290) | DVAGHYARPDIFELIV | | |
| 139 | WO2003000840.270 | (295) | DPSGHYARGDVVRLMV | | |
| 140 | WO2003000840.106 | (281) | DGRGHYSRPEILSLNI | | |

-continued

| 1 | Nitrilase | Start (1) | DPAGHYSRPDVLSLLV ↓ | % Similarity | % Identity |
|---|---|---|---|---|---|
| 141 | WO2003000840.92 | (285) | DASGHYARPDVFKLHV | | |
| 142 | WO2003000840.332 | (295) | DPAGHYARADALALMH | 68.750 | 62.500 |
| 143 | WO2003000840.10 | (287) | DVVGHYSRPDVFRLEV | | |
| 144 | WO2003000840.176 | (275) | DVGGHYSRPDIFQLHV | | |
| 145 | WO2003000840.190 | (295) | DPTGHYARGDVVRLMV | | |
| 146 | Nit_BRAJA | (295) | DPTGHYARGDVVRLMV | 68.750 | 62.500 |
| 147 | WO2003000840.24 | (284) | DTRGHYSRPELLSLTI | | |
| 148 | WO2003000840.204 | (291) | DVAGHYGRPDVFRLSV | | |
| 149 | WO2003000840.84 | (290) | DSVGHYARPELLSLLI | | |
| 150 | WO2003000840.80 | (292) | DVGGHYARPDVFELVV | | |
| 151 | WO2003000840.324 | (287) | DVAGHYGRPDIFCLQV | 68.750 | 62.500 |
| 152 | WO2003000840.74 | (290) | DAAGHYARPDIFQLTV | | |
| 153 | WO2003000840.52 | (285) | DTAGHYDRPDLASA-- | | |
| 154 | WO2003000840.76 | (285) | DSRGHYSRPELLSLLI | | |
| 155 | WO2003000840.230 | (294) | DTDGHYSRPDVFELRV | | |
| 156 | WO2003000840.376 | (285) | DATGHYARPDVFQLHV | | |
| 157 | WO2003000840.88 | (287) | DAAGHYARPDVFQLTV | | |
| 158 | Nit4_ORYSA | (318) | DVVGHYARPEVLSLVV | 75.000 | 68.750 |
| 159 | WO2003000840.336 | (288) | DSVGHYARPELLSLLL | | |
| 160 | WO2003000840.338 | (286) | SMCGHYSRPDVFSFSV | | |
| 161 | WO2003000840.130 | (284) | DSVGHYARPELLSLAI | | |
| 162 | WO2003000840.132 | (284) | DSVGHYARPELLSLAI | | |
| 163 | WO2003000840.38 | (301) | DTSGHYSRPDIFRLEI | | |
| 164 | WO2003000840.100 | (284) | DSVGHYARPELLSLAI | | |
| 165 | WO2003000840.282 | (284) | DVSGHYGRPDVFHLQI | | |
| 166 | Nit285_COMTE | (297) | DPAGHYSTPGFLSLTF | 68.750 | 68.750 |
| 167 | WO2003000840.40 | (291) | DASGHYNRPELLSLHI | | |
| 168 | WO2003000840.294 | (291) | DASGHYNRPELLSLHI | | |
| 169 | CYHY_GIBBA | (297) | DPAGHYMRPDLIRLLV | | |
| 170 | Nit2_BRANA | (309) | DVVGHYSRPDIFNLRV | 68.750 | 62.500 |
| 171 | WO2003000840.226 | (282) | DSRGLYSRPELLSLLI | | |
| 172 | WO2003000840.228 | (284) | DSVGHYARPELLSLAI | | |
| 173 | Nit1_ARATH | (308) | DSVGYYSRPDVLHLTV | 75.000 | 68.750 |
| 174 | WO2003000840.184 | (284) | DSVGHYARPELLSLRL | | |
| 175 | WO2003000840.274 | (285) | DCVGHYSRPDLLKLQL | | |
| 176 | WO2003000840.104 | (280) | DVGGHYSRPDVFRFEV | | |
| 177 | WO2003000840.382 | (280) | DVGGHYSRPDVFRFEV | | |
| 178 | WO2003000840.128 | (284) | DSVGHYARPELLSLHI | | |

| 1 | Nitrilase | Start (1) | DPAGHYSRPDVLSLLV ↓ | % Similarity | % Identity |
|---|---|---|---|---|---|
| 179 | WO2003000840.134 | (284) | DSVGHYARPELLSLRI | | |
| 180 | Nit_NECHA | (296) | DFAGHYMRPDLIRLLV | 75.000 | 68.750 |
| 181 | WO2003000840.68 | (285) | DVVGHYARPDLFDLHV | | |
| 182 | WO2003000840.298 | (291) | DVGGHYSRPDIFQLRV | | |
| 183 | WO2003000840.320 | (284) | DSVGHYARPELLSLNA | 62.500 | 56.250 |
| 184 | Nit3_ARATH | (308) | DVVGHYSKPDIFNLTV | 68.750 | 56.250 |
| 185 | CYHY_GLOSO | (296) | DFAGHYMRDLIRLLV | 75.000 | 68.750 |
| 186 | WO2003000840.314 | (279) | DVGGSYSRPDLLQLMI | 68.750 | 56.250 |
| 187 | WO2003000840.374 | (291) | DLGGHYSRPDIFQLRV | 68.750 | 62.500 |
| 188 | WO2003000840.90 | (287) | DVTGHYARPDVFRYEI | 56.250 | 50.000 |
| 189 | CYHY_LEPMA | (296) | DFSGHYMRPDLIRLLV | 68.750 | 62.500 |
| 190 | WO2003000840.244 | (290) | DVTGHYSRPDLFHLEF | 56.250 | 56.250 |
| 191 | WO2003000840.112 | (282) | DSVGHYARPELLHLVH | 56.250 | 56.250 |
| 192 | WO2003000840.182 | (282) | DSVGHYARPELLHLVH | 56.250 | 56.250 |
| 193 | WO2003000840.326 | (284) | DSVGHYARPELLSLQL | 62.500 | 56.250 |
| 194 | WO2003000840.142 | (288) | DSKGHYARPEILKLGV | 68.750 | 56.250 |
| 195 | NitJM3_ALCFA | (291) | DPVGHYSKPEATRLVL | 62.500 | 50.000 |
| 196 | Nit1650_ALCFA | (291) | DPVGHYSKPEATRLVL | 62.500 | 50.000 |
| 197 | Nit8750_ALCFA | (291) | DPVGHYSKPEATRLVL | 62.500 | 50.000 |
| 198 | WO2003000840.148 | (294) | DSKGHYARPEVLRLAV | 68.750 | 62.500 |
| 199 | NitOxB1_BACSU | (287) | DSAGHYSTPGFLSLSF | 62.500 | 62.500 |
| 200 | WO2003000840.144 | (288) | DSAGHYARPEVVQLRD | 62.500 | 56.250 |
| 201 | WO2003000840.302 | (288) | DAAGHYHRPDLFHFAM | 50.000 | 50.000 |
| 202 | WO2003000840.70 | (285) | DSVGHYSRAEVLDGGV | 62.500 | 56.250 |
| 203 | WO2003000840.276 | (290) | DVSGHYQRRDVFSFDV | 56.250 | 56.250 |
| 204 | WO2003000840.138 | (282) | DASGHYQPPEILSFTL | 56.250 | 43.750 |
| 205 | WO2003000840.26 | (291) | DVTGHYARAELFDLNV | 50.000 | 43.750 |
| 206 | Nit_PSEST | (280) | DPVGHYSNQ-SLSMNF | 60.000 | 53.333 |
| 207 | WO2003000840.122 | (311) | DSLGHYSRWDIAQLAI | 62.500 | 50.000 |
| 208 | WO2003000840.296 | (317) | DSLGHYARWDLVNLTT | 43.750 | 43.750 |
| | Consensus | (395) | D GHYSRPDV LLV | | |

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein, the word "or" means any one member of a particular list and also includes any combination of members of that list.

The term "nucleic acid" refers to deoxyribonucleotides or ribonucleotides and polymers or hybrids thereof in either single- or double-stranded, sense or antisense form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiralmethyl phosphonates, 2-O-methyl ribonucleotides, peptide-nucleic acids (PNAs), and the like.

Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used interchangeably herein with "gene", "cDNA", "mRNA", "oligonucleotide," and "polynucleotide".

The phrase "a nucleic acid sequence" as used herein refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid which is transcribed and translated in a sequence-specific manner to produce into a particular polypeptide or protein when placed under the control of appropriate regulatory sequences. The coding region is said to encode such a polypeptide or protein.

The term "gene" refers to a coding region operably joined to appropriate regulatory sequences capable of regulating the expression of the polypeptide in some manner. A gene includes untranslated regulatory regions of DNA (e.g., promoters, enhancers, repressors, etc.) preceding (upstream) and following (downstream) the coding region (open reading frame, ORF) as well as, where applicable, intervening sequences (i.e., introns) between individual coding regions (i.e., exons).

The terms "polypeptide", "peptide", "oligopeptide", "polypeptide", "gene product", "expression product" and "protein" are used interchangeably herein to refer to a polymer or oligomer of consecutive amino acid residues. The terms apply to amino acid polymers in which one or more amino acid residue is an analog or mimetic of a corresponding naturally occurring amino acid, as well as to naturally occurring amino acid polymers. In addition, as used herein, the term "polypeptide" refers to amino acids joined to each other by peptide bonds or modified peptide bonds and may contain modified amino acids other than the 20 gene-encoded amino acids. The polypeptides can be modified by either natural processes, such as post-translational processing, or by chemical modification techniques which are well known in the art.

Modifications can occur anywhere in the polypeptide, including the peptide backbone, the amino acid side-chains and the amino or carboxyl termini. It will be appreciated that the same type of modification can be present in the same or varying degrees at several sites in a given polypeptide. Also a given polypeptide can have many types of modifications. Modifications include, without limitation, acetylation, acylation, ADP-ribosylation, amidation, covalent cross-linking or cyclization, covalent attachment of flavin or of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, γ-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins-Structure and Molecular Properties 2nd Ed., Creighton T E, Freeman W H and Company, New York (1993); Posttranslational Covalent Modification of Proteins, Johnson B C, Ed., Academic Press, New York, pp. 1-12 (1983)). Modifications may also include N- or C-terminal fusions to short peptides ("tags"), like e.g., 6×HIS-tag) or larger domains (e.g., maltose-binding protein, GST-protein, thioredoxin).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group (e.g., homoserine, norleucine, methionine sulfoxide, methionine methyl sulfonium).

As used herein, the term "amino acid sequence" refers to a list of abbreviations, letters, characters or words representing amino acid residues. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The abbreviations used herein are conventional one letter codes for the amino acids: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid (see L. Stryer, Biochemistry, 1988, W. H. Freeman and Company, New York. The letter "X" as used herein within an amino acid sequence can stand for any amino acid residue.

The term "isolated" as used herein means that a material has been removed from its original environment. For example, a naturally-occurring polynucleotide or polypeptide present in a living animal is not isolated, but the same polynucleotide or polypeptide, separated from some or all of the coexisting materials in the natural system, is isolated. Such polynucleotides can be part of a vector and/or such polynucleotides or polypeptides could be part of a composition, and would be isolated in that such a vector or composition is not part of its original environment.

The term "natural" or of "natural origin" means in this context that an organism, polypeptide a nucleic acid sequence available in at least one organism which is not changed, mutated, or otherwise manipulated by man.

The term "recombinant" with respect to, for example, a nucleic acid sequence (or a organism, expression cassette or vector comprising said nucleic acid sequence) refers to all those constructs originating by recombinant methods in which either a) said nucleic acid sequence, or
b) a genetic control sequence linked operably to said nucleic acid sequence a), for example a promoter, or
c) (a) and (b)

is not located in its natural genetic environment or has been modified by recombinant methods, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the nucleic acid sequence is preferably retained, at least in part. The environment flanks the nucleic acid sequence at least at one side and has a sequence of at least 50 bp, preferably at least 500 bp, especially preferably at least 1000 bp, very especially preferably at least 5000 bp, in length. A naturally occurring expression cassette—for example the naturally occurring combination of a promoter with the corresponding gene—becomes a recombinant expression cassette when it is modified by non-natural, synthetic "artificial" methods such as, for example, mutagenization. Such methods have been described (U.S. Pat. No. 5,565,350; WO 00/15815; also see above). Preferably, the term "recombinant" with respect to nucleic acids as used herein means that the nucleic acid is covalently joined and adjacent to a nucleic acid to which it is not adjacent in its natural environment.

"Recombinant" polypeptides or proteins refer to polypeptides or proteins produced by recombinant DNA techniques, i.e., produced from cells transformed by an exogenous recombinant DNA construct encoding the desired polypeptide or protein.

Recombinant nucleic acids and polypeptide may also comprise molecules which as such does not exist in nature but are modified, changed, mutated or otherwise manipulated by man. A "recombinant polypeptide" is a non-naturally occurring polypeptide that differs in sequence from a naturally occurring polypeptide by at least one amino acid residue. Preferred methods for producing said recombinant polypeptide and/or nucleic acid may comprise directed or non-directed mutagenesis, DNA shuffling or other methods of recursive recombination. an especially preferred method to obtain such recombinant molecules may involve gene shuffling. Shuffling methods are known in the art and, for example, described in WO 01/12817 and in the references cited therein. employed. The term "shuffling" is used herein to indicate recombination between nonidentical sequences, in some embodiments shuffling may include crossover via homologous recombination or via non-homologous recombination, such as via cre/lox and/or flp/frt systems. Shuffling can be carried out by employing a variety of different formats, including, for example, in vitro and in vivo shuffling formats, in silico shuffling formats, shuffling formats that utilize either double-stranded or single-stranded templates, primer-based shuffling formats, nucleic acid fragmentation-based shuffling formats, oligonucleotide mediated shuffling formats, all of which are based on recombination events between non identical sequences and are described in more detail or reference herein below, as well as other similar recombination-based formats.

"Synthetic" polypeptides or proteins are those prepared by chemical synthesis (e.g., solid-phase peptide synthesis). Chemical peptide synthesis is well known in the art (see, e.g., Merrifield (1963), Am. Chem. Soc. 85: 2149-2154; Geysen et al. (1984) Proc Natl Acad Sci USA 81:3998) and synthesis kits and automated peptide synthesizer are commercially available (e.g., Cambridge Research Biochemicals, Cleveland, United Kingdom; Model 431A synthesizer from Applied Biosystems, Inc., Foster City, Calif.). Such equipment provides ready access to the peptides of the invention, either by direct synthesis or by synthesis of a series of fragments that can be coupled using other known techniques.

The term "identity" as used herein with respect to two nucleic acid sequences is understood as meaning the identity calculated with the aid of the program algorithm GAP (Wisconsin Package Version 10.0, University of Wisconsin, Genetics Computer Group (GCG), Madison, USA; Altschul et al. (1997) Nucleic Acids Res. 25:3389 et seq.), setting the following parameters:

| Gap weight: 50 | Length weight: 3 |
| Average match: 10 | Average mismatch: 0 |

For example a sequence which has at least 60% homology with sequence SEQ ID NO-1 at the nucleic acid level is understood as meaning a sequence which, upon comparison with the sequence SEQ ID NO: 1 by the above program algorithm with the above parameter set, has at least 60% identity. Where appropriate the scoring matrix blosum62 was used.

The term "identity" as used herein with respect to two polypeptides is understood as meaning the identity calculated with the aid of the program algorithm GAP (Wisconsin Package Version 10.0, University of Wisconsin, Genetics Computer Group (GCG), Madison, USA), setting the following parameters:

| Gap weight: 8 | Length weight: 2 |
| Average match: 2,912 | Average mismatch: −2,003 |

For example a sequence which has at least 60% homology with sequence SEQ ID NO: 2 at the protein level is understood as meaning a sequence which, upon comparison with the sequence SEQ ID NO: 2 by the above program algorithm with the above parameter set, has at least 60% identity.

As used herein, "homology" has the same meaning as "identity" in the context of nucleotide sequences. However, with respect to amino acid sequences, "homology" includes the percentage of identical and conservative amino acid substitutions. Percentages of homology can be calculated according to the algorithms of Smith and Waterman (1981) Adv Appl Math 2:482 and Needleman & Wunsch (1970) J Mol Biol 48:443-453 using the scoring matrix blosum62.

As used herein in the context of two or more nucleic acid sequences, two sequences are "substantially identical" when they have at least 99.5% nucleotide identity, when compared and aligned for maximum correspondence, as measured using the known sequence comparison algorithms described above. In addition, for purposes of determining whether sequences are substantially identical, synonymous codons in a coding region may be treated as identical to account for the degeneracy of the genetic code. Typically, the region for determination of substantial identity must span at least about 20 residues, and most commonly the sequences are substantially identical over at least about 25-200 residues.

As used herein in the context of two or more amino acid sequences, two sequences are "substantially identical" when they have at least 99.5% identity, when compared and aligned for maximum correspondence, as measured using the known sequence comparison algorithms described above. In addition, for purposes of determining whether sequences are substantially identical, conservative amino acid substitutions may be treated as identical if the polypeptide substantially retains its biological function.

"Hybridization" refers to the process by which a nucleic acid strand joins with a complementary strand through hydrogen bonding at complementary bases. Hybridization assays can be sensitive and selective so that a particular sequence of interest can be identified even in samples in which it is present at low concentrations. Stringent conditions are defined by concentrations of salt or formamide in the pre-hybridization and hybridization solutions, and/or by the hybridization temperature, and are well known in the art. Stringency can be increased by reducing the concentration of salt, increasing the concentration of form amide, or raising the hybridization temperature. The term "standard conditions" as used herein means, for example depending on the nucleic acid, temperatures between 42 and 58° C. in an aqueous buffer solution with a concentration between 0.1 and 5×SSC (1×SSC=0.15 M NaCl, 15 mM sodium citrate, pH 7.2) or additionally in the presence of 50% formamide, such as, for example, 42° C. in 5×SSC, 50% formamide. The hybridization conditions for DNA:DNA hybrids preferably comprise 0.1×SSC and temperatures between about 20° C. and 45° C., preferably between about 30° C. and 45° C. The hybridization conditions for DNA:RNA hybrids preferably comprise 0.1×SSC and temperatures between about 30° C. and 55° C., preferably between about 45° C. and 55° C. These temperatures stated for the hybridization are melting temperatures calculated by way of example for a nucleic acid with a length of about 100 nucleotides and a G+C content of 50% in the absence of form amide. The experimental conditions for the DNA hybridization are described in relevant textbooks of genetics such as, for example, Sambrook et al., "Molecular Cloning", Cold Spring Harbor Laboratory, 1989, and can be calculated by formulae known to the skilled worker, for example depending on the length of the nucleic acids, the nature of the hybrids or the G+C content. The skilled worker can find further information on hybridization in the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford. In particular, as used herein, "stringent hybridization conditions" include 42° C. in 50% formamide, 5×SSPE, 0.3% SDS, and 200 ng/ml sheared and denatured salmon sperm DNA, and equivalents thereof. Variations on the above ranges and conditions are well known in the art.

The term "variant" as used herein refers to polynucleotides or polypeptides of the invention modified at one or more nucleotides or amino acid residues (respectively) and wherein the encoded polypeptide or polypeptide retains nitrilase activity. Variants can be produced by any number of means including, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site-saturated mutagenesis or any combination thereof.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-bases and/or deoxyinosine residues (Batzer et al. (1991) Nucleic Acid Res 19:5081; Ohtsuka et al. (1985) J Biol Chem 260:2605-2608; Rossolini et al. (1994) Mol Cell Probes 8:91-98). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations", which are one species of conservatively modified variations. Every nucleic acid sequence recited herein that encodes a polypeptide also describes every possible silent variation of the nucleic acid. One of skill will recognize that each codon in a nucleic acid (except AUG, which, along with GUG in some organisms, is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alter, add or delete a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "nitrilase" as used herein includes all polypeptides which exhibit nitrilase activity.

The term "nitrilase activity" means in general the ability to hydrolyze nitriles into their corresponding carboxylic acids and ammonia. Preferably "nitrilase activity" means the property to catalyze the addition of two molar equivalents water to a nitrile group resulting in the formation of the corresponding carbonic acid:

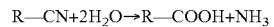

Preferably, the term "nitrilase" comprises enzymes of the EC-classes 3.5.5.1 (nitrilases), 3.5.5.2 (ricinin nitrilases), 3.5.5.4 (cyanoalanine nitrilases), 3.5.5.5 (arylaceto nitrilases), 3.5.5.6 (bromoxynil nitrilases), and 3.5.5.7 (aliphatic nitrilases). More, preferred are arylaceto nitrilases (EC 3.5.5.5).

A nitrilase may comprise conserved amino acid residues or motifs, which are typically conserved among enzymes with nitrilase activity. These conserved residues can be identified by e.g., an alignment of the sequences of several nitrilases. Conserved residues comprise e.g., the residue cysteine in position 163 of the sequence of wild-type *Alcaligenes faecalis* nitrilase as described by SEQ ID NO: 2, which is involved in the reaction mechanism of the nitrilases (Kobayashi et al. (1993) Proc Natl Acad Sci USA 90:247-251). Three regions of conserved motifs were identified within the nitrilase polypeptides. These correspond to the catalytic triad (E-K-C) present in nitrilase enzymes (Pace & Brenner (2001) Genome Biology 2(1):1-9):
1. fPEaf
2. hR̄K̄l.pT
3. l.C̄W̄En.p Ūppēr case letters indicate 90% or greater consensus among the nitrilases, while lower case letters indicate 50% or greater consensus. A dot in a box indicates a residue which is not conserved. Preferably, the following residues (those that are underlined) are completely conserved among all of the identified nitrilases: the third amino acid in the first motif or region (E, glutamate); the second residue in the second motif (R, arginine); the third residue in the second motif (K, lysine); the third residue in the third motif (C, cysteine); and the fifth residue in the third motif (E, glutamate).

Within this invention the reference sequence is the nitrilase from *Alcaligenes faecalis* nitrilase as described by SEQ ID NO: 2. All definitions, indications and descriptions of particular amino acid or nucleic acid positions are made compared to the primary sequence of said sequence and can be transferred by the person skilled in the art to other nitrilases utilizing e.g., a sequence alignment as depicted in FIG. 4 or 5.

The nitrilase can be of natural, synthetic, or recombinant origin. Numerous organisms are known in the art which naturally express nitrilases. Preferably the nitrilase to be modified according this invention is selected from a nitrilase of bacterial, yeast, fungal, vegetable or animal origin. More preferably the nitrilase is from an microorganism, most preferably of bacterial origin. A nitrilase can also be isolated from environmental sources like e.g., soil or marine material without detailed identification of the organism.

Numerous nitrilases and their sequences are known in the art. These nitrilases include but are not limited to nitrilases from *Acidovorax facilis* 72W (Gavagan J E et al. (1999) Appl Microbiol Biotechnol 52:654-659), *Acinetobacter* sp. AK 226 (Yamamoto K und Komatsu K (1991) Agric Biol Chem 55(6):1459-1466), *Acinetobacter* sp. RFB1 (Finnegan I et al. (1991) Appl Microbiol Biotechnol 36:142-144), *Alcaligenes faecalis* ATCC 8750 (Yamamoto K et al. (1991) Appl Environ Microbiol 57(10):3028-3032), *Alcaligenes faecalis* JM3 (Nagasawa T et al. (1990) Eur J Biochem 194:765-772), *Arabidopsis thaliana* (NIT1/NIT2/NIT3; Vorwerk S et al. (2001) Planta 212:508-516), *Arthrobacter* sp. J-1 (Bandyopadhyay A K et al. (1986) Appl Environ Microbiol 51(2):302-306), *Bacillus pallidus* Dac521 (Cramp R et al. (1997) Microbiology 143:2313-2320), *Comamonas* sp. NI1 (Cerbelaud E et al. (1996) Ind Chem Libr 8:189-200), *Comamonas testosteroni* sp. (Levy-Schil S et al. (1995) Gene 161:15-20), *Fusarium oxysporum* f. sp. *melonis* (Goldlust A und Bohak Z (1989) Biotechnol Appl Biochem 11:581-601), *Fusarium solani* (Harper B H (1977) Biochem J 167:685-692), *Klebsiella ozaenae* (McBride K E et al. (1986) Appl Environ Microbiol 52(2):325-330), *Pseudomonas fluoreszenz* DSM 7155 (Layh N et al. (1998) J Mol Catal B: Enzym 5:467-474), *Pseudomonas* sp. (Layh N et al. (1992) Arch Mircobiol 158:405-411), Nitrilase aus *Pseudomonas* sp. (S1) (Dhillon J et al. (1999) Can J Microbiol 45: 811-815), Nitrilase from *Pseudomonas* sp. 13 (Yanase H et al. (1982) Agric Biol Chem 46:2925), *Rhodococcus rhodochrous* J1 (Kobayashi M et al. (1989) Eur J Biochem 182:349-356), *Rhodococcus rhodochrous* K22 (Kobayashi M et al. (1990) J Bacteriol 172(9):4807-4815), *Rhodococcus rhodochrous* NCIB 11215 (Harper B H (1985) Int J Biochem 17(6):677-683), *Rhodococcus rhodochrous* NCIB 11216 (Harper B H (1977) Biochem J 165:309-319), *Rhodococcus rhodochrous* PA34 (Bhalla T C et al. (1992) Appl Microbiol Biotechnol 37:184-190), *Rhodococcus* sp. ATCC 39484 (Stevenson D E et al. (1992) Biotechnol Appl Biochem 15:283-302), and nitrilases isolated from environmental sources and described in e.g., WO 03/000840, WO 01/48175, and WO 02/279079.

An isolated polypeptide of the invention encodes an enzyme with nitrilase activity, which comprise comprise at least one sequence selected from the group of sequences comprising a)     (K/R/H)XXXDXXGX(X*),     (SEQ ID NO: 24)

b) a sequence having a homology of at least 50%, preferably at least 60%, more preferably at least 70% or 80%, most preferably at least 90% or 95% with respect to a nitrilase consensus sequence sequence selected from the group of sequences comprising i)     KAINDPVGH(X*),     (SEQ ID NO: 9)

ii)     GH(X*)SRPDV,     (SEQ ID NO: 10)

and c) a sequence having a homology of at least 35%, preferably at least 40%, more preferably at least 60% or 80%, most preferably at least 90% or 95% with respect to a nitrilase consensus sequence sequence selected from the group of sequences comprising i)     DP(A/V)GH(X*)SRPDV(L/T)(S/R)L,     (SEQ ID NO: 11)
and ii)     DPAGH(X*)SRPDVLSLLV,     (SEQ ID NO: 12)

provided that in said sequence comprised in said enzyme with nitrilase activity said residue X* represents an amino acid residue which is not tyrosine, and wherein X* is localized at a position corresponding to position 296 in wild-type *Alcaligenes faecalis* nitrilase as described by SEQ ID NO: 2.

Especially preferably, a nitrilase of the invention comprises a sequence selected from the group consisting of a)     (K/R)XXXDXXG(H/Y/S)(X*),     (SEQ ID NO: 13)

b)     KXXXDXXGX(X*),     (SEQ ID NO: 25)

c)     KAINDPVGH(X*),     (SEQ ID NO: 9)

d)     GH(X*)SRPDV,     (SEQ ID NO: 10)

e)     DP(A/V)GH(X*)SRPDV(L/T)(S/R)L,     (SEQ ID NO: 11)
and f)     DPAGH(X*)SRPDVLSLLV,     (SEQ ID NO: 12)

wherein X stands for any amino acid and provided that in said sequence comprised in said nitrilase of the invention X* represents an amino acid residue which is not tyrosine, and wherein X* is localized at a position corresponding to position 296 in wild-type *Alcaligenes faecalis* nitrilase as described by SEQ ID NO: 2. Preferably, a nitrilase of the invention comprises a sequence selected from the group consisting of a)     KAINDPVGH(X*),     (SEQ ID NO: 9)

b)     DP(A/V)GH(X*)SRPDV(L/T)(S/R)L,     (SEQ ID NO: 11)
or, most preferably,

DPAGH(X*)SRPDVLSLLV,     (SEQ ID NO: 12)

In an preferred embodiment the residue X* is selected from the group consisting of cysteine, alanine, asparagine, glycine, serine, phenylalanine, and threonine. More preferred, the residue X* is selected from the group consisting of alanine, cysteine, asparagine, and serine. Most preferred, the residue X* is selected from the group consisting of alanine, and cysteine.

In a preferred embodiment, a nitrilase of the invention is further characterized as being described by a polypeptide sequence selected from the group consisting of:
a) polypeptide molecules comprising an amino acid sequence which is at least 60%, preferably 80%, more preferably 90%, most preferably 95% identical to the amino acid sequence of SEQ ID NO: 2, 4, 6, or 8; and
b) polypeptide molecules comprising a fragment of at least 20 consecutive amino acids, preferably 50 consecutive amino acids of at least one of the sequences described by SEQ ID NO: 2, 4, 6, or 8.

A nitrilase known in the art can be mutated or converted to a nitrilase of the invention by numerous methods known to the person skilled in the art. Mutagenesis methods may be random or directed and may include, for example, those described in WO 98/42727; site-directed mutagenesis (Ling et al. (1997) Anal Biochem. 254(2):157-78; Dale et al. (1996) Methods Mol Biol 57:369-74; Smith (1985) Ann Rev Genet 19:423-462; Botstein & Shortle (1985) Science 229:1193-1201; Carter (1986) Biochem J 237:1-7; Kunkel (1987) "The efficiency of oligonucleotide directed mutagenesis" Nucleic Acids & Molecular Biology, Eckstein F and Lilley D M J eds, Springer Verlag, Berlin); mutagenesis using uracil containing templates (Kunkel (1985) Proc Natl Acad Sci USA 82:488-492; Kunkel T A et al. (1987) Methods in Enzymol 154, 367-382; Bass S V et al. (1988) Science 242:240-245); oligonucleotide-directed mutagenesis (for review see, Smith (1985) Ann Rev Genet 19:423-462; Botstein & Shortle (1985) Science 229:1193-1201; Carter (1986) Biochem J 237:1-7, Zoller & Smith (1982) Nucleic Acids Res 10:6487-6500, Zoller & Smith (1983) Methods in Enzymol 100, 468-500, Zoller & Smith (1987) Methods in Enzymol. 154, 329-350); phosphothioate-modified DNA mutagenesis (Taylor et al. (1985) Nucl Acids Res 13: 8749-8764; Taylor et al. (1985) Nucl Acids Res 13:8765-8787 (1985); Nakamaye and Eckstein (1986) Nucl Acids Res 14:9679-9698; Sayers et al. (1988) Nucl Acids Res 16:791-802; Sayers et al. (1988) Nucl Acids Res 16:803-814); mutagenesis using gapped duplex DNA (Kramer et al. (1984) Nucl Acids Res 12:9441-9456; Kramer and Fritz (1987) Methods in Enzymol 154:350-367; Kramer et al. (1988) Nucl Acids Res. 16:7207; Fritz et al. (1988) Nucl Acids Res 16:6987-6999.

Modifications of a nitrilase sequence may be achieved, for example, by mutagenesis on the sequence encoding an enzyme of natural origin (Skandalis et al. (1997) Chemistry & Biology 4:8889-898; Crameri et al. (1998) Nature 391:288-291). The mutagenesis may include mutagenic chemicals (Singer and Fraenkel-Conrat (1969) Prog Nucl Acid Res Mol Biol 9:1-29), mutagenesis by error-prone PCR (Leung et al. (1989) Technique 1:11-15), by combinative PCR (Crameri et al. (1998) above mentioned; Shao et al.(1998) Nucleic Acids Res 26:681-683), or by directed mutagenesis (Directed Mutagenesis: A Practical Approach (1991) McPherson M J, ed. IRL PRESS), etc. In addition, a nitrilase to be utilized within the invention may be obtained by screening banks of DNA, in particular cDNA or genomic DNA of various sources, in particular of banks of DNA obtained by recombinations and random changes of nitrilases, by directed molecular evolution or screening of DNA libraries of ground or other biotopes.

Additional suitable methods include point mismatch repair (Kramer et al. (1984) Cell 38: 879-887), mutagenesis using repair deficient host strains (Carter et al. (1985) Nucl Acids Res 13: 4431-4443 (1985); Carter (1987) Methods in Enzymol. 154:382-403), deletion mutagenesis (Eghtedarzadeh & Henikoff (1986) Nucl Acids Res 14:5115), restriction-selection and restriction-purification (Wells et al. (1986) Phil Trans R Soc Lond A317: 415-423), mutagenesis by total gene synthesis (Nambiar et al. (1984) Science 223:1299-1301; Sakamar & Khorana (1988) Nucl Acids Res 14:6361-6372; Wells et al. (1985) Gene 34: 315-323 (1985); Grundstrom et al. (1985) Nucl Acids Res. 13:3305-3316), double-strand break repair (Mandecki (1986) Proc Natl Acad Sci. USA 83:7177-7181). Additional details on many of the above methods can be found in Methods in Enzymology, Vol. 154, which also describes useful controls for trouble-shooting problems with various mutagenesis methods. Furthermore, mutations can be introduced by applying other random mutagenesis methods (e.g., passage through mutagenic bacterial strains, and the like).

Kits for mutagenesis are commercially available. For example, kits are available from, e.g., Stratagene, Bio-Rad, Roche, Clontech Laboratories, Life Technologies (Gibco BRL), New England Biolabs, Pharmacia Biotech, and Promega Corp.

Beside the change at the position corresponding to position 296 in wild-type *Alcaligenes faecalis* nitrilase as described by SEQ ID NO: 2 by another amino acid additional changes can be made to a nitrilase to achieve new or modified properties. This may be realized by a procedure known in the art as "directed evolution". It combines methods of materially changing the enzyme while selecting in an iterative way the variations which present improved properties (Arnold & Volkov (1999) Current Opin Chem Biol 3:54-59; Kuchner and Arnold (1997) Tibtech 15:523-530). For example, methods like the methods described in WO 01/12817 and the methods cited therein may be employed. Preferred methods for obtaining modified nitrilase may comprise directed or non-directed mutagenesis, DNA shuffling or other methods of recursive recombination. In a preferred embodiment, the shuffling of a "family" of nucleic acids (e.g., nucleic acid sequences encoding for nitrilases from different species) is used to create the library of recombinant polynucleotides. When a family of nucleic acids is shuffled, nucleic acids that encode homologous polypeptides from different strains, species, or gene families or portions thereof, are used as the different forms of the nucleic acids.

The invention may involve creating recombinant libraries of polynucleotides encoding nitrilases that are then screened to identify those library members that encode a nitrilase that exhibits a desired property, e.g., enhanced enzymatic activity, stereospecificity, regiospecificity and enantiospecificity, reduced susceptibility to inhibitors, processing stability (e.g., solvent stability, pH stability, thermal stability, etc.), and the like. The recombinant libraries can be created using any of various methods including but not limited to shuffling protocols as described for example in WO 01/12817 and the references cited therein.

The term "substrate acceptance" as used herein means the capability of a nitrilase to convert a specific nitrile substrate. Preferably, substrate acceptance is measured by the nitrilase activity of the enzyme.

The term "broader substrate acceptance" with regard to a certain nitrilase of the invention means that said certain nitrilase exhibits a higher nitrilase activity for at least one nitrilase substrate in comparison with a nitrilase encoded by the same amino acid sequence than said certain nitrilase but comprising a tyrosine at a position corresponding to position 296 in wild-type *Alcaligenes faecalis* nitrilase as described by SEQ ID NO: 2. Preferably said activity is increased by at least 10%, preferably 20%, more preferably 50%, most preferably 100% or higher.

Preferably the nitrilase of the invention exhibits an increased activity with regard to an arylacetonitrile, more preferably a substituted mandelonitriles. The mandelonitrile aryl-group may carry one or more substituents. Preferred substituents may be alkyl (preferably methyl), alkoxy (preferably methoxy), hologen, or nitro. The substituted mandelonitrile may be selected from—but not limited to—the group consisting of o-fluoromandelonitrile, p-fluoromandelonitrile, m-fluoromandelonitrile, o-chloromandelonitrile, p-chloromandelonitrile, m-chloromandelonitrile, o-bromomandelonitrile, p-bromomandelonitrile, m-bromomandelonitrile, o-nitromandelonitrile, p-nitromandelonitrile, m-nitromandelonitrile, o-methylmandelonitrile, p-methylmandelonitrile, m-methylmandelonitrile, o-methoxymandelonitrile, p-methoxymandelonitrile or m-methoxymandelonitrile. More preferred is o-chloromandelonitrile.

Preferably, a optically active carbonic acid is produced using the method of this invention comprising at least one compound selected from the group consisting of R-mandelic acid, S-mandelic acid, R-p-chloromandelic acid, S-p-chloromandelic acid, R-m-chloromandelic acid, S-m-chloromandelic acid, R-o-chloromandelic acid, S-o-chloromandelic acid, S-o-bromomandelic acid, S-p-bromomandelic acid, S-m-bromomandelic acid, S-o-methylmandelic acid, S-p-methylmandelic acid, S-m-methylmandelic acid, R-o-bromomandelic acid, R-p-bromomandelic acid, R-m-bromomandelic acid, R-o-methylmandelic acid, R-p-methylmandelic acid or R-m-methylmandelic acid. More preferred is R-o-chloromandelic acid.

Yet another embodiment of the invention comprises a nucleic sequence encoding a nitrilase of this invention. Preferably said nucleic acid sequence is encoding an enzyme with nitrilase activity, which comprises at least one sequence selected from the group of sequences comprising

```
                                        (SEQ ID NO: 24)
    a)       (K/R/H)XXDXXGX(X*),
``` b) a sequence having a homology of at least 50%, preferably at least 60%, more preferably at least 70% or 80%, most preferably at least 90% or 95% with respect to a nitrilase consensus sequence sequence selected from the group of sequences comprising

```
                                         (SEQ ID NO: 9)
    i)       KAINDPVGH(X*)

(SEQ ID NO: 10)
    ii)      GH(X*)SRPDV,
``` and
c) a sequence having a homology of at least 35%, preferably at least 40%, more preferably at least 60% or 80%, most preferably at least 90% or 95% with respect to a nitrilase consensus sequence sequence selected from the group of sequences comprising

```
                                         (SEQ ID NO:11)
    i)      DP(A/V)GH(X*)SRPDV(L/T)(S/R)L,
            and (SEQ ID NO: 12)
    ii)     DPAGH(X*)SRPDVLSLLV,
``` provided that in said sequence comprised in said enzyme with nitrilase activity said residue X* represents an amino acid residue which is not tyrosine, and wherein X* is localized at a position corresponding to position 296 in wild-type Alcaligenes faecalis nitrilase as described by SEQ ID NO: 2.

More preferably, a nucleic acid of the invention is encoding a nitrilase comprising a sequence selected from the group consisting of

```
                                         (SEQ ID NO: 13)
    a)      (K/R)XXXDXXG(H/Y/S)(X*), (SEQ ID NO: 25)
    b)      KXXXDXXGX(X*), (SEQ ID NO: 9)
    c)      KAINDPVGH(X*), (SEQ ID NO: 10)
    d)      GH(X*)SRPDV, (SEQ ID NO: 11)
    e)      DP(A/V)GH(X*)SRPDV(L/T)(S/R)L,
            and (SEQ ID NO: 12)
    f)      DPAGH(X*)SRPDVLSLLV,
``` wherein X stands for any amino acid and provided that in said sequence comprised in said nitrilase of the invention X* represents an amino acid residue which is not tyrosine, and wherein X* is localized at a position corresponding to position 296 in wild-type Alcaligenes faecalis nitrilase as described by SEQ ID NO: 2.

Even more preferably, a nucleic acid of the invention encodes an enzyme with nitrilase activity comprises a sequence selected from the group consisting of

```
                                         (SEQ ID NO: 9)
    a)      KAINDPVGH(X*), (SEQ ID NO: 11)
    b)      DP(A/V)GH(X*)SRPDV(L/T)(S/R)L,
            or, most preferably, (SEQ ID NO: 12)
            DPAGH(X*)SRPDVLSLLV,
```

In an preferred embodiment the residue X* is selected from the group consisting of cysteine, alanine, asparagine, glycine, serine, phenylalanine, and threonine. More preferred, the residue X* is selected from the group consisting of alanine, cysteine, asparagine, and serine. Most preferred, the residue X* is selected from the group consisting of alanine, and cysteine.

Most preferably a nucleic acid sequence of the invention is further characterized as being described by a sequence selected from the group consisting of:
a) a nucleic acid sequence which is at least 60%, preferably 80%, more preferably 90%, most preferably 95% identical to the nucleic acid sequence of SEQ ID NO: 1, 3, 5, or 7; and
b) a nucleic acid sequence comprising at least one fragment of at least 20 consecutive bases, preferably 50 consecutive bases, more preferably 100 consecutive bases of at least one of the sequences described by SEQ ID NO: 1, 3, 5, or 7.

For recombinant expression of a nitrilase according to the invention, a nucleic acid sequence encoding said nitrilase may be incorporated into an expression construct.

The term "expression construct" in general means any nucleic acid construct, wherein a nucleic acid molecule whose expression (transcription and, if appropriate, translation) generates a nitrilase is preferably operably linked to at least one genetic control element. The term "genetic control sequences" is to be understood in the broad sense and refers to all those sequences which have an effect on the materialization, propagation or function of the expression cassette or a recombinant microorganism according to the invention. These genetic control elements are, for example, sequences to which the inducers or repressors bind and thus regulate the expression of the nucleic acid. Genetic control sequences may enhance, regulate, guarantee, or modify the transcription and/or translation in prokaryotic or eukaryotic organisms. Genetic control sequences are, for example, described in "Goeddel; Gene Expression Technology: Methods in Enzymology 185, Academic Press, San Diego, Calif. (1990)", "Gruber and Crosby, in: Methods in Plant Molecular Biology and Biotechnolgy, CRC Press, Boca Raton, Fla., eds.:Glick and Thompson, Chapter 7, 89-108", and in the references cited therein.

In addition to these novel regulatory sequences, it is also possible for the natural regulation of these sequences to be present upstream (in front) of the actual structural genes and, where appropriate, to have been genetically modified so that the natural regulation is switched off and the expression of the genes has been increased. The nucleic acid construct may, however, also have a simpler structure, that is to say no additional regulatory signals have been inserted upstream of a nucleic acid sequence of the invention, and the natural promoter with its regulation has not been deleted. Instead, the natural regulatory sequence is mutated in such a way that the regulation no longer takes place, and gene expression is increased. The nucleic acid construct may additionally advantageously comprise one or more enhancer sequences, which make increased expression of the nucleic acid sequence possible, functionally linked to the promoter. It is also possible to insert advantageous additional sequences at the 3' end of the DNA sequences, such as other regulatory elements or terminators. The nucleic acids according to the invention may be present in one or more copies in the construct. The construct may also comprise further markers such as antibiotic resistances or auxotrophy-complementing genes where appropriate for selection of the construct.

In a preferred embodiment, the nucleic acid sequence encoding a nitrilase of the invention is operably linked to at least one promoter sequence which ensures its expression in an organism (e.g., a microorganism or a plant).

Operable linkage is to be understood as meaning, for example, the sequential arrangement of a promoter with the nucleic acid sequence to be expressed (for example an nitrilase) and, if appropriate, further regulatory elements such as, for example, a terminator in such a way that each of the regulatory elements can fulfill its function when the nucleic acid sequence is expressed recombinantly. A direct linkage in the chemical sense is not always necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 500 base pairs, especially preferably less than 200 base pairs, very especially preferably less than 100 base pairs.

Operable linkage, and an expression cassette, can be generated by means of customary recombination and cloning techniques as are described, for example, in Maniatis T, Fritsch E F and Sambrook J (1989) Molecular Cloning: A Laboratory Manual, Cold Spring Harbor Laboratory, Cold Spring Harbor (NY), in Silhavy T J, Berman M L and Enquist L W (1984) Experiments with Gene Fusions, Cold Spring Harbor Laboratory, Cold Spring Harbor (NY), in Ausubel F M et al. (1987) Current Protocols in Molecular Biology, Greene Publishing Assoc. and Wiley Interscience and in Gelvin et al. (1990) In: Plant Molecular Biology Manual. However, further sequences which, for example, act as a linker with specific cleavage sites for restriction enzymes, or as a signal peptide, may also be positioned between the two sequences. The insertion of sequences may also lead to the expression of fusion proteins.

The expression cassettes according to the invention encompass a promoter function in the respective host organism 5'-upstream of the nucleic acid sequence in question to be expressed recombinantly, and 3'-downstream a terminator sequence as additional genetic control sequence and, if appropriate, further customary regulatory elements, in each case linked operably to the nucleic acid sequence to be expressed recombinantly.

Depending on the host organism to be transformed with an expression cassette or vector of the invention, different genetic control sequences are preferred.

Advantageous regulatory sequences for carrying out the invention in microorganisms are, for example, present in promoters such as cos, tac, trp, tet, trp-tet, lpp, lac, lpp-lac, lacI$^q$ T7, T5, T3, gal, trc, rhaP (rhaP$_{BAD}$), ara, SP6, $\lambda$-P$_R$ or the $\lambda$-P$_L$ promoter, which are advantageously used in Gram-negative bacteria. Further advantageous regulatory sequences are, for example, the Gram-positive promoters amy and SPO2, in the fungal or yeast promoters ADC1, MF$\alpha$, AC, P-60, CYC1, GAPDH, TEF, rp28, ADH. Also advantageous in this connection are the promoters of pyruvate decarboxylase and of methanol oxidase from, for example, Hansenula pr Pichia (like e.g., the AOX promoter). It is also possible to use artificial promoters for the regulation.

Plant-specific promoters suitable for expression of the nitrilase in plant organisms may include constitutive promoters (e.g., CaMV 35S promoter (Franck et al. (1980) Cell 21:285-294), OCS promoter, ubiquitin promoter (Holtorf S et al. (1995) Plant Mol Biol 29:637-649), promoter of the *Arabidopsis thaliana* nitrilase-1 gene (GenBank Acc. No.: U38846, nucleotides 3862 to 5325 or else 5342), tissue-specific promoters (e.g., phaseolin promoter; U.S. Pat. No. 5,504,200) or chemically inducible promoters (review article: Gatz et al. (1997) Annu Rev Plant Physiol Plant Mol Biol 48:89-108).

In principle, all natural promoters with their regulatory sequences like those mentioned above may be used for the method according to the invention. In addition, synthetic promoters may also be used advantageously.

An expression construct or vector of the invention may also comprise further functional elements. The term functional element is to be understood in the broad sense and refers to all those elements which have an effect on the generation, amplification or function of the expression cassettes, vectors or recombinant organisms according to the invention. The following may be mentioned by way of example, but not by limitation:

a). Selection Markers

Selection markers are useful to select and separate successfully transformed or homologous recombined cells and to prevent loss of an extrachromosomal DNA-construct over the time. Selection markers confer a resistance to a biocidal compound such as a metabolic inhibitor (e.g., 2-deoxyglucose-6-phosphate, WO 98/45456), antibiotics (e.g., ampicillin, tetracycline, kanamycin, G 418, bleomycin or hygromycin) or herbicides (e.g., phosphinothricin or glyphosate).

Selection markers suitable for prokarytic organisms may include, but shall not be limited to: Amp (ampicillin resistance; β-Lactamase), Cab (Carbenicillin resistance), Cam (Chloramphenicol resistance), Kan (kanamycin resistance), Rif (rifampicin resistance), Tet (tetracycline resisteace), Zeo (Zeocin resistance), or Spec (Spectinomycin resistance). The selective pressure is kept by certain levels of the antibiotic in the medium (like, e.g., Ampicillin 100 mg/l, Carbenicillin 100 mg/l, Chloramphenicol 35 mg/l, Kanamycin 30 mg/l, rifampicin 200 mg/l, tetracycline 12.5 mg/l, Spectinomycin 50 mg/l).

For use in plants, especially preferred selection markers are those which confer resistance to herbicides. Examples are Phosphinothricin acetyltransferases (PAT; de Block et al. (1987) EMBO J. 6: 2513-2518), 5-enolpyruvylshikimate-3-phosphate synthase (EPSPS), sulfonylurea- and imidazolinone-inactivating acetolactate synthases, Bromoxynil® degrading nitrilases (bxn). In other eukaryotic organisms, Kanamycin- or. G418-resistance genes (NPTII; NPTI) can be used.

Selection markers further comprise sequences suitable for complementation of a genetic defect in the host organism, like e.g. a deficiency in amino acid synthesis. Complementation allows the host cell to grow on a medium deficient in said amino acid. Suitable are for example deficiencies in the synthesis of tryptophan (e.g., trpC), leucine (e.g., leuB), or histidine (e.g., hisB). Corresponding microorganism strains are commercially available (e.g., from Clontech Inc.) and can be complemented by selectable markers like e.g., TRP1, Leu2, or HIS3, respectively.

b) Transcription terminator sequences: Transcription terminator sequences prevent unintended transcription (e.g., read-through) and enhance plasmid and/or mRNA stability and/or amount.

c) Shine-Dalgarno sequences (SD) are useful for initiation of translation. A suitable consensus sequence for expression for *E. coli* is for example: 5'-TAAGGAGG-3'. Said sequence may be localized 4 to 14 nucleotides upstream of the ATG start-codon, wherein the optimum is 8 nucleotides. For preventing secondary RNA structures, which may reduce translation efficacy, the corresponding region should be preferably A/T-rich.

d) Start codon: The start codon is the point of initiation for translation. In *E. coli* and higher eukaryotic organisms ATG is the most often used start codon. In *E. coli* GTG may be used alternatively.

e) Tags and fusion proteins: N- or C-terminal fusions of the recombinant protein with shorter peptides ("tags") or other proteins ("fusion proteins") may be used to allow an improved expression, solubility, detection, or purification. Preferably, the fusion part comprises a protease (e.g., thrombine or factor X) cleavage site, which allows removal of the fusion part after expression and purification.

f) Multiple cloning sites (MCS) allow and facilitate insertion of one or more nucleic acid sequences.

g) Stop codons/translation terminators: Among the three possible stop codons TAA is preferred (since TAG and TGA may under certain circumstances allow read-through translation). Multiple stop codons can be used to guarantee translation termination.

h) Reporter genes: Reporter genes encode readily quantifiable proteins and, via their color or enzyme activity, make possible an assessment of the transformation efficacy, the site of expression or the time of expression. Very especially preferred in this context are genes encoding reporter proteins (Schenborn E & Groskreutz D (1999) Mol Biotechnol 13(1):29-44) such as the green fluorescent protein (GFP), chloramphenicol transferase, luciferase (Ow et al. (1986) Science 234:856-859), or β-galactosidase.

i) Origins of replication, which ensure amplification of the expression cassettes or vectors according to the invention in, for example, *E. coli*. Examples which may be mentioned are ORI (origin of DNA replication), the pBR322 ori or the P15A ori (Sambrook et al.: Molecular Cloning. A Laboratory Manual, 2nd ed. Cold Spring Harbor Laboratory Press, Cold Spring Harbor, N.Y., 1989).

j) Elements which are necessary for *Agrobacterium*-mediated plant transformation, such as, for example, the right or left border of the T-DNA or the vir region.

k) Expression cassettes mediating expression of chaperone proteins (like e.g., GroELS, dnaKJ, grpE, or clpB), known to increase levels of correctly folded proteins especially in recombinant expression systems (U.S. Pat. No. 5,635,391).

l) Elements which facilitate plasmid segregation and distribution during host amplification (like e.g., cer-sites; Wilms B et al. (2001) Biotechnol Bioeng 73(2):95-103).

The introduction of an expression cassette according to the invention into an organism or cells, tissues, organs, parts or seeds thereof can be effected advantageously using vectors which comprise the expression cassettes. The expression cassette can be introduced into the vector (for example a plasmid) via a suitable restriction cleavage site. The plasmid formed is first introduced into *E. coli*. Correctly transformed *E. coli* are selected, grown, and the recombinant plasmid is obtained by the methods familiar to the skilled worker. Restriction analysis and sequencing may serve to verify the cloning step. Examples of vectors may be plasmids, cosmids, phages, viruses or else agrobacteria. In an advantageous embodiment, the expression cassette is introduced by means of plasmid vectors.

Examples of suitable plasmids in *E. coli* are pUC18, PUC19, pBlueScript series, pKK223-3, pJOE2702, pBAD, pLG338, pACYC184, pBR322, pUC18, pUC19, pKC30, pRep4, PHS1, pHS2, pPLc236, pMBL24, pLG200, pUR290, pIN-III$^{113}$-B1, λgt11 or pBdCI, in *Streptomyces* are pIJ101, pIJ364, pIJ702 or pIJ361, in *Bacillus* are pUB110, pC194 or pBD214, in *Corynebacterium* are pSA77 or pAJ667, in fungi are pALS1, pIL2 or pBB116, in yeasts are 2 μM, pAG-1, YEp6, YEp13 or pEMBLYe23 or in plants are PLGV23, pGHlac⁺, pBIN19, pAK2004 or pDH51. Vectors for expression in higher eukaryotic (e.g., mammalian) cells containing viral sequences on the basis of SV40, papilloma-virus, adenovirus or polyomavirus (Rodriquez R L & Denhardt D T, ed.; Vectors: A survey of molecular cloning vectors and their uses, Butterworths (1988), Lenstra et al. (1990) Arch Virol 110:1-24). Said plasmids represent a small selection of the possible plasmids. Further plasmids are well known to the skilled worker and can be found, for example, in the book Cloning Vectors (eds. Pouwels P H et al. Elsevier, Amsterdam-New York-Oxford, 1985, ISBN 904018). All recombinant molecules comprising the nucleic acid sequence under the control of regulating sequences enabling expression of a nitrilase of the invention are considered to be part of the present invention.

The invention furthermore relates to recombinant organisms or tissues, organs, parts, cells or propagation material thereof which comprise a nitrilase of the invention, a nucleic acid sequence encoding said nitrilase, a recombinant expression cassette comprising said nucleic acid sequence, or a recombinant vector encompassing said expression cassette.

Such a recombinant organism is generated, for example, by means of transformation or transfection with the corresponding proteins or nucleic acids. The generation of a transformed organism (or a transformed cell or tissue) requires introducing the DNA in question (for example the expression vector), RNA or protein into the host cell in question. A multiplicity of methods are available for this procedure, which is termed transformation (or transduction or transfection) (Keown et al. (1990) Methods in Enzymology 185:527-537). For example, the DNA or RNA can be introduced directly by microinjection or by bombardment with DNA-coated microparticles. Also, the cell can be permeabilized chemically, for example using polyethylene glycol, so that DNA can enter the cell by diffusion. The DNA can also be introduced by calcium phosphate mediation, or fusion with DNA-containing units such as minicells, lysosomes or liposomes. Another suitable method of introducing DNA is electroporation, where the cells are permeabilized reversibly by an electrical pulse. Preferred general methods include but shall not be limited to calcium phosphate mediated transformation, DEAE-dextrane mediated transformation, cationic lipid mediated transformation, electroporation, transduction, and infection. These methods are well known to the person skilled in the art (Davis et al.(1986) Basic Methods In Molecular Biology; Sambrook J et al. (1989) Molecular cloning: A laboratory manual, Cold Spring Harbor Laboratory Press; Ausubel F M et al. (1994) Current protocols in molecular biology, John Wiley and Sons; Glover D M et al. (1995) DNA Cloning Vol. 1, IRL Press ISBN 019-963476-9).

In plants, in addition to these "direct" transformation techniques, transformation can also be effected by bacterial infection by means of *Agrobacterium tumefaciens* or *Agrobacterium rhizogenes*. The *Agrobacterium*-mediated transformation is best suited to dicotyledonous plant cells. The methods are described and well known in the art (Horsch R B et al. (1985) Science 225: 1229f.; EP 120 516; Hoekema, In: The Binary Plant Vector System, Offsetdrukkerij Kanters B. V., Alblasserdam, Chapter V; An et al. (1985) EMBO J 4:277-287). When *Agrobacteria* are used, the expression cassette is integrated into specific plasmids, either into a shuttle or intermediate vector, or into a binary vector. Binary vectors are preferably used (Holsters et al. (1978) Mol Gen Genet 163:181-187). Various binary vectors are known, some of which are commercially available such as, for example, pBI101.2 or pBIN19 (Clontech Laboratories, Inc. USA).

Untransformed cells can be selected from untransformed cells when a selectable marker is part of the DNA introduced. Examples of genes which can act as markers are all those which are capable of conferring resistance to antibiotics or herbicides are given above. Concerning plants, the skilled worker is familiar with such methods of regenerating intact plants from plant cells and plant parts. Methods to do so are described, for example, by Fennell et al. (1992) Plant Cell Rep. 11: 567-570; Stoeger et al (1995) Plant Cell Rep. 14:273-278; Jahne et al. (1994) Theor Appl Genet 89:525-533.

The invention also relates to recombinant organisms transformed with at least one of the nucleic acid sequences according to the invention, expression cassette according to the invention or vector according to the invention, and to cells, cell cultures, tissues, parts—such as, for example, leaves, roots and the like in the case of plant organisms—or propagation material derived from such organisms. The term organism is to be understood in the broad sense and refers to prokaryotic and eukaryotic organisms, preferably bacteria, yeasts (like e.g., *Saccharomyces*, *Kluyveromyces* or *Pichia*), fungi (like e.g., *Aspergillus* or *Penicilium*), non-human animal organisms and plant organisms. Preferred plant organisms are indicated above.

The term "microorganism" or "bacteria" includes gram-positive and gram-negative bacteria. Preferred are all Enterobacteriaceae genera and species, and all Actinomycetales orders and species. Especially preferred are the Enterobacteriaceae species *Escherichia, Serratia, Proteus, Enterobacter, Klebsiella, Salmonella, Shigella, Edwardsielle, Citrobacter, Morganella, Providencia*, and *Yersinia*. Further preferred are all species of *Agrobacterium, Pseudomonas, Burkholderia, Nocardia, Acetobacter, Gluconobacter, Corynebacterium, Brevibacterium, Bacillus, Clostridium, Cyanobacter, Staphylococcus, Aerobacter, Alcaligenes, Rhodococcus*, and *Streptomyces*. For expression of recombinant nitrilases *Escherichia* species are most preferred, especially *Escherichia coli*.

The term "plant" or "plant organism" as used herein means any organism capable of photosynthesis. Preferably, the organism is a differentiated multicellular organization. The term includes all genera and species of higher and lower plants of the Plant Kingdom. Furthermore included are the mature plants, seed, shoots and seedlings, and parts, propagation material and cultures derived therefrom, for example cell cultures. Especially preferred are monocotyledoneous and dicotyledoneous plants, more particularly of the plants of culture intended for animal or human feed or food purpose or for industrial utilization, like corn, wheat, barley, canola, soybean, rice, sugarcane, sugar beet, potato, beet, tobacco, cotton, etc.

The recombinant organisms can be generated with the above-described methods for the transformation or transfection of organisms.

A microorganisms of this invention can be grown and propagated in a medium, which allows growth of said microorganism. Said medium can be of synthetic or natural origin. Various media are available depending on the microorganism and known to the person skilled in the art. For growth of microorganism the media comprise a carbon source, a nitrogen source, inorganic salts and optionally small amounts of vitamins and/or trace elements.

Preferred carbon sources are, for example, polyoles like, e.g., glycerol, sugars like e.g., mono-, di- or polysaccharides (e.g., glucose, fructose, mannose, xylose, galactose, ribose, sorbose, ribulose, lactose, maltose, sucrose, raffinose, starch or cellulose), complex sugar sources (e.g., molasses), sugar phosphates (e.g., fructose-1,6-bisphosphate), sugar alcohols (e.g., mannit), alcohols (e.g., methanol or ethanol), carbonic acids (e.g., citric acid, lactic acid or acetic acid), oils and fats (e.g., soybean oil or rapeseed oil), amino acids or amino acid mixtures (e.g., Casamino acids; Difco) or distinct amino acids (e.g., glycine, asparagine) or amino-sugars, wherein the later can also be utilized as nitrogen sources. More preferred are glucose and polyoles, especially glycerol.

Preferred nitrogen sources are organic or inorganic nitrogen compounds or materials, comprising said compounds. Examples are ammonia salts (e.g., $NH_4Cl$ or $(NH_4)_2SO_4$), nitrates, urea, and complex nitrogen sources like e.g., brewers yeast autolysate, soybean flour, wheat gluten, yeast extract, peptone, meat extract, caseine hydrolysate, yeast or potato protein, which may also often also function as carbon sources.

Examples for inorganic salts include calcium, magnesium, sodium, cobalt, molybdenum, manganese, potassium, zinc, copper and iron salts. As corresponding anions chlorine, sulfate, sulfide, and phosphate ions are especially preferred. An important issue for enhancing productivity is the control of the $Fe^{2+}$ or $Fe^{3+}$-ion concentration of the medium.

Optionally, the medium may comprise additional growth factors like e.g., vitamins or growth promoters like biotin, 2-keto-L-gulonic acid, ascorbic acid, thiamine, folic acid, nicotinic acid, pantothenate or pyridoxine, amino acids (e.g., alanine, cysteine, proline, asparagine, glutamine, serine, phenylalanine, ornithine or valine), carbonic acids (e.g., citric acid, formic acid, lactic acid) or substances like dithiothreitole.

The balance of the individual nutrients depends on the fermentation mode and will be adopted to the individual requirements. The media components may be provided at the beginning of the fermentation, after they have been sterilized before if required, or may be continuously or discontinuously added according to the requirements of the culture during the fermentation process.

The fermentation and growth conditions are selected in a way to guarantee optimal yield of the product (e.g., optimal yield of nitrilase activity). Preferred fermentation conditions are between 15° C. to 40° C., preferably 25° C. to 37° C. The pH is preferably kept in a range of pH 3 to 9, preferably pH 5 to 8. In general the fermentation time may take from a few hours to several days, preferably from 8 hours to 21 days, more preferably from 4 hours to 14 days. Processes for optimization of media and fermentations conditions is well known in the art (Applied Microbiol Physiology, "A Practical Approach (Eds. P M Rhodes, P F Stanbury, IRL-Press, 1997, S.53-73, ISBN 0 19 963577 3).

The invention further relates to a method for preparing optically active, chiral, or achiral carboxylic acids, which comprises converting nitrites in the presence of an amino acid sequence encoded by the nucleic acids according to the invention, or a growing, dormant or disrupted abovementioned microorganism (=host organism) which contains either a nucleic acid sequence according to the invention, a nucleic acid construct according to the invention which contains a nucleic acid according to the invention linked to one or more regulatory signals, or a vector according to the invention, into the optically active, chiral or achiral carboxylic acids.

An advantageous embodiment of the method is the conversion of optically active, chiral or achiral aliphatic nitrites into the corresponding carboxylic acids.

The term "nitrile" as used herein means preferably any organic compound which comprises at least one nitrile grouping. The term "nitrile" also includes mixtures of aldehyde or ketone and cyanide which lead to formation of at least one nitrile. The term "cyanide" as used herein shall mean compound which comprise or lead to release of a cyanide ion (CN⁻). Preferably the term "cyanide" shall include prussic acid and/or cyanide salts like e.g., more preferably sodium cyanide or potassium cyanide. The term "mixture" as used in this context shall mean all quantitative combinations of the aldehyde/ketone and the cyanide which result in formation of a nitrile. Preferably the mixture consists of equimolar or nearly equimolar quantities of aldehyde/ketone and cyanide.

Another preferred embodiment of the invention is a method for preparing optically active, chiral or achiral carboxylic acids, wherein nitriles of the general formula I are converted in the presence of a nitrilase of the invention, or a growing, dormant or disrupted abovementioned microorganism which contains either a nucleic acid sequence encoding a nitrilase according to the invention, an expression cassette according to the invention, or a vector according to the invention, into carboxylic acids of the general formula II.

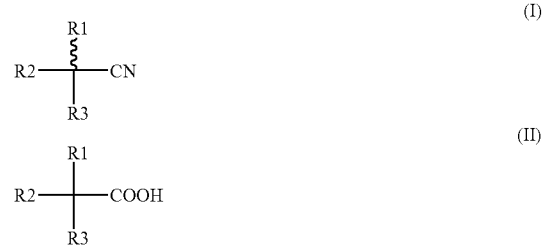

where the substituents and variables in the formulae I and II have the following meanings:
$R^1$, $R^2$, $R^3$ may independently of one another be selected from the group consisting of hydrogen, substituted or unsubstituted, branched or unbranched $C_1$-$C_{10}$-alkyl or $C_1$-$C_{10}$-alkoxy, substituted or unsubstituted aryl or heteroaryl, hydroxyl, halogen such as fluorine, chlorine or bromine, $C_1$-$C_{10}$-alkylamino and amino, and where at least two—preferably all—of the substituents $R^1$, $R^2$ and $R^3$ are different.

It is advantageous for one of the $R^1$, $R^2$ or $R^3$ substituents in the formulae I and II to be aryl, such as phenyl. It is further preferred for one of the $R^1$, $R^2$ or $R^3$ substituents in the formulae I and II to be hydroxyl and one to be hydrogen or methyl.

Suitable substituents for said $R^1$, $R^2$ or $R^3$ radicals are, for example, one or more substituents such as halogen such as fluorine, chlorine or bromine, mercapto, nitro, amino, hydroxyl, alkyl, alkoxy, alkenyl, alkenyloxy, alkynyl or other aromatic or other saturated or unsaturated nonaromatic rings or ring systems. Preferred are alkyl radicals such as $C_1$-$C_6$-alkyl such as methyl, ethyl, propyl or butyl, aryl such as phenyl, thiophenyl, halogen such as chlorine, fluorine or bromine, hydroxyl or amino. In a preferred embodiment the method for preparing optically active, chiral or achiral carboxylic acids comprises conversion of a nitrile of the general formula III into carboxylic acids of the general formula IV

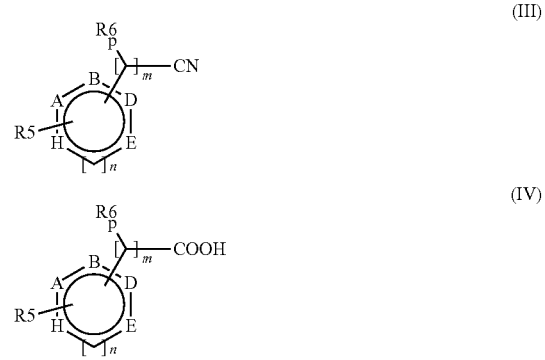

wherein the substituents and variables in the formulae I and II have the following meanings:
n=0 or 1
m=0, 1, 2 or 3, where for m>2 there is one or no double bond present between two adjacent carbon atoms,
p=0 or 1
A, B, D and E independently of one another are CH, N or CR7
H=O, S, NR4, CH or CR7, when n=0, or CH, N or CR7, when n=1, wherein it is possible for two adjacent variables A, B, D, E or H together to form another substituted or unsubstituted aromatic, saturated or partially saturated ring with 5 to 8 atoms in the ring which may contain one or more heteroatoms such as O, N or S, and not more than three of the variables A, B, D, E or H being a heteroatom, and wherein R4 is selected from the group consisting of hydrogen, substituted or unsubstituted, branched or unbranched $C_1$-$C_{10}$-alkyl, and wherein R5, R6, R7 may independently be selected from the group consisting of hydrogen, substituted or unsubstituted, branched or unbranched $C_1$-$C_{10}$-alkyl or $C_1$-$C_{10}$-alkoxy, substituted or unsubstituted aryl or heteroaryl, hydroxyl, halogen such as fluorine, chlorine or bromine, $C_1$-$C_{10}$-alkylamino and amino.

Suitable substituents for said $R^4$, $R^5$ or $R^6$ radicals are, for example, one or more substituents such as halogen such as fluorine, chlorine or bromine, mercapto, nitro, amino, hydroxyl, alkyl, alkoxy, alkenyl, alkenyloxy, alkynyl, or other aromatic or other saturated or unsaturated nonaromatic rings or ring systems. Preference is given to alkyl radicals such as $C_1$-$C_6$-alkyl such as methyl, ethyl, propyl or butyl, aryl such as phenyl, thiophenyl, halogen such as chlorine, fluorine or bromine, hydroxyl or amino.

Alkyl radicals mentioned above may comprise substituted or unsubstituted, branched or unbranched $C_1$-$C_{10}$-alkyl chains such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Methyl, ethyl, n-propyl, n-butyl, i-propyl or i-butyl is preferred.

Alkenyl radicals mentioned above may comprise branched or unbranched $C_1$-$C_{10}$-alkenyl chains such as, for example, ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, nonenyl or decenyl. Ethenyl, propenyl, butenyl or pentenyl are preferred.

Alkoxy radicals mentioned above may be substituted or unsubstituted, branched or unbranched $C_1$-$C_{10}$-alkoxy chains such as, for example, methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-Ethyl-1-methylpropoxy, 1-ethyl-2-methylpropoxy, hexyloxy, heptyloxy, octyloxy, nonyloxy or decyloxy and the branched-chain homologs thereof.

Alkylcarbonyl radicals mentioned above may be substituted or unsubstituted, branched or unbranched $C_1$-$C_{10}$-alkylcarbonyl chains such as, for example, methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, n-hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl, 1-ethyl-2-methylpropylcarbonyl, nheptylcarbonyl, n-octylcarbonyl, n-nonylcarbonyl or ndecylcarbonyl. Methylcarbonyl, ethylcarbonyl, n-propylcarbonyl, n-butylcarbonyl, i-propylcarbonyl or i-butylcarbonyl are preferred.

Alkenylcarbonyl radicals mentioned above may be branched or unbranched $C_2$-$C_{10}$-alkenylcarbonyl chains such as, for example, ethenylcarbonyl, propenylcarbonyl, 1-butenylcarbonyl, 2-butenylcarbonyl, 3-butenylcarbonyl, 2-methylpropenylcarbonyl, 1-pentenylcarbonyl, 2-pentenylcarbonyl, 3-pentenylcarbonyl, 4-pentenylcarbonyl, 1-methyl-1-butenylcarbonyl, 2-methyl-1-butenylcarbonyl, 3-methyl-1-butenylcarbonyl, 1-methyl-2-butenylcarbonyl, 2-methyl-2-butenylcarbonyl, 3-methyl-2-butenylcarbonyl, 1-methyl-3-butenylcarbonyl, 2-methyl-3-butenylcarbonyl, 3-methyl-3-butenylcarbonyl, 1,1-dimethyl-2-propenylcarbonyl, 1,2-dimethyl-1-propenylcarbonyl, 1,2-dimethyl-2-propenylcarbonyl, 1-ethyl-1-propenylcarbonyl, 1-ethyl-2-propenylcarbonyl, 1-hexenylcarbonyl, 2-hexenylcarbonyl, 3-hexenylcarbonyl, 4-hexenylcarbonyl, 5-hexenylcarbonyl, 1-methyl-1-pentenylcarbonyl, 2-methyl-1-pentenylcarbonyl, 3-methyl-1-pentenylcarbonyl, 4-methyl-1-pentenylcarbonyl, 1-methyl-2-pentenylcarbonyl, 2-methyl-2-pentenylcarbonyl, 3-methyl-2-pentenylcarbonyl, 4-methyl-2-pentenylcarbonyl, 1-methyl-3-pentenylcarbonyl, 2-methyl-3-pentenylcarbonyl, 3-methyl-3-pentenylcarbonyl, 4-methyl-3-pentenylcarbonyl, 1-methyl-4-pentenylcarbonyl, 2-methyl-4-pentenylcarbonyl, 3-methyl-4-pentenylcarbonyl, 4-methyl-4-pentenylcarbonyl, 1,1-dimethyl-2-butenylcarbonyl, 1,1-dimethyl-3-butenylcarbonyl, 1,2-dimethyl-1-butenylcarbonyl, 1,2-dimethyl-2-butenylcarbonyl, 1,2-dimethyl-3-butenylcarbonyl, 1,3-dimethyl-1-butenylcarbonyl, 1,3-dimethyl-2-butenylcarbonyl, 1,3-dimethyl-3-butenylcarbonyl, 2,2-dimethyl-3- butenylcarbonyl, 2,3-dimethyl-1-butenylcarbonyl, 2,3-dimethyl-2-butenylcarbonyl, 2,3-dimethyl-3-butenylcarbonyl, 3,3-dimethyl-1-butenylcarbonyl, 3,3-dimethyl-2-butenylcarbonyl, 1-ethyl-1-butenylcarbonyl, 1-ethyl-2-butenylcarbonyl, 1-ethyl-3-butenylcarbonyl, 2-ethyl-1-butenylcarbonyl, 2-ethyl-2-butenylcarbonyl, 2-ethyl-3-butenylcarbonyl, 1,1,2-trimethyl-2-propenylcarbonyl, 1-ethyl-1-methyl-2-propenylcarbonyl, 1-ethyl-2-methyl-1-propenylcarbonyl, 1-ethyl-2-methyl-2-propenylcarbonyl, 1-heptenylcarbonyl, 2-heptenylcarbonyl, 3-heptenylcarbonyl, 4-heptenylcarbonyl, 5-heptenylcarbonyl, 6-heptenylcarbonyl, 1-octenylcarbonyl, 2-octenylcarbonyl, 3-octenylcarbonyl, 4-octenylcarbonyl, 5-octenylcarbonyl, 6-octenylcarbonyl, 7-octenylcarbonyl, nonenylcarbonyl or decenylcarbonyl. Ethenylcarbonyl, propenylcarbonyl, butenylcarbonyl or pentenylcarbonyl are preferred.

Aryl radicals mentioned above may be substituted and unsubstituted aryl radicals which contain 6 to 20 carbon atoms in the ring or ring system. These may comprise aromatic rings fused together or aromatic rings linked by alkyl, alkylcarbonyl, alkenyl or alkenylcarbonyl chains, carbonyl, oxygen or nitrogen. The aryl radicals may also be linked, where appropriate, via a $C_1$-$C_{10}$-alkyl, $C_3$-$C_8$-alkenyl, $C_3$-$C_6$-alkynyl or $C_3$-$C_8$-cycloalkyl chain to the basic framework. Phenyl or naphthyl is preferred.

Arylcarbonyl radicals mentioned above may be substituted and unsubstituted arylcarbonyl radicals which contain 6 to 20 carbon atoms in the ring or ring system. The latter may comprise aromatic rings which are fused together or aromatic rings which are linked via alkyl, alkylcarbonyl, alkenyl or alkenylcarbonyl chains, carbonyl, oxygen or nitrogen. Phenylcarbonyl or naphthylcarbonyl are preferred.

Heteroaryl systems mentioned above may be substituted or unsubstituted, simple or fused aromatic ring systems with one or more heteroaromatic 3- to 7-membered rings which may contain one or more heteroatoms such as N, O or S and may, where appropriate, be linked via a $C_1$-$C_{10}$-alkyl, $C_3$-$C_8$-alkenyl or $C_3$-$C_8$-cycloalkyl chain to the basic framework. Examples of such heteroaryl radicals are pyrazole, imidazole, oxazole, isoxazole, thiazole, triazole, pyridine, quinoline, isoquinoline, acridine, pyrimidine, pyridazine, pyrazine, phenazine, purine or pteridine. The heteroaryl radicals may be linked via the heteroatoms or via the various carbon atoms in the ring or ring system or via the substituents to the basic framework. Heteroarylcarbonyl radicals mean heteroaromatic radicals which are linked via a carbonyl radical to the basic framework. Pyridine, imidazole, pyrimidine, purine, pyrazine or quinoline is preferred.

Alkylamino radicals mentioned above may be substituted or unsubstituted, branched or unbranched $C_1$-$C_{10}$-alkylamino chains such as, for example, methylamino, ethylamino, n-propylamino, 1-methylethylamino, n-butylamino, 1-methylpropylamino, 2-methylpropylamino, 1,1-dimethylethylamino, n-pentylamino, 1-methylbutylamino, 2-methylbutylamino, 3-methylbutylamino, 2,2-dimethylpropylamino, 1-ethylpropylamino, n-hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino, 1-ethyl-2-methylpropylamino, n-heptylamino, n-octylamino, n-nonylamino or n-decylamino. Methylamino, ethylamino, n-propylamino, n-butylamino, i-propylamino or i-butylamino is preferred.

Preferred nitrites include aromatic or heteroaromatic nitrites such as 2-phenylpropionitrile, 2-hydroxy-2-phenylactonitrile, 2-amino-2-phenylacetonitrile, 2-chlorophenylpropionitrile, 2-hydroxyphenylpropionitrile, benzonitrile, phenylacetonitrile, trans-cinnamonitrile, 2-hydroxy-4-phenyl-butyronitrile, 3-cyanothiophene or 3-cyanomethylthiophene. Preferred are arylacetonitriles, more preferably a substituted mandelonitriles. The mandelonitrile aryl-group may carry one or more substituents. Preferred substituents may be alkyl (preferably methyl), alkoxy (preferably methoxy), hologen, or nitro. The substituted mandelonitrile may be selected from—but not limited to—the group consisting of o-fluoromandelonitrile, p-fluoromandelonitrile, m-fluoromandelonitrile, o-chloromandelonitrile, p-chloromandelonitrile, m-chloromandelonitrile, o-bromomandelo-nitrile, p-bromomandelonitrile, m-bromomandelonitrile, o-nitromandelonitrile, p-nitromandelonitrile, m-nitromandelonitrile, o-methylmandelonitrile, p-methylmandelonitrile, m-methylmandelonitrile, o-methoxymandelonitrile, p-methoxymandelonitrile or m-methoxymandelonitrile. More preferred is o-chloromandelonitrile.

Racemic nitriles in the method according to the invention mean nitriles which consist of a 50:50 mixture of the two enantiomers or of any other mixture with enrichment of one of the two enantiomers in the mixture or mixture of aldehyde/ketone compound and cyanide.

"Optically active" carboxylic acids in the method according to the invention mean those showing an enantiomeric enrichment. The method preferably results in enantiomeric purities of at least 70% ee, preferably of min. 90% ee, particularly preferably of min. 98% ee, very particularly preferably min. 99% ee. In a preferred embodiment of the invention a exchange of the amino acid residue corresponding to position 296 in wild-type *Alcaligenes faecalis* nitrilase as described by SEQ ID NO: 2 by an amino acid which is not tyrosine does not cause a substantial decrease in the resulting enantiomeric purity of a product, more preferably the exchange results in an unchanged or an improved enantiomeric purity.

The method according to the invention is advantageously carried out at a temperature between 0° C. and 80° C., preferably between 10° C. and 60° C., particularly preferably between 15° C. and 55° C.

The method according to the invention is advantageously carried out at a pH of from 4 to 11, preferably from 4 to 9.

It is further advantageous to use from 0.01 to 30% by weight of nitrile or 0.01 to 30% by weight of a corresponding aldehyde or ketone and 0.01 to 30% by weight of cyanide (e.g., hydrocyanic acid) in the process. The method may be carried out with an excess of cyanide. In some circumstances, this leads to cyanide contents which are higher than those stated. Various amounts of nitrile can be used in the reaction, depending on the nitrile. The smallest amounts (=amounts between 0.01 and 5% by weight) of nitrile are advantageously used for nitrites (cyanohydrins) which are in equilibrium with the corresponding aldehydes and cyanide, since the aldehyde is usually toxic for the microorganisms or enzymes. Volatile nitrites are likewise advantageously employed in amounts between 0.01 and 10% by weight. The reaction is retarded with larger amounts of cyanohydrin or nitrile. In the case of nitrites which have only low or virtually no solvent properties, or nitrites which dissolve in only very small amounts in aqueous medium, it is possible and advantageous to employ larger amounts than those stated above. To increase the conversion and the yield, the reaction is advantageously carried out with controlled addition of the racemic nitrile. The product can be isolated after the end of the reaction or else be removed continuously in a bypass. The method of the invention can be carried out in form of a batch process, wherein the educts are provided at a certain concentration at the beginning of the process and then subsequently converted into the corresponding product. Alternatively, the educts can be continuously added to the reaction mixture, e.g., in a way to keep the educt concentrations constant or nearly constant.

The abovementioned appropriate aldehydes or ketones mean compounds which form the nitrile after reaction between the aldehyde or ketone and cyanide (e.g., hydrocyanic acid), where appropriate with base catalysis. The reaction between aldehyde and cyanide results in cyanohydrins which have the advantage that they are in equilibrium with aldehyde and cyanide. The setting up of an equilibrium with the cyanohydrin means that it is possible with an enzyme which converts only one enantiomer of the nitrile nevertheless to obtain a yield of 100% of theory because the racemic nitrile is continually replenished. With all other nitrites, the nitrile not converted by the enzyme (="wrong" or other enantiomer) is advantageously racemized by a chemical reaction and returned to the process in order to be able to reach a theoretical yield of 100%, or is discarded or purified and chemically hydrolyzed with retention of the stereocenter.

The method of the enzymatic nitrile hydrolization is preferably carried out in an aqueous solution.

The method according to the invention makes it possible to convert a large number of racemic nitriles into the optically active carboxylic acids. It is possible in the method to convert at least 25 mmol of nitrile/h×mg of protein or at least 25 mmol of nitrile/h×g dry weight of the microorganisms, preferably at least 30 mmol of nitrile/h×mg of protein or at least 30 mmol of nitrile/h×g dry weight, particularly preferably at least 40 mmol of nitrile/h×mg of protein or at least 40 mmol of nitrile/h×g dry weight, very particularly preferably at least 50 mmol of nitrile/h×mg of protein or at least 50 mmol of nitrile/h×g dry weight.

It is possible to use growing cells which comprise the nucleic acids, nucleic acid constructs or vectors according to the invention for the method according to the invention. Dormant, immobilized, permeabilized or disrupted cells can also be used. Disrupted cells mean, for example, cells which have been made permeable by a treatment with, for example, solvents, or cells which have been disintegrated by an enzyme treatment, by a mechanical treatment (e.g. French press or ultrasound) or by any other method. The crude exracts obtained in this way are suitable and advantageous for the method according to the invention. Purified or partially purified enzymes can also be used for the process. Immobilized microorganisms or enzymes are likewise suitable and can advantageously be used in the reaction.

The optically active carboxylic acids prepared in the method according to the invention can advantageously be isolated from the aqueous reaction solution by extraction or crystallization or by extraction and crystallization. For this purpose, the aqueous reaction solution may be concentrated (e.g., by evaporation or lyophyllisation), and is acidified with an acid such as a mineral acid (e.g. HCl or $H_2SO_4$) or an organic acid, advantageously to pH 3 or pH values below 3, and then extracted with an organic solvent. The extraction can be repeated several times to increase the yield. Organic solvents which can be used are in principle all solvents which show a phase boundary with water, where appropriate after addition of salts. Advantageous solvents are solvents such as toluene, benzene, hexane, methyl tert-butyl ether or ethyl acetate.

After concentration of the organic phase, the products can usually be isolated in good chemical purities, meaning a chemical purity of greater than 90%. After extraction, the organic phase with the product can, however, also be only partly concentrated, and the product can be crystallized. For this purpose, the solution is advantageously cooled to a temperature of from 0° C. to 25° C. (room temperature). The crystallization can also take place directly from the organic solution. The crystallized product can be taken up again in the same or a different solvent for renewed crystallization and be crystallized once again. The subsequent crystallization at least once may, depending on the position of the eutectic composition, further increase the enantiomeric purity of the product.

The optically active carboxylic acids can, however, also be crystallized out of the aqueous reaction solution immediately after acidification with an acid to a pH advantageously below 3. This advantageously entails the aqueous solution being concentrated by heating to reduce its volume by 10 to 90%, preferably 20 to 80%, particularly preferably 30 to 70%. The crystallization is preferably carried out with cooling. Temperatures between 0° C. and 15° C. are preferred for the crystallization. It is likewise preferred to work up the optically active carboxylic acids via extraction and, where appropriate, subsequent crystallization.

With these preferred types of workup, the product of the method according to the invention can be isolated in yields of from 60 to 100%, preferably from 80 to 100%, particularly preferably from 90 to 100%, based on the nitrile employed for the reaction. The isolated product has a high chemical purity of >90%, preferably >95%, particularly preferably >98%. In addition, the products have high enantiomeric purity, which may be increased further by crystallization. The products obtained in this way are suitable as starting material for organic syntheses to prepare drugs or agrochemicals or for racemate resolution.

Yet another embodiment of the invention regards a method for achieving herbicide resistance in a plant organism, wherein said plant organism is transformed with an expression cassette comprising a nucleic acid sequence encoding a nitrilase, which at a position corresponding to position 296 in wild-type *Alcaligenes faecalis* nitrilase as described by SEQ ID NO: 2 comprises an amino acid which is not tyrosine, wherein said nucleic acid sequence is under control of a promoter function in said plant organism. Preferably the herbicide is a nitrile herbicide, more preferably 3,5-dibromo-4-hydroxybenzonitrile (Bromoxynil®).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

SEQUENCES

SEQ ID NO: 1 Nucleic acid sequence encoding nitrilase from *Alcaligenes faecalis* specie (DE19848129-A1)
SEQ ID NO: 2 Amino acid sequence encoding nitrilase from *Alcaligenes faecalis* specie (DE19848129-A1)
SEQ ID NO: 3 Nucleic acid sequence encoding nitrilase from *Alcaligenes faecalis* specie (WO 99/64607)
SEQ ID NO: 4 Amino acid sequence encoding nitrilase from *Alcaligenes faecalis* specie (WO 99/6460)
SEQ ID NO: 5 Nucleic acid sequence encoding nitrilase from *Pseudomonas* spec.

SEQ ID NO: 6 Amino acid sequence encoding nitrilase from *Pseudomonas* spec.
SEQ ID NO: 7 Nucleic acid sequence encoding nitrilase from *Rhodococcus rhodochrous* (DE10010149)
SEQ ID NO: 8 Amino acid sequence encoding nitrilase from *Rhodococcus rhodochrous* (DE10010149)

EXAMPLES

Example 1

Production of Modified Nitrilases by Substitution of Y296 Against Other Amino Acids The substitution of tyrosine at position 296 in wild-type *Alcaligenes faecalis* nitrilase as described by SEQ ID NO: 2 was realized by site-directed mutagenesis utilizing overlap-extension PCR. The following approaches were made:

| PCR Reaction No. | Template | Primers | Product Length |
|---|---|---|---|
| 1. | pDHE1650 | Mke122 + Mke214 | ca. 910 bp |
| 2 | pDHE1650 | Mke213 + Mke120 | ca. 210 bp |
| 3 | PCR products 1 + 2 | Mke122 + Mke120 | ca. 1100 bp |

The following primers were used:

| Primer No. | Sequence (5'-3') | Position |
|---|---|---|
| Mke120 | CTCAAGCTTAGGACGGCTCTTGCA (SEQ ID NO: 14) | C-term. primer (Hind III) |
| Mke122 | GGAGATATACATATGCAGACAAG (SEQ ID NO: 15) | N-term. primer (Nde I) |
| Mke213 | CAATGACCCCGTAGGCCACNNNTCCA AACC (SEQ ID NO: 16) | Forward primer for Mutagenesis at position Y296X |
| Mke214 | CTCGGGTTTGGANNNGTGGCCTACGG GGTC (SEQ ID NO: 17) | Reverse primer for mutagenesis at position Y296X |

NNN in the primers indicted above may represent any base (A; T; C; G; wobble primer)

The PCR was carried out using Pfu-Polymerase (Stratagene) using the following temperature program: 95° C. for 3 minutes; 25 cycles with 95° C. for 45 sec., 55° C. for 45 sec, and 72° C. for 2 min. 50 sec.; 72° C. for 10 min.; storage at 4° C. until further usage. All PCR products were purified by agarose gel electrophoresis (E-Gel, Invitrogen) and column chromatography (GFX-Kit, Pharmacia). Products from PCR No. 3 were subsequently digested with NdeI and HindIII, and cloned into a correspondingly digested PDHE vector (DE19848129-A1).

Example 2

Assay for Enzymatic Activity with 2-Chloromandelonitrile

The plasmids generated as described in Example 1 were transformed into *E. coli* TG1 and plated on LB solid medium comprising 100 µg/ml ampicilline. Obtained clones were transferred to 0.2 ml liquid LB-Amp medium and grown over night at 37° C. Part of this culture was used to inoculate 0.2 ml liquid LB-Amp medium comprising 2 g/l L-rhamnose for induction of expression. The cultures were grown over night, harvested and analyzed for their catalytic activity for 2-chloromandelonitrile. For this purpose 90 µl cell suspension (in 10 mM Pipes pH7.2) were added to 85 µl 10 mM Pipes pH7.2 and 25 µl 2-chloromandelonitrile (2-CMN) (48 mM in methanol). After an incubation of 40 min at 50° C. the reaction was terminated by adding HCl. The supernatant was analyzed by HPLC for 2-chloromandelic acid. Clones with the highest activity were isolated, plasmid DNA was prepared therefrom, sequenced and transformed into TG10 comprising pAgro pHSG575 (*E. coli* TG10 is derivative of *E. coli* TG1 comprising a deficiency in the rhamnose-isomerase rhaA; pAgro (pBB541; Tashifumi Tomoyasu et al. (2001) Mol Microbiol 40(2):397-413) and pHSG575 (Takeshita S et al. (1987) Gene 61:63-74) are plasmids for chaperon GroELS coexpression).

After growing in 4 ml scale in liquid LB-Amp further comprising spectinomycine (50 µg/ml), chloramphenicole (10 µg/ml) and—if required for enzyme induction—L-rhamnose (0.5 g/L) and IPTG (0.1 mM), the activity of the above selected clones was verified. FIG. 1 depicts activity of some clones and their sequence in comparison to the unmodified control TG10 pDHE1650 pAgro pHSG575.

Activity is calculated by determining carbonic acid production [µmol/(l*min)]. Specific activity is obtained by normalization with regard to microorganism biomass used in the assay as expressed by the optical density measured at 600 nm (OD600) [mmol/(l*min*OD600)]. "Relative specific activity" is calculated by setting the specific activity obtained for a given standard substrate (e.g., wild-type nitrilase) to 1.0 and transforming the specific activity for other nitrilases by rule of three.

Example 3

Comparison of Substrate Acceptance of Nitrilase (SEQ ID NO: 2) and its Y296C Mutant A pre-culture of *E. coli* TG10 transformed with the pDHE vector comprising an expression cassette for the nitrilase described by SEQ ID NO: 2 (pDHE1650) and its Y296C mutant (produced as described above) were grown in 25 mL liquid LB medium comprising ampicillin (100 µg/ml), spectinomycine (50 µg/ml), chloramphenicole (10 µg/ml) for 23 h at 37° C. under continuous shaking (200 rpm). 10 ml of the resulting culture were used to inoculate 400 mL LB medium comprising ampicillin (100 µg/ml), spectinomycine (50 µg/ml), chloramphenicole (10 µg/ml), 0.1 mM IPTG, and 0.5 g/L Rhamnose and grown for 18 h at 37° C. under continuous shaking (200 rpm). The resulting biomass was harvested and washed using 10 mM Tris/HCl pH 7.0.

Figure 2:
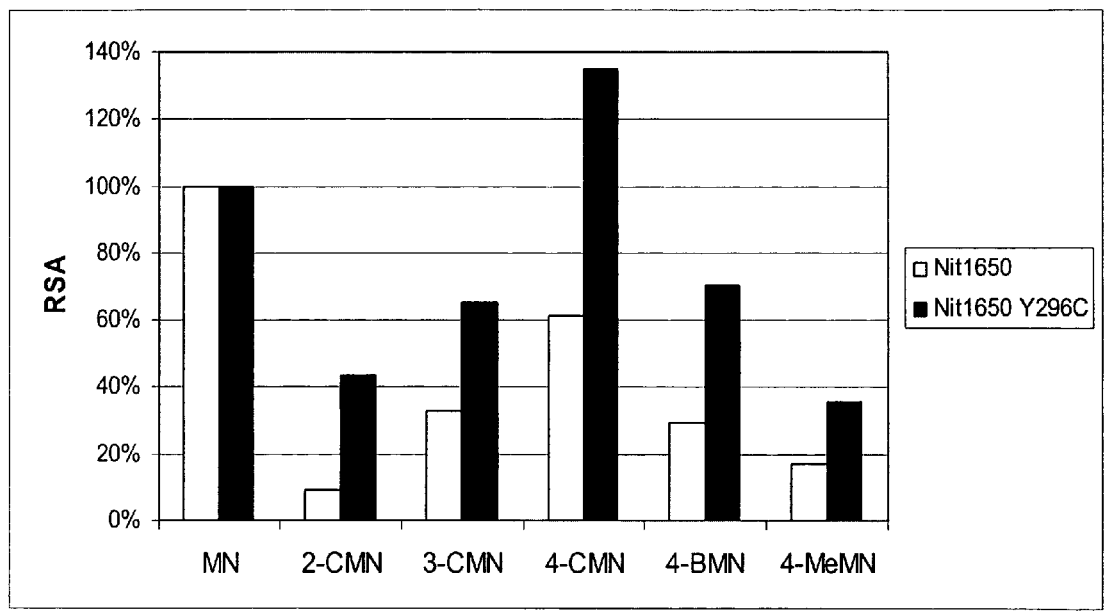
FIG. 2: Comparison of mutant nitrilase Y296C and wild-type nitrilase Y296 with regard to conversion of various arylacetonitriles. y-axis is presenting relative specific activity [RSA]. Specific activity was measured as described below. Relative specific activity was calculated by setting the activity against unsubstituted mandelonitrile at 100%. X-axis is presenting the various tested substrates: MN (mandelonitrile), 2-CMN (2-chlorpmandelonitrile), 3-CMN (3-chloromandelonitrile), 4-CMN (4-R-chlormandelonitrile), 4-BMN (4-bromomandelo-nitrile), and 4-MeMN (4-methylmandelonitrile). The mutant exhibits a significantly higher activity for each of the tested substituted mandelonitriles while activity against unsubstituted mandelonitrile remains unchanged.

Substrate acceptance tests were performed using 25 µl cell suspension/ml in 10 mM PIPES pH7.0/10% MeOH comprising 6 mM of the indicated nitrile at 40° C. for 0.5 h and 2 h, respectively. The reaction was stopped by adding 1 M HCl and the supernatant was analyzed by HPLC. Results are depicted in FIG. 2. It becomes obvious that the mutation at position Y296 results in a broader substrate acceptance for substituted arylacetonitriles. While the unmodified enzyme can convert substituted nitriles with only low activity, the modification results in an increase of activity for each of the tested substituted substrates while activity towards the unsubstituted remains unchanged.

Activity is calculated by determining carbonic acid production [µmol/(l*min)]. Specific activity is obtained by normalization with regard to microorganism biomass used in the assay as expressed by the optical density measured at 600 nm (OD600) [mmol/(l*min*OD600)]. "Relative specific activity" is calculated by setting the specific activity obtained for a given standard substrate (e.g., unsubstituted mandelonitrile) to 100% and transforming the specific activity for other substrates by rule of three.

Example 4

Production of Modified Nitrilases by Substitution of Y296 Against Other Amino Acids 4.1 The substitution of tyrosine Y296 of nitrilase from *Alcaligenes faecalis* ATCC8750 (SEQ.ID NO.4, called "Nit8750_ALCFA") against alanine was realized by site-directed mutagenesis utilizing overlap-extension PCR. The following approaches were made:

| PCR Reaction No. | Template | Primers | Product Length |
|---|---|---|---|
| 1. | pDHE8750 | Mke301 + Mke223 | ca. 1020 bp |
| 2 | pDHE8750 | Mke123 + Mke303 | ca. 470 bp |
| 3 | PCR products 1 + 2 | Mke123 + Mke223 | ca. 1500 bp |

Primer:

| Primer No. | Sequence (5'-3') | Position |
|---|---|---|
| Mke123 | GTTCATCTTTCCCTGGTTG (SEQ ID NO: 18) | N-term. primer (Nde I) |
| Mke223 | GCGTTCACCGACAAACAAC (SEQ ID NO: 19) | C-term. primer (Hind III) |
| Mke301 | GTGGGCCACGCCTCCAAACCCGAG (SEQ ID NO: 20) | Forward primer for mutagenesis at position Y296A |
| Mke303 | CTCGGGTTTGGAGGCGTGGCCCAC (SEQ ID NO: 21) | Reverse primer for mutagenesis at position Y296A |

PCR reactions and cloning were done as described in Example 1. Plasmid-DNA of the obtained clones carried the desired mutation encoding modified nitrilase Nit8750_ALCFA-Y296A as demonstrated by sequencing.

4.2 The substitution of tyrosine Y297 of nitrilase from *Pseudomonas* sp. (SEQ.ID NO.6, called "Nit338_PSESP"; residue Y297 corresponds to Y296 in nitrilases Nit1650_ALCFA and Nit8750_ALCFA) against alanine was performed by site-directed mutagenesis utilizing overlap-extension PCR. The following approaches were made:

| PCR Reaction No. | Template | Primers | Product Length |
|---|---|---|---|
| 1. | pDHE338 | Mke297 + Mke223 | ca. 1020 bp |
| 2 | pDHE338 | Mke123 + Mke299 | ca. 450 bp |
| 3 | PCR products 1 + 2 | Mke123 + Mke223 | ca. 1500 bp |

Primer:

| Primer No. | Sequence (5'-3') | Position |
|---|---|---|
| Mke123 | GTTCATCTTTCCCTGGTTG (SEQ ID NO: 18) | N-term. Primer (Nde I) |
| Mke223 | GCGTTCACCGACAAACAAC (SEQ ID NO: 19) | C-term. primer (Hind III) |
| Mke297 | GTCACGCCTCACGCCCTGATGTGC (SEQ ID NO: 22) | Forward primer for mutagenesis at position Y297A |
| Mke299 | GCACATCAGGGCGTGAGGCGTGAC (SEQ ID NO: 23) | Reverse primer for mutagenesis at position Y297A |

PCR reactions and cloning was done as described in Example 1. Plasmid-DNA of the clones obtained carried the desired mutation encoding modified nitrilase Nit338_PSESP—Y296A as demonstrated by sequencing.

Example 5

Comparison of Substrate Acceptance of Nitrilase Nit8750_ALCFA and its Y296A Mutant, Nit338_PSESP and its Y297A Mutant.

Individual pre-cultures of *E. coli* TG10 transformed with the PDHE vector comprising an expression cassette for the nitrilase described by SEQ ID NO: 4 and its Y296A mutant, SEQ ID NO: 6 and its Y297A mutant, respectively (produced as described above) were grown in 25 mL liquid LB medium comprising ampicillin (100 µg/ml), spectinomycine (50 µg/ml), chloramphenicole (10 µg/ml) for 23 h at 37° C. under continuous shaking (200 rpm). 10 ml each of the resulting culture were used to inoculate individual batches of 400 mL LB medium comprising ampicillin (100 µg/ml), spectinomycine (50 µg/ml), chloramphenicol (10 µg/ml), 0.1 mM IPTG, and 0.5 g/L Rhamnose and grown for 18 h at 37° C. under continuous shaking (200 rpm). The resulting biomass was harvested separately and washed using 10 mM Tris/HCl pH 7.0.

Figure 3:
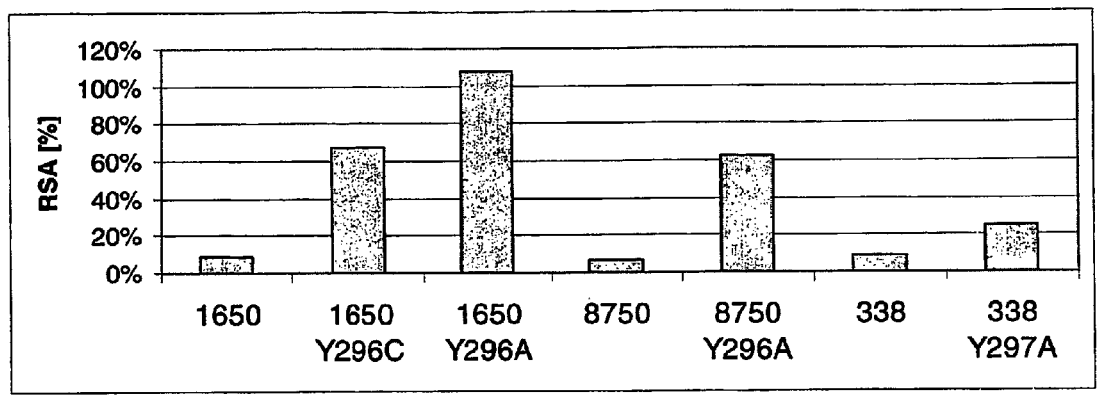
FIG. 3: Comparison of various mutant nitrilases with regard to conversion of 2-chloromandelonitrile. y-axis is presenting relative specific activity [RSA], measured and calculated as described below using mandelonitrile as 100% standard. X-axis is presenting the various tested nitrilases: 1650: Nitrilase from *Alcaligenes faecalis* spec. as described by SEQ ID NO: 2 (wild-type); 1650 Y296C Nitrilase from *Alcaligenes faecalis* spec. as described by SEQ ID NO: 2 but with Y296C variation; 1650 Y296A Nitrilase from *Alcaligenes faecalis* spec. as described by SEQ ID NO: 2 but with Y296A variation; 8750: Nitrilase from *Alcaligenes faecalis* spec. as described by SEQ ID NO: 4 (wild-type); 8750 Y296A Nitrilase from *Alcaligenes faecalis* spec. as described by SEQ ID NO: 4 but with Y296A variation; 338: Nitrilase from *Pseudomonas* spec. by SEQ ID NO: 6 (wildtype); 338 Y297A Nitrilase from *Pseudomonas* spec. as described by SEQ ID NO: 6 but with Y297A variation. All of the tested mutants exhibit a significantly higher activity for 2-chloromandelonitrile than the corresponding wild-type enzymes.

Substrate acceptance tests were performed using 25 µl of the individual cell suspensions/ml in 10 mM PIPES pH7.0/ 10% MeOH comprising 10 mM of mandelonitrile and 2-chloromandelo-nitrile, respectively, at 40° C. for 0.5 h and 2 h, respectively. The reaction was stopped by adding 1 M HCl and the supernatant was analyzed by HPLC. Results are depicted in FIG. 3 as ratios of the specific activities of 2-chloromandelonitile towards mandelonitrile. Calculations were done by setting the specific activity for mandelonitrile of each wild-type nitrilase to 100% and transformating the specific activity for the other nitrilases and for 2-chloromandelonitrile by rule of three.

Mutations at position Y296/Y297 (each corresponding to Y296 in nitrilase from *Alcaligenes faecalis* as described by SEQ ID DO: 2) result in a broader substrate acceptance for substituted arylacetonitriles independent from the wild-type nitrilase. While the unmodified enzyme can convert substituted nitrites with only low activity, the modification results in an increase of activity for each of the tested substituted substrates.

We claim:

1. An isolated polypeptide having nitrilase activity with modified substrate acceptance, comprising at least one sequence selected from the group consisting of a) (K/R/H)XXXDXXGX(X*), (SEQ ID NO: 24)

b) KAINDPVGH(X*), (SEQ ID NO: 9)

c) GH(X*)SRPDV, (SEQ ID NO: 10)

d) DP(A/V)GH(X*)SRPDV(L/T)(S/R)L, (SEQ ID NO: 11) and e) DPAGH(X*)SRPDVLSLLV, (SEQ ID NO: 12)

wherein X* is not tyrosine and is localized at a position corresponding to position 296 in wild-type *Alcaligenes faecalis* nitrilase as described by SEQ ID NO: 2, and wherein said isolated polypeptide comprises an amino acid sequence having at least 80% identity to the amino acid sequence of SEQ ID NO: 2, 4, 6, or 8.

2. The isolated polypeptide of claim 1, wherein said isolated polypeptide comprises at least one sequence selected from the group consisting of a) (K/R)XXXDXXG(H/Y/S)(X*), (SEQ ID NO: 13)

b) KXXXDXXGX(X*), (SEQ ID NO: 25)

c) KAINDPVGH(X*), (SEQ ID NO: 9)

d) GH(X*)SRPDV, (SEQ ID NO: 10)

e) DP(A/V)GH(X*)SRPDV(L/T)(S/R)L, (SEQ ID NO: 11) and f) DPAGH(X*)SRPDVLSLLV, (SEQ ID NO: 12)

wherein X stands for any amino acid and X* represents an amino acid residue which is not tyrosine, and wherein X* is localized at a position corresponding to position 296 in wild-type *Alcaligenes faecalis* nitrilase as described by SEQ ID NO: 2.

3. The isolated polypeptide of claim 1, wherein X* is selected from the group consisting of cysteine, alanine, asparagine, glycine, serine, phenylalanine, and threonine.

4. The isolated polypeptide of claim 1, wherein said isolated polypeptide exhibits a modulated substrate acceptance in comparison to a nitrilase which is identical to said nitrilase but for the amino acid residue at the position corresponding to position 296 in wild-type *Alcaligenes faecalis* nitrilase as described by SEQ ID NO: 2.

5. The isolated polypeptide of claim 1, wherein said isolated polypeptide comprises an amino acid sequence having at least 90% identity to the amino acid sequence of SEQ ID NO: 2, 4, 6, or 8.

6. An isolated nucleic acid molecule comprising a nucleic acid sequence encoding the isolated polypeptide of claim 1.

7. A recombinant expression construct comprising at least one isolated nucleic acid molecule of claim 6.

8. A recombinant expression vector comprising at least one isolated nucleic acid molecule of claim 6.

9. A recombinant organism comprising at least one isolated nucleic acid molecule of claim 6.

10. The recombinant organism of claim 9, wherein said recombinant organism is selected from the group consisting of bacteria, fungi, algae, and plant organism.

11. The recombinant organism of claim 9, wherein the recombinant organism is a bacterium of the genera *Escherichia*, *Rhodococcus*, *Nocardia*, *Streptomyces* or *Mycobacterium*.

12. A method for producing a nitrilase with modulated substrate acceptance comprising substituting in a nitrilase at least a tyrosine at a position corresponding to position 296 in wild-type *Alcaligenes faecalis* nitrilase as described by SEQ ID NO: 2 by another amino acid, wherein said nitrilase comprises an amino acid sequence having at least 80% identity to the amino acid sequence of SEQ ID NO: 2, 4, 6, or 8, and further comprises at least one sequence selected from the group consisting of SEQ ID NO: 9, 10, 11, 12, 13, 24, and 25.

13. A method for modulating substrate acceptance of a nitrilase comprising substituting in a nitrilase at least a tyrosine at a position corresponding to position 296 in wild-type *Alcaligenes faecalis* nitrilase as described by SEQ ID NO: 2 by another amino acid, wherein said nitrilase comprises an amino acid sequence having at least 80% identity to the amino acid sequence of SEQ ID NO: 2, 4, 6, or 8, and further comprises at least one sequence selected from the group consisting of SEQ ID NO: 9, 10, 11, 12, 13, 24, and 25.

14. A method for the production of carbonic acids, wherein a nitrile or a mixture of aldehyde or ketone and cyanide is transformed into the corresponding carbonic acid by action of one or more polypeptides of claim 1.

15. The method of claim 14, wherein at least one nitrile of the general formula I is converted into carboxylic acids of the general formula II

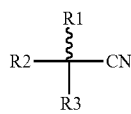
(I)

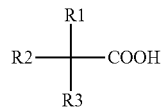
(II)

wherein the substituents $R^1$, $R^2$, $R^3$ may independently of one another be selected from the group consisting of hydrogen, substituted or unsubstituted, branched or unbranched $C_1$-$C_{10}$-alkyl or $C_1$-$C_{10}$-alkoxy, substituted or unsubstituted aryl or heteroaryl, hydroxyl, halogen, $C_1$-$C_{10}$-alkylamino and amino, and wherein at least two of the radicals $R^1$, $R^2$ and $R^3$ are different.

16. The method of claim 14, wherein the nitrile is selected from the group consisting of racemic o-chloromandelonitrile, p-chloromandelonitrile, m-chloromandelonitrile, o-bromomandelonitrile, p-bromomandelonitrile, m-bromomandelonitrile, o-methylmandelonitrile, p-methylmandelonitrile and m-methylmandelonitrile, and a mixture of an corresponding aldehyde of any of the nitriles and cyanide.

17. The method of claim 14, wherein the produced carbonic acid is selected from the group consisting of R-mandelic acid, S-mandelic acid, R-p-chloromandelic acid, S-p-chloromandelic acid, R-m-chloromandelic acid, S-m-chloro mandelic acid, R-o-chloromandelic acid, S-o-chloromandelic acid, S-o-bromomandelic acid, S-p-bromomandelic acid, S-m-bromomandelic acid, S-o-methylmandelic acid, S-p-methylmandelic acid, S-m-methylmandelic acid, R-o-bromomandelic acid, R-p-bromomandelic acid, R-m-bromomandelic acid, R-o-methylmandelic acid, R-p-methylmandelic acid and R-m-methylmandelic acid.

18. A method for achieving herbicide resistance in a plant organism, comprising transforming a plant organism with an expression cassette comprising a nucleic acid sequence encoding a nitrilase under control of a promoter functioning in said plant organism, wherein at a position corresponding to position 296 in wild-type *Alcaligenes faecalis* nitrilase as described by SEQ ID NO: 2 of said nitrilase comprises an amino acid which is not tyrosine, and wherein said nitrilase comprises an amino acid sequence having at least 80% identity to the amino acid sequence of SEQ ID NO: 2, 4, 6, or 8, and further comprises at least one sequence selected from the group consisting of SEQ ID NO: 9, 10, 11, 12, 13, 24, and 25.

19. The isolated polypeptide of claim 1, wherein said isolated polypeptide comprises an amino acid sequence having at least 95% identity to the amino acid sequence of SEQ ID NO: 2, 4, 6, or 8.

* * * * *

SEQUENCE LISTING

<160> NUMBER OF SEQ ID NOS: 25

<210> SEQ ID NO 1
<211> LENGTH: 1071
<212> TYPE: DNA
<213> ORGANISM: Alcaligenes faecalis
<220> FEATURE:
<221> NAME/KEY: CDS
<222> LOCATION: (1)..(1068)
<223> OTHER INFORMATION: coding for nitrilase
<220> FEATURE:
<221> NAME/KEY: variation
<222> LOCATION: (886)..(888)
<223> OTHER INFORMATION: codon for variation for non-tyrosine modification

<400> SEQUENCE: 1

| | | | | | | | | | | | | | | | | |
|---|---|---|---|---|---|---|---|---|---|---|---|---|---|---|---|---|
| atg | aca | aga | aaa | atc | gtc | cgg | gca | gcc | gcc | gta | cag | gcc | gcc | tct | | 48 |
| Met | Gln | Thr | Arg | Lys | Ile | Val | Arg | Ala | Ala | Ala | Val | Gln | Ala | Ala | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ccc | aac | tac | gat | ctg | gca | acg | ggt | gtt | gat | aaa | acc | att | gag | ctg | gct | 96 |
| Pro | Asn | Tyr | Asp | Leu | Ala | Thr | Gly | Val | Asp | Lys | Thr | Ile | Glu | Leu | Ala | |
| | | 20 | | | | | 25 | | | | | 30 | | | | |

| | | | | | | | | | | | | | | | | |
|---|---|---|---|---|---|---|---|---|---|---|---|---|---|---|---|---|
| cgt | cag | gcc | cgc | gat | gag | ggc | tgt | gac | ctg | atc | gtg | ttt | ggt | gaa | acc | 144 |
| Arg | Gln | Ala | Arg | Asp | Glu | Gly | Cys | Asp | Leu | Ile | Val | Phe | Gly | Glu | Thr | |
| | 35 | | | | | 40 | | | | | 45 | | | | | |

| | | | | | | | | | | | | | | | | |
|---|---|---|---|---|---|---|---|---|---|---|---|---|---|---|---|---|
| tgg | ctg | ccc | gga | tat | ccc | ttc | cac | gtc | tgg | ctg | ggc | gca | ccg | gcc | tgg | 192 |
| Trp | Leu | Pro | Gly | Tyr | Pro | Phe | His | Val | Trp | Leu | Gly | Ala | Pro | Ala | Trp | |
| | 50 | | | | 55 | | | | | 60 | | | | | | |

| | | | | | | | | | | | | | | | | |
|---|---|---|---|---|---|---|---|---|---|---|---|---|---|---|---|---|
| tcg | ctg | aaa | tac | agt | gcc | cgc | tac | tat | gcc | aac | tcg | ctc | tcg | ctg | gac | 240 |
| Ser | Leu | Lys | Tyr | Ser | Ala | Arg | Tyr | Tyr | Ala | Asn | Ser | Leu | Ser | Leu | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agt | gca | gag | ttt | caa | cgc | att | gcc | cag | gcc | gca | cgg | acc | ttg | ggt | att | 288 |
| Ser | Ala | Glu | Phe | Gln | Arg | Ile | Ala | Gln | Ala | Ala | Arg | Thr | Leu | Gly | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| ttc | atc | gca | ctg | ggt | tat | agc | gag | cgc | agc | ggc | ggc | agc | ctt | tac | ctg | 336 |
| Phe | Ile | Ala | Leu | Gly | Tyr | Ser | Glu | Arg | Ser | Gly | Gly | Ser | Leu | Tyr | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| ggc | caa | tgc | ctg | atc | gac | gac | aag | ggc | gag | atg | ctg | tgg | tcg | cgt | cgc | 384 |
| Gly | Gln | Cys | Leu | Ile | Asp | Asp | Lys | Gly | Glu | Met | Leu | Trp | Ser | Arg | Arg | |
| | | 115 | | | | | 120 | | | | | 125 | | | | |

| | | | | | | | | | | | | | | | | |
|---|---|---|---|---|---|---|---|---|---|---|---|---|---|---|---|---|
| aaa | ctc | aaa | ccc | acg | cat | gta | gag | cgc | acc | gta | ttt | ggt | gaa | ggt | tat | 432 |
| Lys | Leu | Lys | Pro | Thr | His | Val | Glu | Arg | Thr | Val | Phe | Gly | Glu | Gly | Tyr | |
| | 130 | | | | | 135 | | | | | 140 | | | | | |

| | | | | | | | | | | | | | | | | |
|---|---|---|---|---|---|---|---|---|---|---|---|---|---|---|---|---|
| gcc | cgt | gat | ctg | att | gtg | tcc | gac | aca | gaa | ctg | gga | cgc | gtc | ggt | gct | 480 |
| Ala | Arg | Asp | Leu | Ile | Val | Ser | Asp | Thr | Glu | Leu | Gly | Arg | Val | Gly | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cta | tgc | tgc | tgg | gag | cat | ttg | tcg | ccc | ttg | agc | aag | tac | gcg | ctg | tac | 528 |
| Leu | Cys | Cys | Trp | Glu | His | Leu | Ser | Pro | Leu | Ser | Lys | Tyr | Ala | Leu | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| tcc | cag | cat | gaa | gcc | att | cac | att | gct | gcc | tgg | ccg | tcg | ttt | tcg | cta | 576 |
| Ser | Gln | His | Glu | Ala | Ile | His | Ile | Ala | Ala | Trp | Pro | Ser | Phe | Ser | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| tac | agc | gaa | cag | gcc | cac | gcc | ctc | agt | gcc | aag | gtg | aac | atg | gct | gcc | 624 |
| Tyr | Ser | Glu | Gln | Ala | His | Ala | Leu | Ser | Ala | Lys | Val | Asn | Met | Ala | Ala | |
| | | 195 | | | | | 200 | | | | | 205 | | | | |

| | | | | | | | | | | | | | | | | |
|---|---|---|---|---|---|---|---|---|---|---|---|---|---|---|---|---|
| tcg | caa | atc | tat | tcg | gtt | gaa | ggc | cag | tgc | ttt | acc | atc | gcc | gcc | agc | 672 |
| Ser | Gln | Ile | Tyr | Ser | Val | Glu | Gly | Gln | Cys | Phe | Thr | Ile | Ala | Ala | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| agt | gtg | gtc | acc | caa | gag | acg | cta | gac | atg | ctg | gaa | gtg | ggt | gaa | cac | 720 |
| Ser | Val | Val | Thr | Gln | Glu | Thr | Leu | Asp | Met | Leu | Glu | Val | Gly | Glu | His | |
| 225 | | | | | 230 | | | | | 235 | | | | | 240 | |

```
aac gcc ccc ttg ctg aaa gtg ggc ggc ggc agt tcc atg att ttt gcg    768
Asn Ala Pro Leu Leu Lys Val Gly Gly Gly Ser Ser Met Ile Phe Ala
            245                 250                 255 ccg gac gga cgc aca ctg gct ccc tac ctg cct cac gat gcc gag ggc    816
Pro Asp Gly Arg Thr Leu Ala Pro Tyr Leu Pro His Asp Ala Glu Gly
            260                 265                 270 ttg atc att gcc gat ctg aat atg gag gag att gcc ttc gcc aaa gcg    864
Leu Ile Ile Ala Asp Leu Asn Met Glu Glu Ile Ala Phe Ala Lys Ala
            275                 280                 285 atc aat gac ccc gta ggc cac tat tcc aaa ccc gag gcc acc cgt ctg    912
Ile Asn Asp Pro Val Gly His Tyr Ser Lys Pro Glu Ala Thr Arg Leu
            290                 295                 300 gtg ctg gac ttg ggg cac cga gac ccc atg act cgg gtg cac tcc aaa    960
Val Leu Asp Leu Gly His Arg Asp Pro Met Thr Arg Val His Ser Lys
305                 310                 315                 320 agc gtg acc agg gaa gag gct ccc gag caa ggt gtg caa agc aag att   1008
Ser Val Thr Arg Glu Glu Ala Pro Glu Gln Gly Val Gln Ser Lys Ile
            325                 330                 335 gcc tca gtc gct atc agc cat cca cag gac tcg gac aca ctg cta gtg   1056
Ala Ser Val Ala Ile Ser His Pro Gln Asp Ser Asp Thr Leu Leu Val
            340                 345                 350 caa gag ccg tcc tga                                                1071
Gln Glu Pro Ser
            355
```

<210> SEQ ID NO 2
<211> LENGTH: 356
<212> TYPE: PRT
<213> ORGANISM: Alcaligenes faecalis

<400> SEQUENCE: 2

```
Met Gln Thr Arg Lys Ile Val Arg Ala Ala Val Gln Ala Ala Ser
 1               5                  10                  15

Pro Asn Tyr Asp Leu Ala Thr Gly Val Asp Lys Thr Ile Glu Leu Ala
                20                  25                  30

Arg Gln Ala Arg Asp Glu Gly Cys Asp Leu Ile Val Phe Gly Glu Thr
            35                  40                  45

Trp Leu Pro Gly Tyr Pro Phe His Val Trp Leu Gly Ala Pro Ala Trp
        50                  55                  60

Ser Leu Lys Tyr Ser Ala Arg Tyr Tyr Ala Asn Ser Leu Ser Leu Asp
65                  70                  75                  80

Ser Ala Glu Phe Gln Arg Ile Ala Gln Ala Ala Arg Thr Leu Gly Ile
                85                  90                  95

Phe Ile Ala Leu Gly Tyr Ser Glu Arg Ser Gly Gly Ser Leu Tyr Leu
            100                 105                 110

Gly Gln Cys Leu Ile Asp Asp Lys Gly Glu Met Leu Trp Ser Arg Arg
        115                 120                 125

Lys Leu Lys Pro Thr His Val Glu Arg Thr Val Phe Gly Glu Gly Tyr
    130                 135                 140

Ala Arg Asp Leu Ile Val Ser Asp Thr Glu Leu Gly Arg Val Gly Ala
145                 150                 155                 160

Leu Cys Cys Trp Glu His Leu Ser Pro Leu Ser Lys Tyr Ala Leu Tyr
                165                 170                 175

Ser Gln His Glu Ala Ile His Ile Ala Ala Trp Pro Ser Phe Ser Leu
            180                 185                 190

Tyr Ser Glu Gln Ala His Ala Leu Ser Ala Lys Val Asn Met Ala Ala
        195                 200                 205
```

-continued

```
Ser Gln Ile Tyr Ser Val Glu Gly Gln Cys Phe Thr Ile Ala Ala Ser
    210                 215                 220

Ser Val Val Thr Gln Glu Thr Leu Asp Met Leu Glu Val Gly Glu His
225                 230                 235                 240

Asn Ala Pro Leu Leu Lys Val Gly Gly Ser Ser Met Ile Phe Ala
                245                 250                 255

Pro Asp Gly Arg Thr Leu Ala Pro Tyr Leu Pro His Asp Ala Glu Gly
                260                 265                 270

Leu Ile Ile Ala Asp Leu Asn Met Glu Glu Ile Ala Phe Ala Lys Ala
            275                 280                 285

Ile Asn Asp Pro Val Gly His Tyr Ser Lys Pro Glu Ala Thr Arg Leu
        290                 295                 300

Val Leu Asp Leu Gly His Arg Asp Pro Met Thr Arg Val His Ser Lys
305                 310                 315                 320

Ser Val Thr Arg Glu Glu Ala Pro Glu Gln Gly Val Gln Ser Lys Ile
                325                 330                 335

Ala Ser Val Ala Ile Ser His Pro Gln Asp Ser Asp Thr Leu Leu Val
                340                 345                 350

Gln Glu Pro Ser
        355
```

<210> SEQ ID NO 3
<211> LENGTH: 1071
<212> TYPE: DNA
<213> ORGANISM: Alcaligenes faecalis
<220> FEATURE:
<221> NAME/KEY: CDS
<222> LOCATION: (1)..(1068)
<223> OTHER INFORMATION: coding for nitrilase
<220> FEATURE:
<221> NAME/KEY: variation
<222> LOCATION: (886)..(888)
<223> OTHER INFORMATION: codon for variation for non-tyrosine
    modification

<400> SEQUENCE: 3

```
atg cag aca aga aaa atc gtc cgg gca gcc gcc gta cag gcc gcc tct    48
Met Gln Thr Arg Lys Ile Val Arg Ala Ala Ala Val Gln Ala Ala Ser
  1               5                  10                  15 ccc aac tac gat ctg gca acg ggt gtt gat aaa acc att gag ctg gct    96
Pro Asn Tyr Asp Leu Ala Thr Gly Val Asp Lys Thr Ile Glu Leu Ala
             20                  25                  30 cgt cag gcc cgc gat gag ggc tgt gac ctg atc gtg ttt ggt gaa acc   144
Arg Gln Ala Arg Asp Glu Gly Cys Asp Leu Ile Val Phe Gly Glu Thr
         35                  40                  45 tgg ctg ccc ggc tat ccc ttc cac gtc tgg ctg ggc gca ccg gcc tgg   192
Trp Leu Pro Gly Tyr Pro Phe His Val Trp Leu Gly Ala Pro Ala Trp
     50                  55                  60 tcg ctg aaa tac agt gcc cgc tac tat gcc aac tcg ctc tcg ctg gac   240
Ser Leu Lys Tyr Ser Ala Arg Tyr Tyr Ala Asn Ser Leu Ser Leu Asp
 65                  70                  75                  80 agt gca gag ttt caa cgc att gcc cag gcc gca cgg acc ttg ggt att   288
Ser Ala Glu Phe Gln Arg Ile Ala Gln Ala Ala Arg Thr Leu Gly Ile
                 85                  90                  95 ttc atc gca ctg ggt tat agc gag cgc agc ggc ggc agc ctt tac ctg   336
Phe Ile Ala Leu Gly Tyr Ser Glu Arg Ser Gly Gly Ser Leu Tyr Leu
            100                 105                 110 ggc caa tgc ctg atc gac gac aag ggc cag atg ctg tgg tcg cgt cgc   384
Gly Gln Cys Leu Ile Asp Asp Lys Gly Gln Met Leu Trp Ser Arg Arg
        115                 120                 125 aaa ctc aaa cct aca cat gtt gag cgc acc gtg ttt ggt gaa ggt tat   432
```

```
Lys Leu Lys Pro Thr His Val Glu Arg Thr Val Phe Gly Glu Gly Tyr
        130                 135                 140 gcc cga gat ctg att gtg tcc gac acc gag ctg ggc cgc gtc ggt gcc    480
Ala Arg Asp Leu Ile Val Ser Asp Thr Glu Leu Gly Arg Val Gly Ala
145                 150                 155                 160 ctg tgc tgc tgg gag cac ctg tcc ccc ttg agc aag tac gcg ctg tac    528
Leu Cys Cys Trp Glu His Leu Ser Pro Leu Ser Lys Tyr Ala Leu Tyr
                165                 170                 175 tcc cag cac gaa gcc att cac att gcc gcc tgg ccg tcc ttt tcg ctg    576
Ser Gln His Glu Ala Ile His Ile Ala Ala Trp Pro Ser Phe Ser Leu
            180                 185                 190 tac agc gaa cag gcc cat gcg ctc agc gcc aag gtg aac atg gct gcc    624
Tyr Ser Glu Gln Ala His Ala Leu Ser Ala Lys Val Asn Met Ala Ala
        195                 200                 205 tcg caa atc tat tcg gtt gaa ggc cag tgc ttt acc atc gcc gcc agc    672
Ser Gln Ile Tyr Ser Val Glu Gly Gln Cys Phe Thr Ile Ala Ala Ser
210                 215                 220 agt gtc gtc acc cag gag aca ctg gac atg ctg gaa gta ggt gaa cac    720
Ser Val Val Thr Gln Glu Thr Leu Asp Met Leu Glu Val Gly Glu His
225                 230                 235                 240 aac gcc tcc ctg ctg aaa gtg ggc ggc ggc agt tcc atg att ttt gcg    768
Asn Ala Ser Leu Leu Lys Val Gly Gly Gly Ser Ser Met Ile Phe Ala
                245                 250                 255 ccg gac gga cgc aca ttg gct ccc tac ctg cca cac gat gcc gaa ggc    816
Pro Asp Gly Arg Thr Leu Ala Pro Tyr Leu Pro His Asp Ala Glu Gly
            260                 265                 270 ctg atc att gcc gat ctg aac atg gaa gaa att gcc ttc gcc aag gcg    864
Leu Ile Ile Ala Asp Leu Asn Met Glu Glu Ile Ala Phe Ala Lys Ala
        275                 280                 285 atc aac gac cct gtg ggc cac tac tcc aaa ccc gag gcc acc cgt ctg    912
Ile Asn Asp Pro Val Gly His Tyr Ser Lys Pro Glu Ala Thr Arg Leu
290                 295                 300 gta ctg gac ctg ggg cac cgt gag ccc atg act cgg gtg cat tcc aaa    960
Val Leu Asp Leu Gly His Arg Glu Pro Met Thr Arg Val His Ser Lys
305                 310                 315                 320 agc gtg atc cag gaa gaa gct ccc gag ccg cac gtg caa agt acg gct   1008
Ser Val Ile Gln Glu Glu Ala Pro Glu Pro His Val Gln Ser Thr Ala
                325                 330                 335 gcg ccc gtc gcc gtc agc cag act cag gac tcg gat acg cta ctg gtg   1056
Ala Pro Val Ala Val Ser Gln Thr Gln Asp Ser Asp Thr Leu Leu Val
            340                 345                 350 caa gaa ccg tcc tga                                                1071
Gln Glu Pro Ser
        355

<210> SEQ ID NO 4
<211> LENGTH: 356
<212> TYPE: PRT
<213> ORGANISM: Alcaligenes faecalis

<400> SEQUENCE: 4

Met Gln Thr Arg Lys Ile Val Arg Ala Ala Val Gln Ala Ala Ser
 1               5                  10                  15

Pro Asn Tyr Asp Leu Ala Thr Gly Val Asp Lys Thr Ile Glu Leu Ala
                20                  25                  30

Arg Gln Ala Arg Asp Glu Gly Cys Asp Leu Ile Val Phe Gly Glu Thr
            35                  40                  45

Trp Leu Pro Gly Tyr Pro Phe His Val Trp Leu Gly Ala Pro Ala Trp
        50                  55                  60

Ser Leu Lys Tyr Ser Ala Arg Tyr Tyr Ala Asn Ser Leu Ser Leu Asp
```

```
                65                  70                  75                  80
Ser Ala Glu Phe Gln Arg Ile Ala Gln Ala Ala Arg Thr Leu Gly Ile
                    85                  90                  95

Phe Ile Ala Leu Gly Tyr Ser Glu Arg Ser Gly Gly Ser Leu Tyr Leu
            100                 105                 110

Gly Gln Cys Leu Ile Asp Asp Lys Gly Gln Met Leu Trp Ser Arg Arg
        115                 120                 125

Lys Leu Lys Pro Thr His Val Glu Arg Thr Val Phe Gly Glu Gly Tyr
    130                 135                 140

Ala Arg Asp Leu Ile Val Ser Asp Thr Glu Leu Gly Arg Val Gly Ala
145                 150                 155                 160

Leu Cys Cys Trp Glu His Leu Ser Pro Leu Ser Lys Tyr Ala Leu Tyr
                165                 170                 175

Ser Gln His Glu Ala Ile His Ile Ala Ala Trp Pro Ser Phe Ser Leu
                180                 185                 190

Tyr Ser Glu Gln Ala His Ala Leu Ser Ala Lys Val Asn Met Ala Ala
            195                 200                 205

Ser Gln Ile Tyr Ser Val Glu Gly Gln Cys Phe Thr Ile Ala Ala Ser
        210                 215                 220

Ser Val Val Thr Gln Glu Thr Leu Asp Met Leu Glu Val Gly Glu His
225                 230                 235                 240

Asn Ala Ser Leu Leu Lys Val Gly Gly Ser Ser Met Ile Phe Ala
                245                 250                 255

Pro Asp Gly Arg Thr Leu Ala Pro Tyr Leu Pro His Asp Ala Glu Gly
                260                 265                 270

Leu Ile Ile Ala Asp Leu Asn Met Glu Glu Ile Ala Phe Ala Lys Ala
            275                 280                 285

Ile Asn Asp Pro Val Gly His Tyr Ser Lys Pro Glu Ala Thr Arg Leu
        290                 295                 300

Val Leu Asp Leu Gly His Arg Glu Pro Met Thr Arg Val His Ser Lys
305                 310                 315                 320

Ser Val Ile Gln Glu Glu Ala Pro Glu Pro His Val Gln Ser Thr Ala
                325                 330                 335

Ala Pro Val Ala Val Ser Gln Thr Gln Asp Ser Asp Thr Leu Leu Val
                340                 345                 350

Gln Glu Pro Ser
        355

<210> SEQ ID NO 5
<211> LENGTH: 1059
<212> TYPE: DNA
<213> ORGANISM: Pseudomonas sp.
<220> FEATURE:
<221> NAME/KEY: CDS
<222> LOCATION: (1)..(1056)
<223> OTHER INFORMATION: coding for nitrilase
<220> FEATURE:
<221> NAME/KEY: variation
<222> LOCATION: (889)..(891)
<223> OTHER INFORMATION: codon for variation for non-tyrosine
    modification

<400> SEQUENCE: 5 atg acg gtg cat aaa aaa cag tac aaa gta gcc gcg gtg cag gcc gcc      48
Met Thr Val His Lys Lys Gln Tyr Lys Val Ala Ala Val Gln Ala Ala
1               5                   10                  15 cct gcg ttc ctc gac ctg gaa gct ggc gtg gcc aaa gcc atc gga ctg      96
Pro Ala Phe Leu Asp Leu Glu Ala Gly Val Ala Lys Ala Ile Gly Leu
            20                  25                  30
```

| | |
|---|---|
| att gct cag gcg gcg gct gag ggt gcc tca ctg gtc gct ttc ccc gaa<br>Ile Ala Gln Ala Ala Ala Glu Gly Ala Ser Leu Val Ala Phe Pro Glu<br>     35                   40                     45 | 144 |
| gcg tgg ctg ccg ggg tat ccc tgg tgg atc tgg ctg gac tcc ccg gcc<br>Ala Trp Leu Pro Gly Tyr Pro Trp Trp Ile Trp Leu Asp Ser Pro Ala<br>    50                    55                    60 | 192 |
| ggc ggc atg cgc ttc gtc cag cgc aac ttc gac aat gct ctg gag gtc<br>Gly Gly Met Arg Phe Val Gln Arg Asn Phe Asp Asn Ala Leu Glu Val<br>65                    70                    75                    80 | 240 |
| ggc agc gaa ccc ttc gag cgg ctc tgc agg gct gcg gca cag cac aaa<br>Gly Ser Glu Pro Phe Glu Arg Leu Cys Arg Ala Ala Ala Gln His Lys<br>                   85                    90                   95 | 288 |
| atc tac gtc gta ctg ggc ttc act gaa cgc tct ggc ggc acc ttg tat<br>Ile Tyr Val Val Leu Gly Phe Thr Glu Arg Ser Gly Gly Thr Leu Tyr<br>            100                    105                 110 | 336 |
| ttg gct cag gcg atc att gat gat tgc ggt cgg gta gtc gcc aca cgg<br>Leu Ala Gln Ala Ile Ile Asp Asp Cys Gly Arg Val Val Ala Thr Arg<br>         115                    120                 125 | 384 |
| cgt aag ctc aag ccg act cac gtg gag cgc tca gtc tac gga gaa ggc<br>Arg Lys Leu Lys Pro Thr His Val Glu Arg Ser Val Tyr Gly Glu Gly<br>130                    135                 140 | 432 |
| gac ggt agt gac ctt gct gtg cat gac act acc ttg ggt cgc tta ggt<br>Asp Gly Ser Asp Leu Ala Val His Asp Thr Thr Leu Gly Arg Leu Gly<br>145                  150                 155                 160 | 480 |
| gcc ttg tgc tgc gcg gag cat atc cag ccg ctg tcc aag tac gcc atg<br>Ala Leu Cys Cys Ala Glu His Ile Gln Pro Leu Ser Lys Tyr Ala Met<br>                 165                 170               175 | 528 |
| tac gct cag cac gaa cag gta cat atc gcg gcc tgg cct agc ttt tcg<br>Tyr Ala Gln His Glu Gln Val His Ile Ala Ala Trp Pro Ser Phe Ser<br>             180                    185                 190 | 576 |
| gta tac cgg ggg gct gcg ttt caa ctg agc gcc caa gcc aat aat gcc<br>Val Tyr Arg Gly Ala Ala Phe Gln Leu Ser Ala Gln Ala Asn Asn Ala<br>        195                    200                 205 | 624 |
| gcc tcg caa gtc tac gca ctg gaa ggt cag tgt ttt gtg ctg gcg cca<br>Ala Ser Gln Val Tyr Ala Leu Glu Gly Gln Cys Phe Val Leu Ala Pro<br>210                    215                 220 | 672 |
| tgc gcc acg gtg tcc aaa gaa atg ctc gac gaa ctg att gat tct ccg<br>Cys Ala Thr Val Ser Lys Glu Met Leu Asp Glu Leu Ile Asp Ser Pro<br>225                  230                 235                 240 | 720 |
| gcc aag gct gag ctg ctg ctg gaa ggt ggc ggc ttc gcg atg atc tac<br>Ala Lys Ala Glu Leu Leu Leu Glu Gly Gly Gly Phe Ala Met Ile Tyr<br>             245                    250                 255 | 768 |
| ggc ccg gat ggc gca ccg ctg tgt acg cca ttg gcg gaa aca gag gag<br>Gly Pro Asp Gly Ala Pro Leu Cys Thr Pro Leu Ala Glu Thr Glu Glu<br>        260                    265                 270 | 816 |
| ggc att ctc tat gcg gat atc gac ttg ggg gtg atc ggg gtg gcc aaa<br>Gly Ile Leu Tyr Ala Asp Ile Asp Leu Gly Val Ile Gly Val Ala Lys<br>        275                    280                 285 | 864 |
| gct gcc tac gac ccg gtt ggt cac tat tca cgc cct gat gtg ctg cgg<br>Ala Ala Tyr Asp Pro Val Gly His Tyr Ser Arg Pro Asp Val Leu Arg<br>290                    295                 300 | 912 |
| ttg ctg gtc aac cgg gag cca atg acg cgt gtg cat tat gtt cag ccg<br>Leu Leu Val Asn Arg Glu Pro Met Thr Arg Val His Tyr Val Gln Pro<br>305                  310                 315                 320 | 960 |
| cag tcg tta ccg gag aca tcg gtg ttg gcg ttc ggt gcg gga gcg gat<br>Gln Ser Leu Pro Glu Thr Ser Val Leu Ala Phe Gly Ala Gly Ala Asp<br>             325                    330                 335 | 1008 |
| gcc atc aga agt gag gag aac cca gaa gag caa ggc gac aag gga tcc<br>Ala Ile Arg Ser Glu Glu Asn Pro Glu Glu Gln Gly Asp Lys Gly Ser<br>        340                    345                 350 | 1056 |

<210> SEQ ID NO 6
<211> LENGTH: 352
<212> TYPE: PRT
<213> ORGANISM: Pseudomonas sp.

<400> SEQUENCE: 6

Met Thr Val His Lys Lys Gln Tyr Lys Val Ala Ala Val Gln Ala Ala
1               5                   10                  15

Pro Ala Phe Leu Asp Leu Glu Ala Gly Val Ala Lys Ala Ile Gly Leu
            20                  25                  30

Ile Ala Gln Ala Ala Ala Glu Gly Ala Ser Leu Val Ala Phe Pro Glu
        35                  40                  45

Ala Trp Leu Pro Gly Tyr Pro Trp Trp Ile Trp Leu Asp Ser Pro Ala
    50                  55                  60

Gly Gly Met Arg Phe Val Gln Arg Asn Phe Asp Asn Ala Leu Glu Val
65                  70                  75                  80

Gly Ser Glu Pro Phe Glu Arg Leu Cys Arg Ala Ala Gln His Lys
                85                  90                  95

Ile Tyr Val Val Leu Gly Phe Thr Glu Arg Ser Gly Gly Thr Leu Tyr
            100                 105                 110

Leu Ala Gln Ala Ile Ile Asp Asp Cys Gly Arg Val Val Ala Thr Arg
        115                 120                 125

Arg Lys Leu Lys Pro Thr His Val Glu Arg Ser Val Tyr Gly Glu Gly
    130                 135                 140

Asp Gly Ser Asp Leu Ala Val His Asp Thr Thr Leu Gly Arg Leu Gly
145                 150                 155                 160

Ala Leu Cys Cys Ala Glu His Ile Gln Pro Leu Ser Lys Tyr Ala Met
                165                 170                 175

Tyr Ala Gln His Glu Gln Val His Ile Ala Ala Trp Pro Ser Phe Ser
            180                 185                 190

Val Tyr Arg Gly Ala Ala Phe Gln Leu Ser Ala Gln Ala Asn Asn Ala
        195                 200                 205

Ala Ser Gln Val Tyr Ala Leu Glu Gly Gln Cys Phe Val Leu Ala Pro
    210                 215                 220

Cys Ala Thr Val Ser Lys Glu Met Leu Asp Glu Leu Ile Asp Ser Pro
225                 230                 235                 240

Ala Lys Ala Glu Leu Leu Leu Glu Gly Gly Gly Phe Ala Met Ile Tyr
                245                 250                 255

Gly Pro Asp Gly Ala Pro Leu Cys Thr Pro Leu Ala Glu Thr Glu Glu
            260                 265                 270

Gly Ile Leu Tyr Ala Asp Ile Asp Leu Gly Val Ile Gly Val Ala Lys
        275                 280                 285

Ala Ala Tyr Asp Pro Val Gly His Tyr Ser Arg Pro Asp Val Leu Arg
    290                 295                 300

Leu Leu Val Asn Arg Glu Pro Met Thr Arg Val His Tyr Val Gln Pro
305                 310                 315                 320

Gln Ser Leu Pro Glu Thr Ser Val Leu Ala Phe Gly Ala Gly Ala Asp
                325                 330                 335

Ala Ile Arg Ser Glu Glu Asn Pro Glu Glu Gln Gly Asp Lys Gly Ser
            340                 345                 350

<210> SEQ ID NO 7
<211> LENGTH: 1101

```
<212> TYPE: DNA
<213> ORGANISM: Rhodococcus rhodochrous
<220> FEATURE:
<221> NAME/KEY: CDS
<222> LOCATION: (1)..(1098)
<223> OTHER INFORMATION: coding for nitrilase
<220> FEATURE:
<221> NAME/KEY: variation
<222> LOCATION: (892)..(894)
<223> OTHER INFORMATION: codon for variation for non-tyrosine
      modification

<400> SEQUENCE: 7 atg gtc gaa tac aca aac aca ttc aaa gtt gct gcg gtg cag gca cag      48
Met Val Glu Tyr Thr Asn Thr Phe Lys Val Ala Ala Val Gln Ala Gln
 1               5                  10                  15 cct gtg tgg ttc gac gcg gcc aaa acg gtc gac aag acc gtg tcc atc      96
Pro Val Trp Phe Asp Ala Ala Lys Thr Val Asp Lys Thr Val Ser Ile
             20                  25                  30 atc gcg gaa gca gcc cgg aac ggg tgc gag ctc gtt gcg ttt ccc gag     144
Ile Ala Glu Ala Ala Arg Asn Gly Cys Glu Leu Val Ala Phe Pro Glu
         35                  40                  45 gta ttc atc ccg ggg tac ccg tac cac atc tgg gtc gac agc ccg ctc     192
Val Phe Ile Pro Gly Tyr Pro Tyr His Ile Trp Val Asp Ser Pro Leu
     50                  55                  60 gcc gga atg gcg aag ttc gcc gtg cgc tac cac gag aat tcc ctg acg     240
Ala Gly Met Ala Lys Phe Ala Val Arg Tyr His Glu Asn Ser Leu Thr
 65                  70                  75                  80 atg gac agc ccg cac gta cag cgg ttg ctc gat gcc gcc cgc gac cac     288
Met Asp Ser Pro His Val Gln Arg Leu Leu Asp Ala Ala Arg Asp His
                 85                  90                  95 aac atc gcc gta gtg gtg gga atc agc gag cgg gat ggc ggc agc ttg     336
Asn Ile Ala Val Val Val Gly Ile Ser Glu Arg Asp Gly Gly Ser Leu
            100                 105                 110 tac atg acc cag ctc atc atc gac gcc gat ggg caa ctg gtc gcc cga     384
Tyr Met Thr Gln Leu Ile Ile Asp Ala Asp Gly Gln Leu Val Ala Arg
        115                 120                 125 cgc cgc aag ctc aag ccc acc cac gtc gag cgt tcg gta tac gga gaa     432
Arg Arg Lys Leu Lys Pro Thr His Val Glu Arg Ser Val Tyr Gly Glu
    130                 135                 140 gga aac ggc tcg gat atc tcc gtg tac gac atg cct ttc gca cgg ctt     480
Gly Asn Gly Ser Asp Ile Ser Val Tyr Asp Met Pro Phe Ala Arg Leu
145                 150                 155                 160 ggc gcg ctc aac tgc tgg gag cat ttc cag acg ctc acc aag tac gca     528
Gly Ala Leu Asn Cys Trp Glu His Phe Gln Thr Leu Thr Lys Tyr Ala
                165                 170                 175 atg tac tcg atg cac gag cag gtg cac gtc gcg agc tgg cct ggc atg     576
Met Tyr Ser Met His Glu Gln Val His Val Ala Ser Trp Pro Gly Met
            180                 185                 190 tcg ctg tac cag ccg gag gtc ccc gca ttc ggt gtc gat gcc cag ctc     624
Ser Leu Tyr Gln Pro Glu Val Pro Ala Phe Gly Val Asp Ala Gln Leu
        195                 200                 205 acg gcc acg cgt atg tac gca ctc gag gga caa acc ttc gtg gtc tgc     672
Thr Ala Thr Arg Met Tyr Ala Leu Glu Gly Gln Thr Phe Val Val Cys
    210                 215                 220 acc acc cag gtg gtc aca ccg gag gcc cac gag ttc ttc tgc gag aac     720
Thr Thr Gln Val Val Thr Pro Glu Ala His Glu Phe Phe Cys Glu Asn
225                 230                 235                 240 gag gaa cag cga aag ttg atc ggc cga ggc gga ggt ttc gcg cgc atc     768
Glu Glu Gln Arg Lys Leu Ile Gly Arg Gly Gly Gly Phe Ala Arg Ile
                245                 250                 255 atc ggg ccc gac ggc cgc gat ctc gca act cct ctc gcc gaa gat gag     816
Ile Gly Pro Asp Gly Arg Asp Leu Ala Thr Pro Leu Ala Glu Asp Glu
```

```
                    260                 265                 270
gag ggg atc ctc tac gcc gac atc gat ctg tct gcg atc acc ttg gcg    864
Glu Gly Ile Leu Tyr Ala Asp Ile Asp Leu Ser Ala Ile Thr Leu Ala
        275                 280                 285 aag cag gcc gct gac ccc gtg ggc cac tac tca cgg ccg gat gtg ctg    912
Lys Gln Ala Ala Asp Pro Val Gly His Tyr Ser Arg Pro Asp Val Leu
    290                 295                 300 tcg ctg aac ttc aac cag cgc cgc acc acg ccc gtc aac acc cca ctt    960
Ser Leu Asn Phe Asn Gln Arg Arg Thr Thr Pro Val Asn Thr Pro Leu
305                 310                 315                 320 tcc acc atc cat gcc acg cac acg ttc gtg ccg cag ttc ggg gca ctc    1008
Ser Thr Ile His Ala Thr His Thr Phe Val Pro Gln Phe Gly Ala Leu
                325                 330                 335 gac ggc gtc cgt gag ctc aac gga gcg gac gaa cag cgc gca ttg ccc    1056
Asp Gly Val Arg Glu Leu Asn Gly Ala Asp Glu Gln Arg Ala Leu Pro
            340                 345                 350 tcc aca cat tcc gac gag acg gac cgg gcg aca gcc acc ctc tga        1101
Ser Thr His Ser Asp Glu Thr Asp Arg Ala Thr Ala Thr Leu
        355                 360                 365

<210> SEQ ID NO 8
<211> LENGTH: 366
<212> TYPE: PRT
<213> ORGANISM: Rhodococcus rhodochrous

<400> SEQUENCE: 8

Met Val Glu Tyr Thr Asn Thr Phe Lys Val Ala Ala Val Gln Ala Gln
 1               5                  10                  15

Pro Val Trp Phe Asp Ala Ala Lys Thr Val Asp Lys Thr Val Ser Ile
                20                  25                  30

Ile Ala Glu Ala Ala Arg Asn Gly Cys Glu Leu Val Ala Phe Pro Glu
            35                  40                  45

Val Phe Ile Pro Gly Tyr Pro Tyr His Ile Trp Val Asp Ser Pro Leu
        50                  55                  60

Ala Gly Met Ala Lys Phe Ala Val Arg Tyr His Glu Asn Ser Leu Thr
 65                  70                  75                  80

Met Asp Ser Pro His Val Gln Arg Leu Leu Asp Ala Ala Arg Asp His
                 85                  90                  95

Asn Ile Ala Val Val Gly Ile Ser Glu Arg Asp Gly Gly Ser Leu
            100                 105                 110

Tyr Met Thr Gln Leu Ile Ile Asp Ala Asp Gly Gln Leu Val Ala Arg
        115                 120                 125

Arg Arg Lys Leu Lys Pro Thr His Val Glu Arg Ser Val Tyr Gly Glu
    130                 135                 140

Gly Asn Gly Ser Asp Ile Ser Val Tyr Asp Met Pro Phe Ala Arg Leu
145                 150                 155                 160

Gly Ala Leu Asn Cys Trp Glu His Phe Gln Thr Leu Thr Lys Tyr Ala
                165                 170                 175

Met Tyr Ser Met His Glu Gln Val His Val Ala Ser Trp Pro Gly Met
            180                 185                 190

Ser Leu Tyr Gln Pro Glu Val Pro Ala Phe Gly Val Asp Ala Gln Leu
        195                 200                 205

Thr Ala Thr Arg Met Tyr Ala Leu Glu Gly Gln Thr Phe Val Val Cys
    210                 215                 220

Thr Thr Gln Val Val Thr Pro Glu Ala His Glu Phe Phe Cys Glu Asn
225                 230                 235                 240

Glu Glu Gln Arg Lys Leu Ile Gly Arg Gly Gly Gly Phe Ala Arg Ile
```

```
                    245                 250                 255
Ile Gly Pro Asp Gly Arg Asp Leu Ala Thr Pro Leu Ala Glu Asp Glu
                260                 265                 270

Glu Gly Ile Leu Tyr Ala Asp Ile Asp Leu Ser Ala Ile Thr Leu Ala
            275                 280                 285

Lys Gln Ala Ala Asp Pro Val Gly His Tyr Ser Arg Pro Asp Val Leu
        290                 295                 300

Ser Leu Asn Phe Asn Gln Arg Arg Thr Thr Pro Val Asn Thr Pro Leu
305                 310                 315                 320

Ser Thr Ile His Ala Thr His Thr Phe Val Pro Gln Phe Gly Ala Leu
                325                 330                 335

Asp Gly Val Arg Glu Leu Asn Gly Ala Asp Glu Gln Arg Ala Leu Pro
            340                 345                 350

Ser Thr His Ser Asp Glu Thr Asp Arg Ala Thr Ala Thr Leu
        355                 360                 365

<210> SEQ ID NO 9
<211> LENGTH: 10
<212> TYPE: PRT
<213> ORGANISM: Artificial sequence
<220> FEATURE:
<223> OTHER INFORMATION: Consensus sequence
<220> FEATURE:
<221> NAME/KEY: misc_feature
<222> LOCATION: (10)..(10)
<223> OTHER INFORMATION: Xaa is an amino acid residue which is not
      tyrosine, and is localized at a position corresponding to
      position 296 in wild-type Alcaligenes faecalis nitrilase as
      described by SEQ ID NO: 2

<400> SEQUENCE: 9

Lys Ala Ile Asn Asp Pro Val Gly His Xaa
1               5                   10

<210> SEQ ID NO 10
<211> LENGTH: 8
<212> TYPE: PRT
<213> ORGANISM: Artificial sequence
<220> FEATURE:
<223> OTHER INFORMATION: Consensus sequence
<220> FEATURE:
<221> NAME/KEY: misc_feature
<222> LOCATION: (3)..(3)
<223> OTHER INFORMATION: Xaa is an amino acid residue which is not
      tyrosine, and is localized at a position corresponding to
      position 296 in wild-type Alcaligenes faecalis nitrilase as
      described by SEQ ID NO: 2

<400> SEQUENCE: 10

Gly His Xaa Ser Arg Pro Asp Val
1               5

<210> SEQ ID NO 11
<211> LENGTH: 14
<212> TYPE: PRT
<213> ORGANISM: Artificial sequence
<220> FEATURE:
<223> OTHER INFORMATION: Consensus sequence
<220> FEATURE:
<221> NAME/KEY: misc_feature
<222> LOCATION: (3)..(3)
<223> OTHER INFORMATION: Xaa is Ala or Val
<220> FEATURE:
<221> NAME/KEY: misc_feature
<222> LOCATION: (6)..(6)
<223> OTHER INFORMATION: Xaa is an amino acid residue which is not
      tyrosine, and is localized at a position corresponding to
      position 296 in wild-type Alcaligenes faecalis nitrilase as
```

```
                         described by SEQ ID NO: 2
<220> FEATURE:
<221> NAME/KEY: misc_feature
<222> LOCATION: (12)..(12)
<223> OTHER INFORMATION: Xaa is Leu or Thr
<220> FEATURE:
<221> NAME/KEY: misc_feature
<222> LOCATION: (13)..(13)
<223> OTHER INFORMATION: Xaa is Ser or Arg

<400> SEQUENCE: 11

Asp Pro Ala Gly His Xaa Ser Arg Pro Asp Val Leu Ser Leu
1               5                   10              14

<210> SEQ ID NO 12
<211> LENGTH: 16
<212> TYPE: PRT
<213> ORGANISM: Artificial sequence
<220> FEATURE:
<223> OTHER INFORMATION: Consensus sequence
<220> FEATURE:
<221> NAME/KEY: misc_feature
<222> LOCATION: (6)..(6)
<223> OTHER INFORMATION: Xaa is an amino acid residue which is not
      tyrosine, and is localized at a position corresponding to
      position 296 in wild-type Alcaligenes faecalis nitrilase as
      described by SEQ ID NO: 2

<400> SEQUENCE: 12

Asp Pro Ala Gly His Xaa Ser Arg Pro Asp Val Leu Ser Leu Leu Val
1               5                   10                  15

<210> SEQ ID NO 13
<211> LENGTH: 10
<212> TYPE: PRT
<213> ORGANISM: Artificial sequence
<220> FEATURE:
<223> OTHER INFORMATION: Consensus sequence
<220> FEATURE:
<221> NAME/KEY: misc_feature
<222> LOCATION: (1)..(1)
<223> OTHER INFORMATION: Xaa is Lys or Arg
<220> FEATURE:
<221> NAME/KEY: misc_feature
<222> LOCATION: (2)..(4)
<223> OTHER INFORMATION: Xaa is any amino acid
<220> FEATURE:
<221> NAME/KEY: misc_feature
<222> LOCATION: (6)..(7)
<223> OTHER INFORMATION: Xaa is any amino acid
<220> FEATURE:
<221> NAME/KEY: misc_feature
<222> LOCATION: (8)..(8)
<223> OTHER INFORMATION: Xaa is His, Tyr, or Ser
<220> FEATURE:
<221> NAME/KEY: misc_feature
<222> LOCATION: (10)..(10)
<223> OTHER INFORMATION: Xaa is an amino acid residue which is not
      tyrosine, and is localized at a position corresponding to
      position 296 in wild-type Alcaligenes faecalis nitrilase as
      described by SEQ ID NO: 2

<400> SEQUENCE: 13

Lys Xaa Xaa Xaa Asp Xaa Xaa Gly His Xaa
1               5                   10

<210> SEQ ID NO 14
<211> LENGTH: 24
<212> TYPE: DNA
<213> ORGANISM: Unknown
<220> FEATURE:
<221> NAME/KEY: misc_feature
<222> LOCATION: (1)..(24)
<223> OTHER INFORMATION: primer
```

<400> SEQUENCE: 14
ctcaagctta ggacggctct tgca                                              24

<210> SEQ ID NO 15
<211> LENGTH: 23
<212> TYPE: DNA
<213> ORGANISM: Unknown
<220> FEATURE:
<221> NAME/KEY: misc_feature
<222> LOCATION: (1)..(23)
<223> OTHER INFORMATION: primer

<400> SEQUENCE: 15
ggagatatac atatgcagac aag                                               23

<210> SEQ ID NO 16
<211> LENGTH: 30
<212> TYPE: DNA
<213> ORGANISM: Unknown
<220> FEATURE:
<221> NAME/KEY: misc_feature
<222> LOCATION: (1)..(30)
<223> OTHER INFORMATION: primer
<220> FEATURE:
<221> NAME/KEY: misc_feature
<222> LOCATION: (20)..(22)
<223> OTHER INFORMATION: n is a, c, g, or t

<400> SEQUENCE: 16
caatgacccc gtaggccacn nntccaaacc                                        30

<210> SEQ ID NO 17
<211> LENGTH: 30
<212> TYPE: DNA
<213> ORGANISM: Unknown
<220> FEATURE:
<221> NAME/KEY: misc_feature
<222> LOCATION: (1)..(30)
<223> OTHER INFORMATION: primer
<220> FEATURE:
<221> NAME/KEY: misc_feature
<222> LOCATION: (13)..(15)
<223> OTHER INFORMATION: n is a, c, g, or t

<400> SEQUENCE: 17
ctcgggtttg gannngtggc ctacggggtc                                        30

<210> SEQ ID NO 18
<211> LENGTH: 19
<212> TYPE: DNA
<213> ORGANISM: Unknown
<220> FEATURE:
<221> NAME/KEY: misc_feature
<222> LOCATION: (1)..(19)
<223> OTHER INFORMATION: primer

<400> SEQUENCE: 18
gttcatcttt ccctggttg                                                    19

<210> SEQ ID NO 19
<211> LENGTH: 19
<212> TYPE: DNA
<213> ORGANISM: Unknown
<220> FEATURE:
<221> NAME/KEY: misc_feature
<222> LOCATION: (1)..(19)
<223> OTHER INFORMATION: primer

<400> SEQUENCE: 19

```
gcgttcaccg acaaacaac                                                       19
```

<210> SEQ ID NO 20
<211> LENGTH: 24
<212> TYPE: DNA
<213> ORGANISM: Unknown
<220> FEATURE:
<221> NAME/KEY: misc_feature
<222> LOCATION: (1)..(24)
<223> OTHER INFORMATION: primer

<400> SEQUENCE: 20

```
gtgggccacg cctccaaacc cgag                                                 24
```

<210> SEQ ID NO 21
<211> LENGTH: 24
<212> TYPE: DNA
<213> ORGANISM: Unknown
<220> FEATURE:
<221> NAME/KEY: misc_feature
<222> LOCATION: (1)..(24)
<223> OTHER INFORMATION: primer

<400> SEQUENCE: 21

```
ctcgggtttg gaggcgtggc ccac                                                 24
```

<210> SEQ ID NO 22
<211> LENGTH: 24
<212> TYPE: DNA
<213> ORGANISM: Unknown
<220> FEATURE:
<221> NAME/KEY: misc_feature
<222> LOCATION: (1)..(24)
<223> OTHER INFORMATION: primer

<400> SEQUENCE: 22

```
gtcacgcctc acgccctgat gtgc                                                 24
```

<210> SEQ ID NO 23
<211> LENGTH: 24
<212> TYPE: DNA
<213> ORGANISM: Unknown
<220> FEATURE:
<221> NAME/KEY: misc_feature
<222> LOCATION: (1)..(24)
<223> OTHER INFORMATION: primer

<400> SEQUENCE: 23

```
gcacatcagg gcgtgaggcg tgac                                                 24
```

<210> SEQ ID NO 24
<211> LENGTH: 10
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa is Lys, Arg, or His
<220> FEATURE:
<221> NAME/KEY: MISC_FEATURE
<222> LOCATION: (2)..(4)
<223> OTHER INFORMATION: Xaa is any amino acid
<220> FEATURE:
<221> NAME/KEY: MISC_FEATURE
<222> LOCATION: (6)..(7)
<223> OTHER INFORMATION: Xaa is any amino acid
<220> FEATURE:
<221> NAME/KEY: MISC_FEATURE

```
<222> LOCATION: (9)..(9)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is an amino acid residue which is not
      tyrosine, and is localized at a position corresponding to
      position 296 in wild-type Alcaligenes faecalis nitrilase as
      described by SEQ ID NO: 2

<400> SEQUENCE: 24

Xaa Xaa Xaa Xaa Asp Xaa Xaa Gly Xaa Xaa
 1               5                   10

<210> SEQ ID NO 25
<211> LENGTH: 10
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(4)
<223> OTHER INFORMATION: Xaa is any amino acid
<220> FEATURE:
<221> NAME/KEY: MISC_FEATURE
<222> LOCATION: (6)..(7)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is an amino acid residue which is not
      tyrosine, and is localized at a position corresponding to
      position 296 in wild-type Alcaligenes faecalis nitrilase as
      described by SEQ ID NO: 2

<400> SEQUENCE: 25

Lys Xaa Xaa Xaa Asp Xaa Xaa Gly Xaa Xaa
 1               5                   10
```